US012685733B2

(12) United States Patent
Eoff et al.

(10) Patent No.: US 12,685,733 B2
(45) Date of Patent: Jul. 21, 2026

(54) INDOLE MOLECULES AND USE THEREOF IN THE INHIBITION OF DNA POLYMERASES

(71) Applicant: BioVentures, LLC, Little Rock, AR (US)

(72) Inventors: Robert Eoff, Little Rock, AR (US); Narsimha Penthala, Little Rock, AR (US); Peter Crooks, Little Rock, AR (US)

(73) Assignee: BioVentures, LLC

( * ) Notice: Subject to any disclaimer, the term of this patent is extended or adjusted under 35 U.S.C. 154(b) by 1106 days.

(21) Appl. No.: 17/423,060

(22) PCT Filed: Jan. 14, 2020

(86) PCT No.: PCT/US2020/013533

§ 371 (c)(1),
(2) Date: Jul. 14, 2021

(87) PCT Pub. No.: WO2020/150256

PCT Pub. Date: Jul. 23, 2020

(65) Prior Publication Data

US 2022/0096480 A1 Mar. 31, 2022

Related U.S. Application Data

(60) Provisional application No. 62/792,226, filed on Jan. 14, 2019.

(51) Int. Cl.

| | |
|---|---|
| ***A61P 35/00*** | (2006.01) |
| ***A61K 31/4045*** | (2006.01) |
| ***A61K 31/513*** | (2006.01) |
| ***A61K 31/515*** | (2006.01) |
| ***A61K 31/5377*** | (2006.01) |
| ***A61K 31/565*** | (2006.01) |
| ***A61K 45/06*** | (2006.01) |
| ***C07D 209/14*** | (2006.01) |
| ***C07D 403/06*** | (2006.01) |
| ***C07D 471/04*** | (2006.01) |

(52) U.S. Cl.

CPC ........ *A61K 31/515* (2013.01); *A61K 31/4045* (2013.01); *A61K 31/513* (2013.01); *A61K 31/5377* (2013.01); *A61K 31/565* (2013.01); *A61K 45/06* (2013.01); *A61P 35/00* (2018.01); *C07D 209/14* (2013.01); *C07D 403/06* (2013.01); *C07D 471/04* (2013.01)

(58) Field of Classification Search

None

See application file for complete search history.

(56) References Cited

U.S. PATENT DOCUMENTS

| | | | | |
|---|---|---|---|---|
| 4,241,046 | A | 12/1980 | Papahadjopoulos et al. | |
| 4,394,448 | A | 7/1983 | Szoka, Jr. et al. | |
| 4,529,561 | A | 7/1985 | Hunt et al. | |
| 4,755,388 | A | 7/1988 | Heath et al. | |
| 4,828,837 | A | 5/1989 | Uster et al. | |
| 4,925,661 | A | 5/1990 | Huang | |
| 4,954,345 | A | 9/1990 | Muller | |
| 4,957,735 | A | 9/1990 | Huang | |
| 5,043,164 | A | 8/1991 | Huang et al. | |
| 5,064,655 | A | 11/1991 | Uster et al. | |
| 5,077,211 | A | 12/1991 | Yarosh | |
| 5,264,618 | A | 11/1993 | Felgner et al. | |
| 2004/0002527 | A1* | 1/2004 | Cole .................... | C07D 409/14 548/312.1 |
| 2010/0081678 | A1 | 4/2010 | Crooks et al. | |
| 2015/0328216 | A1 | 11/2015 | Penthala et al. | |

FOREIGN PATENT DOCUMENTS

| | | | |
|---|---|---|---|
| WO | 2014176351 | A1 | 10/2014 |
| WO | 2020150256 | A1 | 7/2020 |

OTHER PUBLICATIONS

Ring, J. et. al., "Improving the inhibitory activity of arylidenaminoguanidine compounds at the N-methyl-D-aspartate receptor complex from a recursive computational-experimental structure-activity relationship study," Bioorg. Med. Chem., Apr. 2013, pp. 1764-1774, vol. 21, No. 7.
Bhatt, A. et al., "Cancer biomarkers—Current perspectives," Indian J. Med. Res., Aug. 2010, pp. 129-149, vol. 132.
Cho, W., "Contribution of oncoproteomics to cancer biomarker discovery," Mol. Cancer, Apr. 2007, pp. 1-13, vol. 6, No. 25.
Chou, T-C., "Drug Combination Studies and Their Synergy Quantification Using the Chou-Talalay Method," Cancer Res., Jan. 2010, pp. 440-446, vol. 70, No. 2.
Elhai, J. et al., "Conjugal Transfer of DNA to Cyanobacteria," Methods in Enzymology, 1988, pp. 747-754, vol. 167.
International Search Report and Written Opinion dated Jun. 11, 2020 from related Patent Application No. PCT/US2020/013533; 12 pgs.

(Continued)

*Primary Examiner* — Brenda L Coleman
*Assistant Examiner* — Madeline E Braun
(74) *Attorney, Agent, or Firm* — Norton Rose Fulbright US LLP

(57) ABSTRACT

The present disclosure is directed to compositions and methods for the inhibition of DNA polymerases. the compositions disclosed herein include one or more of indole-derived compounds useful in treatment of cancers including those which are resistant to genotoxic therapies.

14 Claims, 27 Drawing Sheets
(18 of 27 Drawing Sheet(s) Filed in Color)
Specification includes a Sequence Listing.

(56) References Cited

OTHER PUBLICATIONS

Ketkar, A. et al., "Inhibition of Human DNA Polymerases Eta and Kappa by Indole-Derived Molecules Occurs through Distinct Mechanisms," ACS Chem. Biol., 2019, pp. 337-1351, vol. 14, No. 6.
Louis, D. et al., "The 2007 WHO Classification of Tumours of the Central Nervous System," Acta Neuropathol., 2007, pp. 97-109, vol. 114, No. 2.
Peng, C. et al., "The Error-Prone DNA Polymerase kappa Promotes Temozolomide Resistance in Glioblastoma through Rad17-Dependent Activation of ATR-Chk1 Signaling," Cancer Res., Apr. 2016, pp. 2340-2353, vol. 76, No. 8.
Prasad, R. et al., "Acylation of guanidines and guanylhydrazones," Canadian J. Chem., 1967, pp. 2247-2252, vol. 45, No. 19.
Studier, W., "Protein production by auto-induction in high-density cultures," Protein Expr. Purif., 2005, pp. 207-234, vol. 41.
Wang, H. et al., "Analysis of specialized DNA polymerases expression in human gliomas: association with prognostic significance, " Neuro-Oncol., Feb. 2010, pp. 679-686, vol. 12, No. 7.
Wen, P. et al., "Malignant Gliomas in Adults," N. Engl. J. Med., Jul. 2008, pp. 492-507, vol. 359, No. 5.
Zafar, M. et al., "A Small-Molecule Inhibitor of Human DNA Polymerase η Potentiates the Effects of Cisplatin in Tumor Cells," HHS Public Access Author Manuscript, Jun. 24, 2020, pp. 1-26, published in final edited form as: Biochemistry, Feb. 20, 2018, pp. 1262-1273, vol. 57, No. 7.

* cited by examiner

Formula (V)

Formula (VI)

IBA Scaffolds

IGA Scaffolds

Mean ± s.d. shown for n=3

General Structure I $R^1$ = H, $CH_3$, Cl, Br, $COOC_2H_5$, OH, COOH, $COOCH_3$
$R^2$ = $R^3$ = $R^4$ = H, $CH_3$, F, Cl, Br, $OCH_3$, OH, CN, $NH_2$,
$CH_2$-OH, $CH_2NH_2$,, -$OCH_2$-$CH_2$-N-$(C_2H_5)_2$, -$OCH_2$-$CH_2$-N-$(CH_3)_2$,
-$CH_2$-O-$PO_3^{-2}$, NH-$SO_2$-$CH_3$, $CF_3$, $OCHF_2$, -O-$CH_2$-$CH_2$-$NH_2$,

Y = O, NH, N-$CH_3$

General Structure II $R^1$ = H, $CH_3$, Cl, Br, $COOC_2H_5$, OH, COOH, $COOCH_3$ $R^2 = R^3 = R^4$ = H, $CH_3$, F, Cl, Br, $OCH_3$, OH, CN, $NH_2$, $CH_2$-OH, $CH_2NH_2$,, $-OCH_2-CH_2-N-(C_2H_5)_2$, $-OCH_2-CH_2-N-(CH_3)_2$, $-CH_2-O-PO_3^{-2}$, $NH-SO_2-CH_3$, $CF_3$, $OCHF_2$, $-O-CH_2-CH_2-NH_2$,

Y = O, NH, N-$CH_3$

General Structure II $R^1$ = H, $CH_3$, Cl, Br, $COOC_2H_5$, OH, COOH, $COOCH_3$
$R^2$ = $R^3$ = $R^4$ = H, $CH_3$, F, Cl, Br, $OCH_3$, OH, CN, $NH_2$,
$CH_2$-OH, $CH_2NH_2$,, -$OCH_2$-$CH_2$-N-$(C_2H_5)_2$, -$OCH_2$-$CH_2$-N-$(CH_3)_2$,
-$CH_2$-O-$PO_3^{-2}$, NH-$SO_2$-$CH_3$, $CF_3$, $OCHF_2$, -O-$CH_2$-$CH_2$-$NH_2$,

Y = O, NH, N-$CH_3$

INDOLE MOLECULES AND USE THEREOF IN THE INHIBITION OF DNA POLYMERASES

CROSS REFERENCE TO RELATED APPLICATIONS

This application claims the benefit of International Application No. PCT/US2020/013533, filed Jan. 14, 2020 which claims the benefit of U.S. Provisional Application 62/792,226, filed Jan. 14, 2019, each of the disclosures of which are hereby incorporated by reference in their entirety.

GOVERNMENTAL RIGHTS

This invention was made with government support under CA183895 and AG012411-17A1 awarded by the National Institutes of Health. The government has certain rights in the invention.

INCORPORATION OF SEQUENCE LISTING

The instant application contains a Sequence Listing which has been submitted electronically in computer readable form (.txt) format and is hereby incorporated by reference in its entirety. Said .txt copy, created on Jul. 14, 2021, is named 687575 Sequence Listing ST25, and is 14,491 bytes in size.

FIELD OF THE TECHNOLOGY

This application generally relates to compositions and methods for the treatment of cancer. In particular, the present disclosure provides compositions comprising one or more of indole-derived compounds useful in treatment of cancers including those which are resistant to genotoxic therapies.

BACKGROUND

Genotoxic therapies (e.g., DNA damaging agents) in oncology are widely used to treat both hematological and solid cancers. Commonly used modalities include ionizing radiation, platinum drugs (cisplatin, oxaliplatin, and carboplatin), cyclophosphamide, chlorambucil, and temozolomide. These agents work to induce apoptosis and subsequently eliminate cancer cells from the body by modifying the chemical structure of nucleic acid. Unfortunately, the efficacy of these agents can be significantly reduced by various factors that drive drug resistance. For example, increases in drug efflux and/or increased drug metabolism can lower the intracellular concentration of an anti-cancer agent thereby reducing its ability to inflict enough DNA damage to induce apoptosis. Another mechanism involves deletions or mutations in proteins associated with several DNA repair pathways that respond to damaged DNA. For example, cancers such as Li-Fraumeni Syndrome and Lynch Syndrome (formerly referred to as hereditary non-polyposis colorectal cancer (HNPCC)) possess mutations in p53, a key regulator in DNA damage response or DNA mismatch repair, respectively. In these cases, the inability of a cancer cell to appropriately respond to DNA damage or repair it allows an oncogenic cell to survive the cellular insults caused by DNA damaging agents.

Moreover, cancer cells that survive these insults are more likely to undergo cell division and proliferate rather than die via apoptosis. This occurs as unrepaired DNA lesions are effectively by-passed by two mutually exclusive pathways. The first involves homologous recombination which, in most cases, allows for "error-free" by-pass of a lesion. The alternative pathway reflects the ability of DNA polymerases to efficiently insert nucleotides opposite and beyond a DNA lesion. This activity, termed translesion DNA synthesis (TLS), can be highly pro-mutagenic and generate more mutations in a cancer cell. In turn, higher mutation frequencies can create more aggressive cancers and/or lead to tumor recurrence.

An unfortunate example of this phenomenon occurs during the treatment of patients diagnosed with glioblastoma multiforme (GBM). Standard treatments for GBM include administration of the DNA alkylating agent, temozolomide. While this drug is initially effective in reducing tumor burden, its efficacy typically diminishes within a year due to the emergence of drug resistance caused by mutagenesis of proteins such as those involved in DNA repair. Indeed, a recent report highlights a role for TLS activity in generating resistance as temozolomide-treated tumors display higher mutation rates (~90 mutations/Mb) compared to initial untreated tumors (<4 mutations/Mb). Furthermore, these hypermutation rates coincided with mutations in key genes associated with DNA mismatch repair, retinoblastoma, and mammalian target of rapamycin (mTOR).

Malignant gliomas and central nervous system tumors are the most common type of primary brain tumors, with an annual incidence of 5/100,000 individuals. More than 11 million individuals are diagnosed with gliomas annually, and the projected number will rise to 16 million by the year 2020. Overall incidence is very similar among countries. Glioblastoma multiformes are slightly more common in the United States, Scandinavia, and Israel than in Asia. This may reflect differences in genetics, diagnosis and the healthcare system, and reporting practices. Glioblastoma multiforme is the most frequent primary brain tumor, accounting for approximately 12-15% of all intracranial neoplasms and 50-60% of all astrocytic tumors. In most European and North American countries, incidence is approximately 2-3 new cases per 100,000 people per year.

The treatment of GBM, is especially challenging, all GBM patients exhibit relapse and fail to respond to treatment; however, some additional treatment options are available for gliomas, which include passive and active immunotherapy, use of angiogenesis inhibitors in combination with chemotherapeutics and gene/antibody therapy. However, none of the above-mentioned therapies have been successful in curing this disease. Additionally, penetration of the blood brain barrier (BBB) is a major obstacle to the development of effective therapies for central nervous system (CNS) tumors.

It is therefore of great interest to develop novel therapeutics useful in the treatment of cancer and in particular cancers which are resistant to genotoxic therapies.

SUMMARY

One aspect of the present disclosure is directed to compounds of Formula (I):

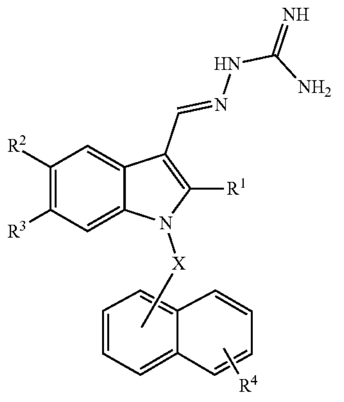

wherein $R^1$ is selected from the group consisting of hydrogen, deuterium, halogen, $CH_3$, Cl, Br, $COOC_2H_5$, OH, COOH, $COOCH_3$, $OCH_3$, OR', SR', NR'R', NR'COR', NR'CONR'R', $NR'CO_2R'$, COR', $CO_2R'$, NOR', $NO_2$, CONR'R', OC(O)NR'R', $SO_2R'$, $SO_2NR'R'$, $NR'SO_2R'$, $NR'SO_2NR'R'$, C(O)C(O)R', $C(O)CH_2C(O)R'$, a substituted or unsubstituted $C_1$-$C_6$ alkyl, a substituted or unsubstituted $C_1$-$C_6$ alkenyl, a substituted or unsubstituted $C_1$-$C_6$ alkynyl, a substituted or unsubstituted aryl, and a substituted or unsubstituted heteroaryl; R' is independently selected from the group consisting of hydrogen, substituted $C_1$-$C_4$ aliphatic moiety, aliphatic moiety containing nitrogen, oxygen, or sulfur, or alternately, two R' moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur;

wherein $R^2$, $R^3$, and $R^4$ are independently selected from the group consisting of hydrogen, deuterium, halogen, $CH_3$, F, Cl, Br, $OCH_3$, OH, CN, $NH_2$, $CH_2OH$, $CH_2NH_2$, OCH2CH2N(CH2H5)2, $OCH_2CH_2N(CH_3)_2$, $CH_2OPO_3^{-2}$, $NHSO_2CH_3$, $CF_3$, $OCHF_2$, $OCH_2CH_2NH_2$, $COOC_2H_5$, COOH, $COOCH_3$,

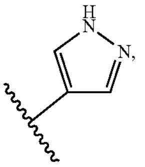
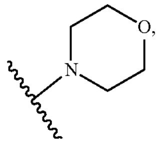
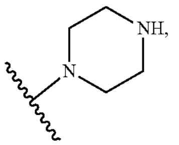
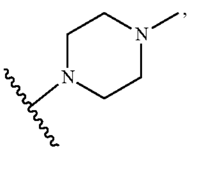
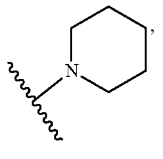
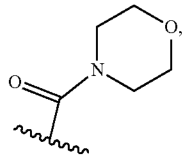

-continued

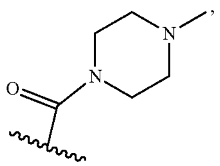
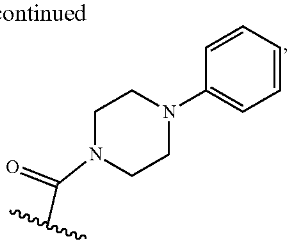
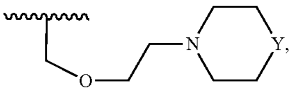

OR', SR', NR'R', NR'COR', NR'CONR'R', $NR'CO_2R'$, COR', $CO_2R'$, NOR', $NO_2$, CONR'R', OC(O)NR'R', $SO_2R'$, $SO_2NR'R'$, $NR'SO_2R'$, $NR'SO_2NR'R'$, C(O)C(O)R', $C(O)CH_2C(O)R'$, a substituted or unsubstituted $C_1$-$C_6$ alkyl, a substituted or unsubstituted $C_1$-$C_6$ alkenyl, a substituted or unsubstituted $C_1$-$C_6$ alkynyl, a substituted or unsubstituted aryl, and a substituted or unsubstituted heteroaryl; R' is independently selected from the group consisting of hydrogen, substituted $C_1$-$C_4$ aliphatic moiety, aliphatic moiety containing nitrogen, oxygen, or sulfur, or alternately, two R' moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur: Y is independently selected from O, NH, or N—$CH_3$; and wherein X is independently selected from $CH_2$, CO and $SO_2$.

Another aspect of the present disclosure is directed to a method of inhibiting DNA-polymerase kappa in a cell or in a subject in need thereof. The method comprises administering to the cell or to the subject a composition comprising a therapeutically effective amount of a compound of Formula (I) as described herein.

An additional aspect of the present disclosure is directed to a method treating or preventing a cancer or tumor in a subject, the method comprising administering a composition comprising a therapeutically effective amount of a compound of Formula (I) as described herein, wherein the cancer or tumor is selected from glioblastoma, hematological tumors such as leukemia, lymphoma and multiple myeloma, and solid tumors such as lung cancer, liver cancer, pancreatic cancer, CNS cancers, breast cancer, ovarian cancer, colon cancer, renal cancer, melanoma, prostate cancer and head and neck cancer.

In various embodiments, the present teachings include use of a compound of Formula (I) for the manufacture of a medicament to treat a cancer or tumor.

BRIEF DESCRIPTION OF THE FIGURES

The application file contains at least one drawing executed in color. Copies of this patent application publication with color drawing(s) will be provided by the Office upon request and payment of the necessary fee.

FIG. 1A shows the chemical structure of IBA scaffolds. FIG. 1B shows the chemical structure of IGA scaffolds. FIG. 1C is a graph showing hPol κ activity, relative to a DMSO control experiment, for all the compounds containing the IBA scaffold. Each compound was used at a concentration of 40 μM in the screen. The compound identification is noted below each histogram. The chemical structure and detailed activity information for each compound are listed in Table 1. The results represent the mean (±SD) for experiments performed in triplicate. FIG. 1D is a graph showing hPol κ activity, relative to a DMSO control experiment, for all the compounds containing the IAG scaffold. Each compound was used at a concentration of 40 μM in the screen. The compound identification is noted below each histogram. The chemical structure and detailed activity information for each compound are listed in Table 2. The results represent the mean (±SD) for experiments performed in triplicate.

FIG. 2A provides the chemical structure of IAG-10. FIG. 2B shows the activity of the four human Y-family pols measured in the presence of IAG-10 (10 μM). The concentrations of the enzymes were: 1 nM hpol κ, 2 nM hpol η, 10 nM hpol ι, and 10 nM Revl. The percent activity relative to a DMSO control experiment is shown. FIG. 2C shows the activity of hpol κ (25 nM), Tb pol I (10 nM), *S. solfataricus* Dpol (25 nM), hpol β (1 nM), and hpol λ (10 nM) measured in the presence of IAG-10 (10 μM). The percent activity relative to a DMSO control experiment is shown. The results shown represent the mean (±SD) for three independent replicates. A two-tailed unpaired Student's t test was used to compare the results for hpol κ with those of the other DNA pols (=P<0.005 and *=P<0.0001). FIG. 2D is a graph showing IAG-10 is a potent and selective small-molecule inhibitor of hpol κ.

FIG. 3A provides the chemical structure of IBA-32, an IBA derivative. FIG. 3B shows the equilibrium dissociation constants for hpol κ. FIG. 3C shows the binding of hpol η to DNA ($K_{D,DNA}$). The $K_{D,DNA}$ values measured for hpol κ were replotted as a function of inhibitor concentration and fit to a second order polynomial equation ($Y=b+m_1x+m_2x^2$). The $K_{D,DNA}$ values measured for hpol η were replotted as a function of inhibitor concentration, and linear regression was used to calculate the slope and y-intercept.

FIG. 4A is a graph showing the concentration of enzyme and DNA in the reaction mixture was varied, and the $IC_{50}$ for inhibition of hpol κ by IAG-10 was measured. Fitting the results to eq 1 resulted in the following $IC_{50}$ values: 50 nM DNA (black circles), 7.2 (6.7 to 7.8) μM; 25 nM DNA (orange squares), 8.9 (8.7 to 9.2) μM; 10 nM DNA (blue triangles), 8.9 (8.6 to 9.2) μM; 2.5 nM DNA (red triangles), 1.4 (1.3 to 1.6) μM; 1 nM DNA (purple diamonds), 1.1 (1.0 to 1.1) μM; 0.5 nM DNA (open circles), 0.72 (0.69 to 0.76) μM. FIG. 4B is a graph showing the concentration of enzyme and DNA in the reaction mixture was varied, and the $IC_{50}$ for inhibition of hpol η by IAG-10 was measured. Fitting the results to eq 1 resulted in the following $IC_{50}$ values: 50 nM DNA (black circles), 14.3 (12.8 to 15.9) μM; 2 nM DNA (open squares), 22.5 (21.7 to 23.3) μM. The results shown in both panels represent the mean (±SD) for three independent replicates. Values in parentheses represent the 95% confidence interval derived from the fit of the data.

FIG. 5A shows the turnover number ($K_{cat}$) in the presence of varying concentrations of IAG-10. FIG. 5B shows Michaelis constant ($K_{m,dNTP}$) measured for hpol κ-catalyzed insertion of dTTP in the presence of varying concentrations of IAG-10. FIG. 5C shows the turnover number ($K_{cat}$) in the presence of varying concentrations of IBA-32. FIG. 5D shows Michaelis constant ($K_{m,dNTP}$) measured for hpol κ-catalyzed insertion of dTTP in the presence of varying concentrations of IBA-32. FIG. 5E shows the hpol η catalysis (turnover number ($K_{cat}$)) in the presence of varying concentrations of IAG-10 in the presence of IAG-10. FIG. 5F shows Michaelis constant ($K_{m,dNTP}$) measured for hpol η-catalyzed insertion of dTTP in the presence of varying concentrations of IAG-10. The results shown in all panels represent the mean (±SD) for three independent replicates.

FIG. 6A shows total ion chromatograms for peptides containing HPG-modified Arg48 following incubation with HPG alone (black), HPG+1AG-10 (20 μM; magenta), or HPG+IAG-10 (100 μM; cyan) (SEQ ID NO: 1). FIG. 6B shows total ion chromatograms for peptides containing HPG-modified Arg505 following incubation with HPG alone (black), HPG+1AG-10 (20 μM; magenta), or HPG+IAG-10 (100 μM; cyan)(SEQ ID NO: 2). FIG. 6C shows the fraction of HPG-modified peptide calculated for each of the 15 peptides. FIG. 6D shows the structure of hpol κ with HPG modified peptides highlighted in cyan. HPG-modified peptides that exhibited a decrease of >1.5-fold upon addition of IAG-10 (ie., protected) are shown in red, and those that exhibited an increase of >1.5-fold (ie., exposed) are shown in blue. Arginine residues showing the most change in HPG modification upon addition of IAG-10 are represented in ball-and-stick and are labeled.

FIG. 7A shows representative images for hpol κ-proficient HAP-1 cells, the top panel represents colonies formed by untreated cells (CTL), the middle panel shows an image of HAP-1 cells treated with 250 μM TMZ (TMZ), while the bottom panel shows cells treated with 250 μM TMZ and 0.5 IAG-10 in combination (TMZ+IAG-10). Results at all concentrations of TMZ (as indicated) are shown as curves on the right. The number of colonies formed as a function of TMZ concentration is represented as a dose-response plot for the hpol κ-proficient cells treated with TMZ (black circles) or TMZ+0.5 μM IAG-10 (red circles). FIG. 7B shows similar results as in FIG. 7A for the clonogenic assay performed with hpol κ-deficient HAP-1 cells. Results shown in FIG. 7A and FIG. 7B represent mean (±SD) for three biological replicates. FIG. 7C shows colonies of HAP-1 cells treated as described in FIG. 7A were counted, and the results are represented as bar graphs for each condition (Control, TMZ-treated, and TMZ-IAG-10-treated). The solid black bars represent results from hpol κ-proficient cells, while the patterned bars represent results for the hpol κ-deficient cells. The mean (±s.d.) is shown for three biological replicates. FIG. 7D shows results from the alkaline comet assay performed with the hpol κ-proficient HAP-1 cells. FIG. 7E shows results from the alkaline comet assay performed with the hpol κ-deficient HAP-1 cells. The four vertical panels on the left of both FIG. 7D and FIG. 7E are the representative images of single cells showing the SYBR-Gold stained DNA. The four panels show images from a control cell, a cell treated with 0.5 μM IAG-10 alone or 100 μM TMZ alone, or a combination of both IAG-10 and TMZ, respectively. To the right, the graph depicts results from the comet assay measurements for at least 60 cells per condition from three biological replicates (minimum of 20 cells per replicate). The mean (±SD) is shown for each experimental condition. Black open circles represent control cells; blue represent the IAG-10 treated cells, and red represent the TMZ treated cells. Brown circles represent cells treated with a combination of the two. The % DNA in the tail calculated for each cell from the comet assay is shown on the Y-axis. Significance among treatment conditions was calculated using one-way ANOVA with the Bonferroni posthoc correction.

FIG. 8 A shows clonogenic survival graphs for GMB-derived T98G. FIG. 8 B shows clonogenic survival graphs for hpol k-knock out cells. FIG. 8C shows clonogenic survival graphs for non-malignant NT2 treated with TMZ alone and in combination with IAG-10. Data represents mean±s.d. (n=3).

FIG. 9A shows results for the calculated mutational frequency for each experimental sample (hpol κ-proficient). FIG. 9B shows results for the calculated mutational frequency for each experimental sample (hpol κ-deficient). For each condition, at least 10,000 colonies were counted. Black circles represent the untreated cells, while magenta squares show the IAG-10 treated cells. The results are shown as mean (±SD) for each condition. P-values were calculated using a two-way ANOVA with Sidak's multiple comparison test.

FIG. 12A shows BrdU+ MCF7 cells. FIG. 12B shows cell death in sub-G1 cells in the MCF7 cell line.

FIG. 13A shows a cartoon illustration of hpol η inhibition by indole-derived compounds. FIG. 13B shows a cartoon illustration of hpol k inhibition by indole-derived compounds.

DETAILED DESCRIPTION

Figure 1A:
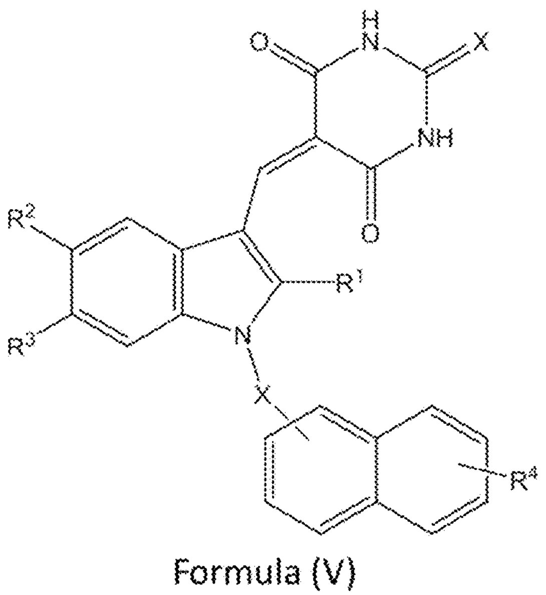
FIG. 1A-1D include chemical scaffolds of indole-derived molecules and histograms showing inhibitory properties against hpol κ.
Figure 1A:
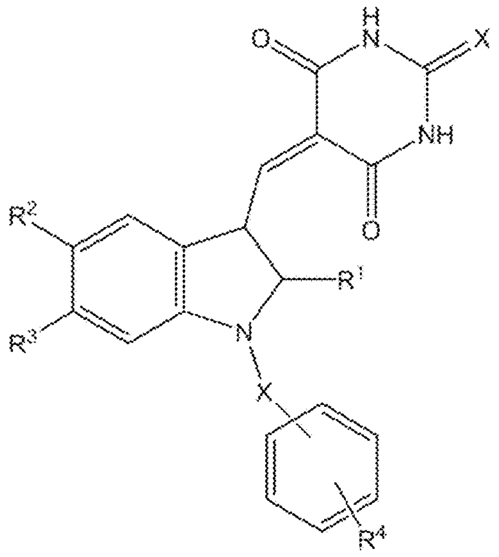

Compositions comprising one or more indole-derived molecules and methods of use are provided herein. Applicants have discovered that the compositions disclosed herein are selective and potent DNA-polymerases. In some embodiments, the present disclosure provides selective and potent inhibitors of DNA pol kappa (hpol κ). Moreover, the disclosed compositions are found to provide unexpected synergistic effects when combined with standard-of-care genotoxic agents. In particular, the disclosed compositions are shown to potentiate the anti-proliferative effects of temozolomide. Accordingly, the present disclosure provides methods of treating a tumor or cancer.

Additional aspects of the disclosure are described below.

(I) Compositions

One aspect of the present disclosure encompasses Indole-derived molecules (e.g., indoleaminoguanidine (IAG) compounds and indole barbitutri acid (IBA) compounds). In various embodiments the IAG analogs can be synthesized by methods disclosed herein. The IAG and/or IBA compounds disclosed herein may be modified to improve potency, bioavailability, solubility, stability, handling properties, or a combination thereof, as compared to an unmodified version. Thus, in another aspect, a composition of the disclosure comprises modified IAG and/or IBA compound. In still another aspect, a composition of the disclosure comprises a prodrug of an IAG or IBA compound disclosed herein.

A composition of the disclosure may optionally comprise one or more additional drug or therapeutically active agent in addition to the IAG and/or IBA compounds. A composition of the disclosure may further comprise a pharmaceutically acceptable excipient, carrier, or diluent. Further, a composition of the disclosure may contain preserving agents, solubilizing agents, stabilizing agents, wetting agents, emulsifiers, sweeteners, colorants, odorants, salts (substances of the present invention may themselves be provided in the form of a pharmaceutically acceptable salt), buffers, coating agents, or antioxidants.

Other aspects of the invention are described in further detail below.

(a) Indoleaminoguanidine Compounds

In general, the compounds detailed herein include compounds comprising a 1 or 2-naphthoyl, 1 or 2-naphthalenylmethyl or a naphthalene-1-ylsulfonyl/naphthalene-2-ylsulfonyl indole aminoguanidine analog, structures as diagrammed below.

Provided herein are compounds comprising Formula (I) and salts thereof:

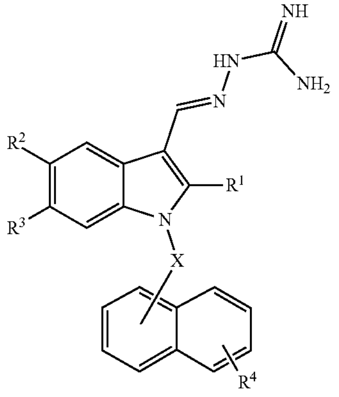

wherein $R^1$ is selected from the group consisting of hydrogen, deuterium, halogen, $CH_3$, Cl, Br, $COOC_2H_5$, OH, COOH, $COOCH_3$, $OCH_3$, OR', SR', NR'R', NR'COR', NR'CONR'R', $NR'CO_2R'$, COR', $CO_2R'$, NOR', $NO_2$, CONR'R', OC(O)NR'R', $SO_2R'$, $SO_2NR'R'$, $NR'SO_2R'$, $NR'SO_2NR'R'$, C(O)C(O)R', $C(O)CH_2C(O)R'$, a substituted or unsubstituted $C_1$-$C_6$ alkyl, a substituted or unsubstituted $C_1$-$C_6$ alkenyl, a substituted or unsubstituted $C_1$-$C_6$ alkynyl, a substituted or unsubstituted aryl, and a substituted or unsubstituted heteroaryl; R' is independently selected from the group consisting of hydrogen, substituted $C_1$-$C_4$ aliphatic moiety, aliphatic moiety containing nitrogen, oxygen, or sulfur, or alternately, two R' moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur;

wherein $R^2$, $R^3$, and $R^4$ are independently selected from the group consisting of hydrogen, deuterium, halogen, $CH_3$, F, Cl, Br, $OCH_3$, OH, CN, $NH_2$, $CH_2OH$, $CH_2NH_2$, OCH2CH2N(CH2H5)2, $OCH_2CH_2N(CH_3)_2$, $CH_2OPO_3^{-2}$, $NHSO_2CH_3$, $CF_3$, $OCHF_2$, $OCH_2CH_2NH_2$, $COOC_2H_5$, COOH, $COOCH_3$,

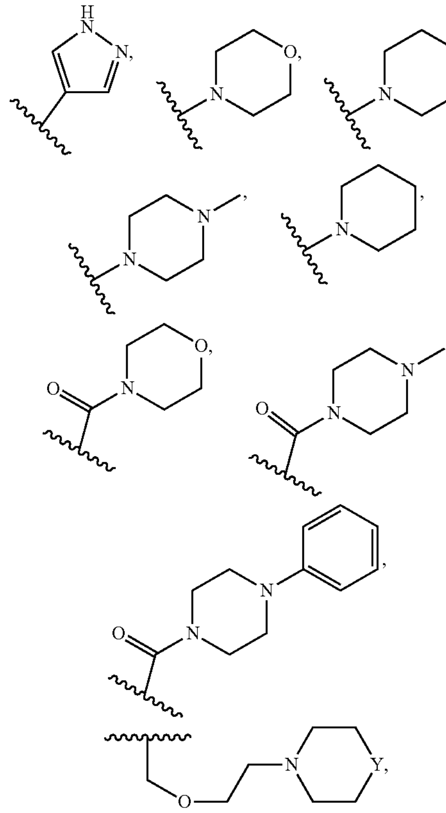

OR', SR', NR'R', NR'COR', NR'CONR'R', NR'$CO_2$R', COR', $CO_2$R', NOR', NO2, CONR'R', OC(O)NR'R', $SO_2$R', $SO_2$NR'R', NR'$SO_2$R', NR'$SO_2$NR'R', C(O)C(O)R', C(O)$CH_2$C(O)R', a substituted or unsubstituted $C_1$-$C_6$ alkyl, a substituted or unsubstituted $C_1$-$C_6$ alkenyl, a substituted or unsubstituted $C_1$-$C_6$ alkynyl, a substituted or unsubstituted aryl, and a substituted or unsubstituted heteroaryl; R' is independently selected from the group consisting of hydrogen, substituted $C_1$-$C_4$ aliphatic moiety, aliphatic moiety containing nitrogen, oxygen, or sulfur, or alternately, two R' moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur: Y is independently selected from O, NH, or N—$CH_3$; and wherein X is independently selected from $CH_2$, CO and $SO_2$.

In an embodiment, a compound of Formula (I) comprises any of the preceding compounds of Formula (I), wherein $R^1$ may be selected from the group hydrogen, $CH_3$, Cl, Br, $COOC_2H_5$, OH, COOH, and $COOCH_3$. In a preferred embodiment, a compound of Formula (I) comprises any of the preceding compounds of Formula (I), wherein $R^1$ is H.

In an embodiment, a compound of Formula (I) comprises any of the preceding compounds of Formula (I), wherein $R^2$ may be selected from the group hydrogen, $CH_3$, F, Cl, Br, $OCH_3$, OH, CN, $NH_2$, $CH_2OH$, $CH_2NH_2$, OCH2CH2N(CH2H5)2, $OCH_2CH_2N(CH_3)_2$, $CH_2OPO_3^{-2}$, $NHSO_2CH_3$, $CF_3$, $OCHF_2$, $OCH_2CH_2NH_2$, $COOC_2H_5$, COOH, $COOCH_3$,

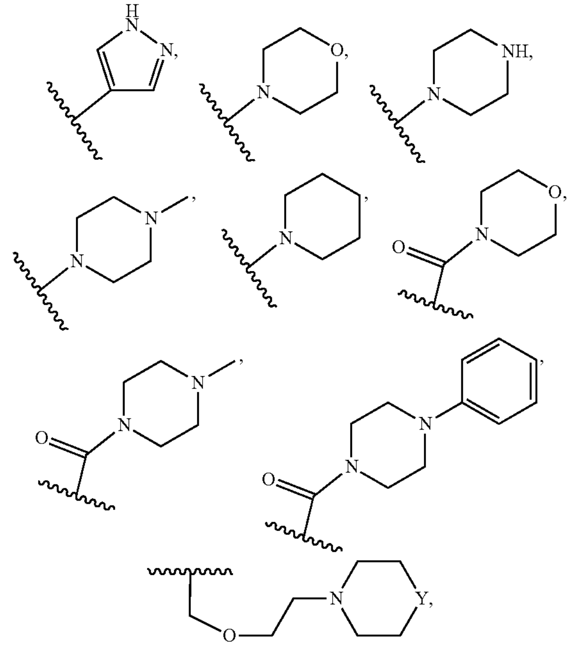

wherein Y is independently selected from O, NH, or N—$CH_3$. In a preferred embodiment, a compound of Formula (I) comprises any of the preceding compounds of Formula (I), wherein $R^2$ is Cl.

In another embodiment, a compound of Formula (I) comprises any of the preceding compounds of Formula (I), wherein $R^3$ may be selected from the group hydrogen, $CH_3$, F, Cl, Br, $OCH_3$, OH, CN, $NH_2$, $CH_2OH$, $CH_2NH_2$, OCH2CH2N(CH2H5)2, $OCH_2CH_2N(CH_3)_2$, $CH_2OPO_3^{-2}$, $NHSO_2CH_3$, $CF_3$, $OCHF_2$, $OCH_2CH_2NH_2$, $COOC_2H_5$, COOH, $COOCH_3$,

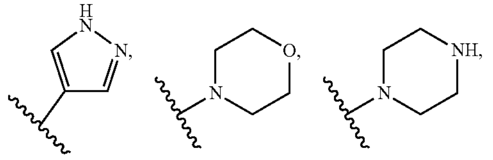

-continued

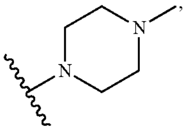,
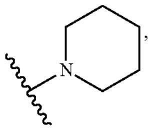,
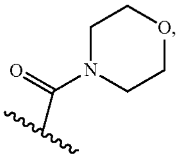,
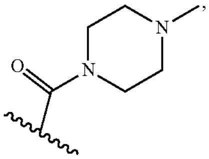,
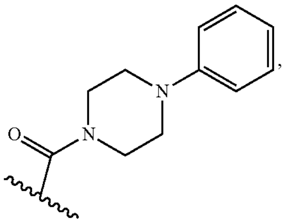,
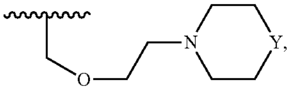, wherein Y is independently selected from O, NH, or N—$CH_3$. In a preferred embodiment, a compound of Formula (I) comprises any of the preceding compounds of Formula (I), wherein $R^3$ is H.

In still another embodiment, a compound of Formula (I) comprises any of the preceding compounds of Formula (I), wherein $R^4$ may be selected from the group hydrogen, $CH_3$, F, Cl, Br, $OCH_3$, OH, CN, $NH_2$, $CH_2OH$, $CH_2NH_2$, OCH2CH2N(CH2H5)2, $OCH_2CH_2N(CH_3)_2$, $CH_2OPO_3^{-2}$, $NHSO_2CH_3$, $CF_3$, $OCHF_2$, $OCH_2CH_2NH_2$, $COOC_2H_5$, COOH, $COOCH_3$,

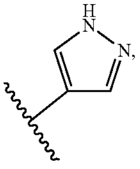,
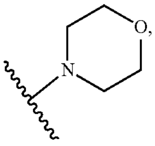,
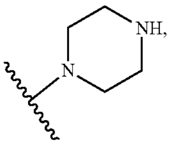,
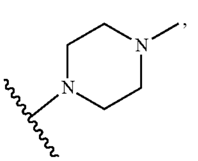,
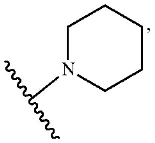,
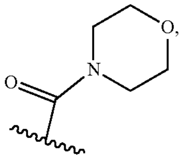,
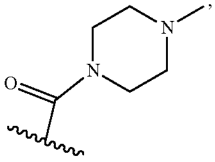,
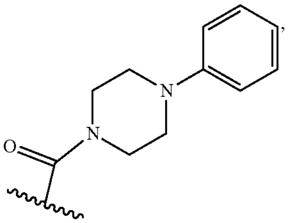,
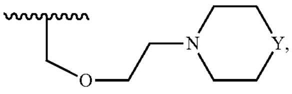, wherein Y is independently selected from O, NH, or N—$CH_3$. In a preferred embodiment, a compound of Formula (I) comprises any of the preceding compounds of Formula (I), wherein $R^4$ is H.

In yet still another embodiment, a compound of Formula (I) comprises any of the preceding compounds of Formula (I), wherein X is independently selected from $CH_2$, CO and $SO_2$. In a preferred embodiment, a compound of Formula (I) comprises any of the preceding compounds of Formula (I), wherein X is CO.

In another embodiment, provided herein are compounds comprising Formula (II) and salts thereof:

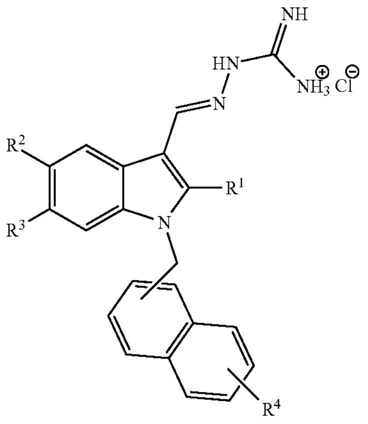

wherein $R^1$ is selected from the group consisting of hydrogen, deuterium, halogen, $CH_3$, Cl, Br, $COOC_2H_5$, OH, COOH, $COOCH_3$, $OCH_3$, OR', SR', NR'R', NR'COR', NR'CONR'R', NR'$CO_2$R', COR', $CO_2$R', NOR', $NO_2$, CONR'R', OC(O)NR'R', $SO_2$R', $SO_2$NR'R', NR'$SO_2$R', NR'$SO_2$NR'R', C(O)C(O)R', C(O)$CH_2$C(O)R', a substituted or unsubstituted $C_1$-$C_6$ alkyl, a substituted or unsubstituted $C_1$-$C_6$ alkenyl, a substituted or unsubstituted $C_1$-$C_6$ alkynyl, a substituted or unsubstituted aryl, and a substituted or unsubstituted heteroaryl; R' is independently selected from the group consisting of hydrogen, substituted $C_1$-$C_4$ aliphatic moiety, aliphatic moiety containing nitrogen, oxygen, or sulfur, or alternately, two R' moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur;

wherein $R^2$, $R^3$, and $R^4$ are independently selected from the group consisting of hydrogen, deuterium, halogen, $CH_3$, F, Cl, Br, $OCH_3$, OH, CN, $NH_2$, $CH_2OH$, $CH_2NH_2$, OCH2CH2N(CH2H5)2, $OCH_2CH_2N(CH_3)_2$, $CH_2OPO_3^{2-}$, $NHSO_2CH_3$, $CF_3$, $OCHF_2$, $OCH_2CH_2NH_2$, $COOC_2H_5$, COOH, $COOCH_3$,

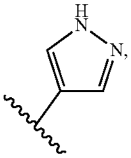,
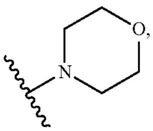,
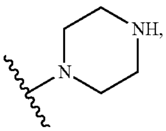,

-continued

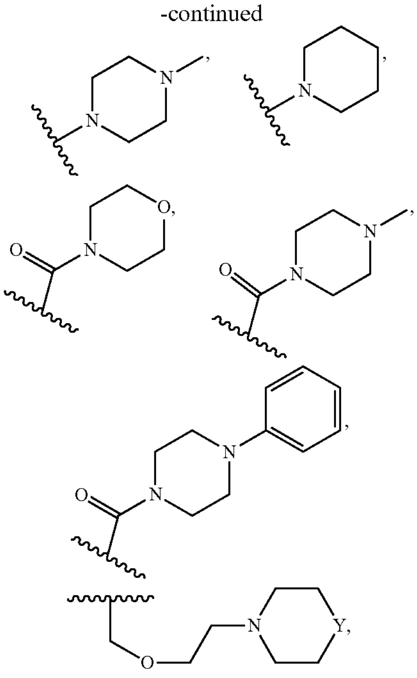

OR', SR', NR'R', NR'COR', NR'CONR'R', NR'$CO_2$R', COR', $CO_2$R', NOR', $NO_2$, CONR'R', OC(O)NR'R', $SO_2$R', $SO_2$NR'R', NR'$SO_2$R', NR'$SO_2$NR'R', C(O)C(O)R', C(O)$CH_2$C(O)R', a substituted or unsubstituted $C_1$-$C_6$ alkyl, a substituted or unsubstituted $C_1$-$C_6$ alkenyl, a substituted or unsubstituted $C_1$-$C_6$ alkynyl, a substituted or unsubstituted aryl, and a substituted or unsubstituted heteroaryl; R' is independently selected from the group consisting of hydrogen, substituted $C_1$-$C_4$ aliphatic moiety, aliphatic moiety containing nitrogen, oxygen, or sulfur, or alternately, two R' moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur: Y is independently selected from O, NH, or N—$CH_3$.

In still another embodiment, provided herein are compounds comprising Formula (III) and salts thereof:

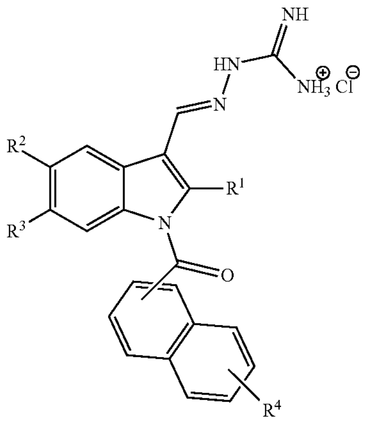

wherein $R^1$ is selected from the group consisting of hydrogen, deuterium, halogen, $CH_3$, Cl, Br, $COOC_2H_5$, OH, COOH, $COOCH_3$, $OCH_3$, OR', SR', NR'R', NR'COR', NR'CONR'R', NR'$CO_2$R', COR', $CO_2$R', NOR', $NO_2$, CONR'R', OC(O)NR'R', $SO_2$R', $SO_2$NR'R', NR'$SO_2$R', NR'$SO_2$NR'R', C(O)C(O)R', C(O)$CH_2$C(O)R', a substituted or unsubstituted $C_1$-$C_6$ alkyl, a substituted or unsubstituted $C_1$-$C_6$ alkenyl, a substituted or unsubstituted $C_1$-$C_6$ alkynyl, a substituted or unsubstituted aryl, and a substituted or unsubstituted heteroaryl; R' is independently selected from the group consisting of hydrogen, substituted $C_1$-$C_4$ aliphatic moiety, aliphatic moiety containing nitrogen, oxygen, or sulfur, or alternately, two R' moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur;

wherein $R^2$, $R^3$, and $R^4$ are independently selected from the group consisting of hydrogen, deuterium, halogen, $CH_3$, F, Cl, Br, $OCH_3$, OH, CN, $NH_2$, $CH_2OH$, $CH_2NH_2$, OCH2CH2N(CH2H5)2, $OCH_2CH_2N(CH_3)_2$, $CH_2OPO_3^{-2}$, $NHSO_2CH_3$, $CF_3$, $OCHF_2$, $OCH_2CH_2NH_2$, $COOC_2H_5$, COOH, $COOCH_3$,

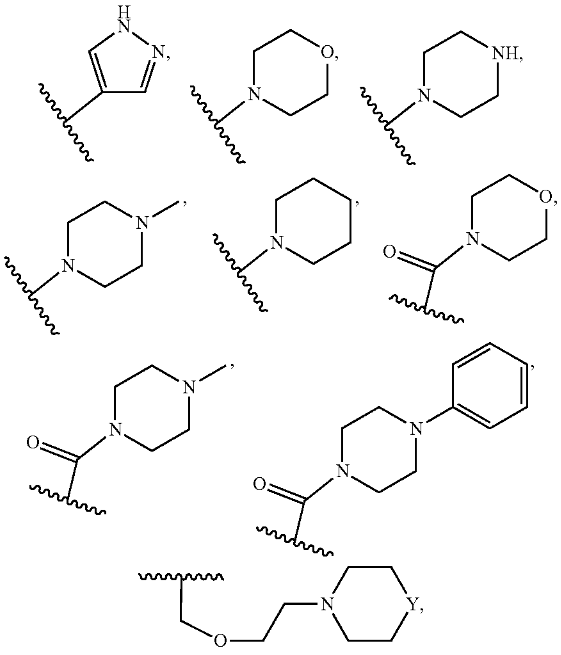

OR', SR', NR'R', NR'COR', NR'CONR'R', NR'$CO_2$R', COR', $CO_2$R', NOR', $NO_2$, CONR'R', OC(O)NR'R', $SO_2$R', $SO_2$NR'R', NR'$SO_2$R', NR'$SO_2$NR'R', C(O)C(O)R', C(O)$CH_2$C(O)R', a substituted or unsubstituted $C_1$-$C_6$ alkyl, a substituted or unsubstituted $C_1$-$C_6$ alkenyl, a substituted or unsubstituted $C_1$-$C_6$ alkynyl, a substituted or unsubstituted aryl, and a substituted or unsubstituted heteroaryl; R' is independently selected from the group consisting of hydrogen, substituted $C_1$-$C_4$ aliphatic moiety, aliphatic moiety containing nitrogen, oxygen, or sulfur, or alternately, two R' moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur: Y is independently selected from O, NH, or N—$CH_3$.

In still yet another embodiment, provided herein are compounds comprising Formula (IV) and salts thereof:

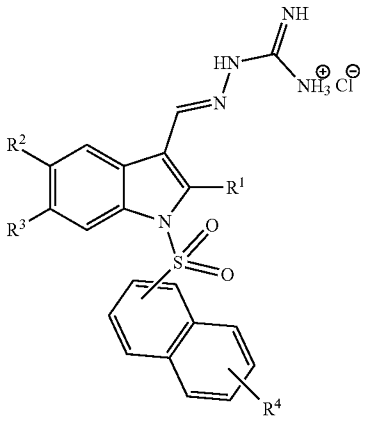

wherein $R^1$ is selected from the group consisting of hydrogen, deuterium, halogen, $CH_3$, Cl, Br, $COOC_2H_5$, OH, COOH, $COOCH_3$, $OCH_3$, OR', SR', NR'R', NR'COR', NR'CONR'R', $NR'CO_2R'$, COR', $CO_2R'$, NOR', $NO_2$, CONR'R', OC(O)NR'R', $SO_2R'$, $SO_2NR'R'$, $NR'SO_2R'$, $NR'SO_2NR'R'$, C(O)C(O)R', $C(O)CH_2C(O)R'$, a substituted or unsubstituted $C_1$-$C_6$ alkyl, a substituted or unsubstituted $C_1$-$C_6$ alkenyl, a substituted or unsubstituted $C_1$-$C_6$ alkynyl, a substituted or unsubstituted aryl, and a substituted or unsubstituted heteroaryl; R' is independently selected from the group consisting of hydrogen, substituted $C_1$-$C_4$ aliphatic moiety, aliphatic moiety containing nitrogen, oxygen, or sulfur, or alternately, two R' moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur;

wherein $R^2$, $R^3$, and $R^4$ are independently selected from the group consisting of hydrogen, deuterium, halogen, $CH_3$, F, Cl, Br, $OCH_3$, OH, CN, $NH_2$, $CH_2OH$, $CH_2NH_2$, OCH2CH2N(CH2H5)2, $OCH_2CH_2N(CH_3)_2$, $CH_2OPO_3^{-2}$, $NHSO_2CH_3$, $CF_3$, $OCHF_2$, $OCH_2CH_2NH_2$, $COOC_2H_5$, COOH, $COOCH_3$,

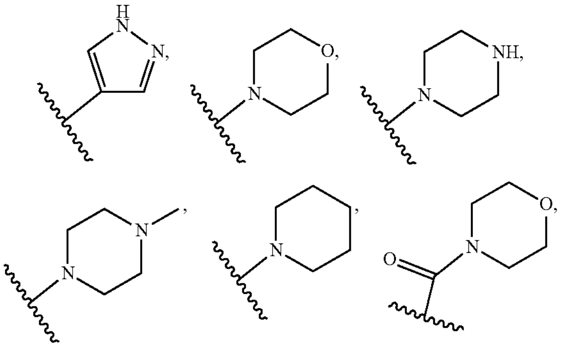

-continued

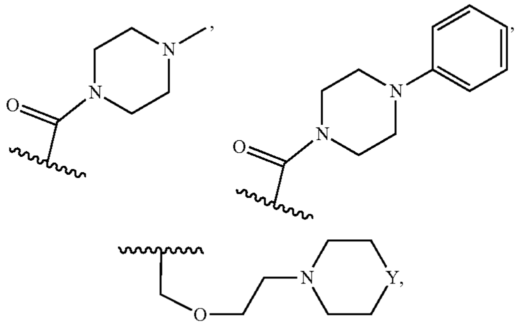

OR', SR', NR'R', NR'COR', NR'CONR'R', $NR'CO_2R'$, COR', $CO_2R'$, NOR', $NO_2$, CONR'R', OC(O)NR'R', $SO_2R'$, $SO_2NR'R'$, $NR'SO_2R'$, $NR'SO_2NR'R'$, C(O)C(O)R', $C(O)CH_2C(O)R'$, a substituted or unsubstituted $C_1$-$C_6$ alkyl, a substituted or unsubstituted $C_1$-$C_6$ alkenyl, a substituted or unsubstituted $C_1$-$C_6$ alkynyl, a substituted or unsubstituted aryl, and a substituted or unsubstituted heteroaryl; R' is independently selected from the group consisting of hydrogen, substituted $C_1$-$C_4$ aliphatic moiety, aliphatic moiety containing nitrogen, oxygen, or sulfur, or alternately, two R' moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur: Y is independently selected from O, NH, or N—$CH_3$.

In exemplary embodiments, a compound of the disclosure comprises formula (I), (II), (III), or (IV) as follows:

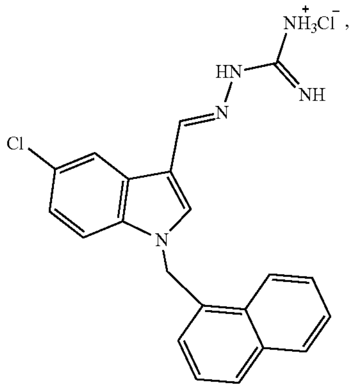

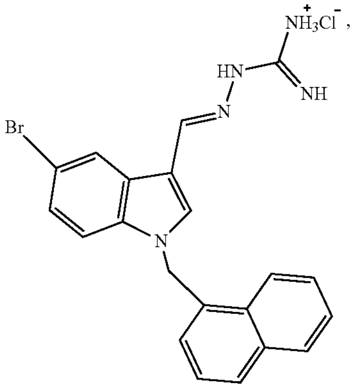

-continued

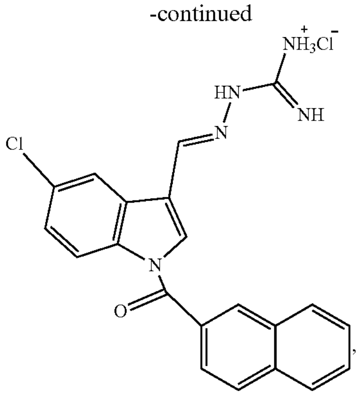

, or

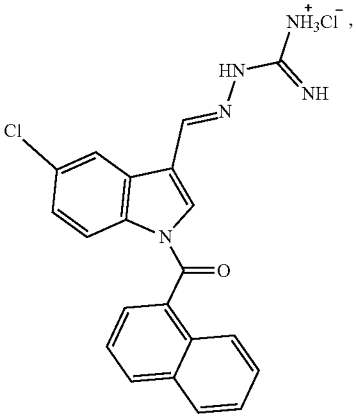

(b) Indole Barbituric Acid Compounds

In an embodiment, provided herein are compounds comprising Formula (V) and salts thereof:

Formula (V)

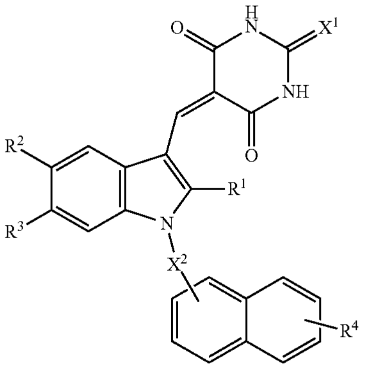

wherein $R^1$ is selected from the group consisting of hydrogen, deuterium, halogen, $CH_3$, Cl, Br, $COOC_2H_5$, OH, COOH, $COOCH_3$, $OCH_3$, OR', SR', NR'R', NR'COR', NR'CONR'R', $NR'CO_2R'$, COR', $CO_2R'$, NOR', $NO_2$, CONR'R', OC(O)NR'R', $SO_2R'$, $SO_2NR'R'$, $NR'SO_2R'$, $NR'SO_2NR'R'$, C(O)C(O)R', $C(O)CH_2C(O)R'$, a substituted or unsubstituted $C_1$-$C_6$ alkyl, a substituted or unsubstituted $C_1$-$C_6$ alkenyl, a substituted or unsubstituted $C_1$-$C_6$ alkynyl, a substituted or unsubstituted aryl, and a substituted or unsubstituted heteroaryl; R' is independently selected from the group consisting of hydrogen, substituted $C_1$-$C_4$ aliphatic moiety, aliphatic moiety containing nitrogen, oxygen, or sulfur, or alternately, two R' moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur;

wherein $R^2$, $R^3$, and $R^4$ are independently selected from the group consisting of hydrogen, deuterium, halogen, $CH_3$, F, Cl, Br, $OCH_3$, OH, CN, $NH_2$, $CH_2OH$, $CH_2NH_2$, OCH2CH2N(CH2H5)2, $OCH_2CH_2N(CH_3)_2$, $CH_2OPO_3^{-2}$, $NHSO_2CH_3$, $CF_3$, $OCHF_2$, $OCH_2CH_2NH_2$, $COOC_2H_5$, COOH, $COOCH_3$,

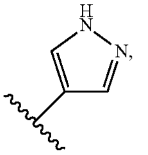 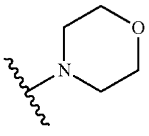, 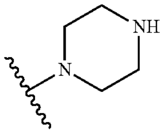,

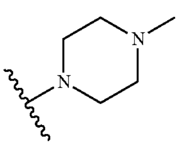, 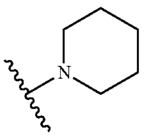, 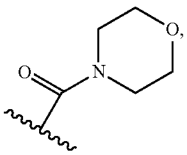

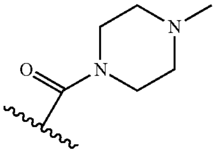, 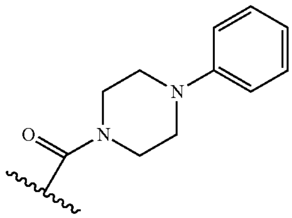,

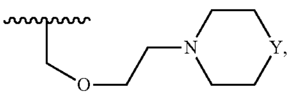

OR', SR', NR'R', NR'COR', NR'CONR'R', $NR'CO_2R'$, COR', $CO_2R'$, NOR', $NO_2$, CONR'R', OC(O)NR'R', $SO_2R'$, $SO_2NR'R'$, $NR'SO_2R'$, $NR'SO_2NR'R'$, C(O)C(O)R', $C(O)CH_2C(O)R'$, a substituted or unsubstituted $C_1$-$C_6$ alkyl, a substituted or unsubstituted $C_1$-$C_6$ alkenyl, a substituted or unsubstituted $C_1$-$C_6$ alkynyl, a substituted or unsubstituted aryl, and a substituted or unsubstituted heteroaryl; R' is independently selected from the group consisting of hydrogen, substituted $C_1$-$C_4$ aliphatic moiety, aliphatic moiety containing nitrogen, oxygen, or sulfur, or alternately, two R' moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur: Y is independently selected from O, NH, or N—$CH_3$;

wherein $X^1$ is O or S; and wherein $X^2$ is independently selected from $CH_2$, CO and $SO_2$.

In an embodiment, provided herein are compounds comprising Formula (VI) and salts thereof:

Formula (VI)

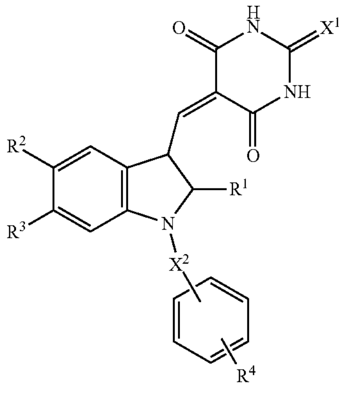

wherein $R^1$ is selected from the group consisting of hydrogen, deuterium, halogen, $CH_3$, Cl, Br, $COOC_2H_5$, OH, COOH, $COOCH_3$, $OCH_3$, OR', SR', NR'R', NR'COR', NR'CONR'R', NR'$CO_2$R', COR', $CO_2$R', NOR', $NO_2$, CONR'R', OC(O)NR'R', $SO_2$R', $SO_2$NR'R', NR'$SO_2$R', NR'$SO_2$NR'R', C(O)C(O)R', C(O)$CH_2$C(O)R', a substituted or unsubstituted $C_1$-$C_6$ alkyl, a substituted or unsubstituted $C_1$-$C_6$ alkenyl, a substituted or unsubstituted $C_1$-$C_6$ alkynyl, a substituted or unsubstituted aryl, and a substituted or unsubstituted heteroaryl; R' is independently selected from the group consisting of hydrogen, substituted $C_1$-$C_4$ aliphatic moiety, aliphatic moiety containing nitrogen, oxygen, or sulfur, or alternately, two R' moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur;

wherein $R^2$, $R^3$, and $R^4$ are independently selected from the group consisting of hydrogen, deuterium, halogen, $CH_3$, F, Cl, Br, $OCH_3$, OH, CN, $NH_2$, $CH_2OH$, $CH_2NH_2$, OCH2CH2N(CH2H5)2, $OCH_2CH_2N(CH_3)_2$, $CH_2OPO_3^{-2}$, $NHSO_2CH_3$, $CF_3$, $OCHF_2$, $OCH_2CH_2NH_2$, $COOC_2H_5$, COOH, $COOCH_3$,

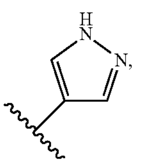 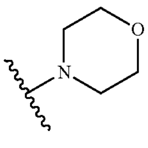 , 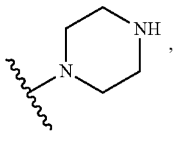 ,

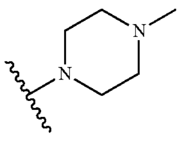 , 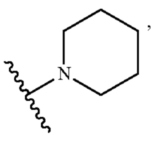 , 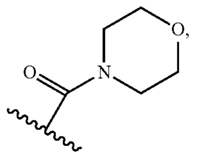

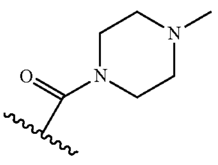 , 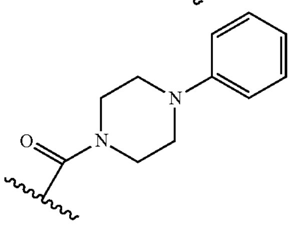 ,

-continued

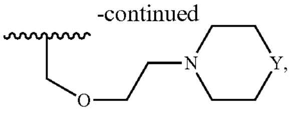

OR', SR', NR'R', NR'COR', NR'CONR'R', NR'$CO_2$R', COR', $CO_2$R', NOR', $NO_2$, CONR'R', OC(O)NR'R', $SO_2$R', $SO_2$NR'R', NR'$SO_2$R', NR'$SO_2$NR'R', C(O)C(O)R', C(O)$CH_2$C(O)R', a substituted or unsubstituted $C_1$-$C_6$ alkyl, a substituted or unsubstituted $C_1$-$C_6$ alkenyl, a substituted or unsubstituted $C_1$-$C_6$ alkynyl, a substituted or unsubstituted aryl, and a substituted or unsubstituted heteroaryl; R' is independently selected from the group consisting of hydrogen, substituted $C_1$-$C_4$ aliphatic moiety, aliphatic moiety containing nitrogen, oxygen, or sulfur, or alternately, two R' moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur: Y is independently selected from O, NH, or N—$CH_3$;

wherein $X^1$ is O or S; and wherein $X^2$ is independently selected from $CH_2$, CO and $SO_2$.

It is understood that the present disclosure encompasses a composition comprising an isomer of compound of Formula (I), (II), (III), (IV), (V) or (VI). The terms "isomer," "isomeric form," "stereochemically isomeric forms," or "stereoisomeric forms," as used herein, defines all possible isomeric as well as conformational forms, made up of the same atoms bonded by the same sequence of bonds but having different three-dimensional structures which are not interchangeable, which compounds or intermediates obtained during said process may possess. Unless otherwise mentioned or indicated, the chemical designation of a compound encompasses the mixture of all possible stereochemically isomeric forms which said compound may possess. Said mixture may contain all diastereoisomers, epimers, enantiomers, and/or conformers of the basic molecular structure of said compound. More in particular, stereogenic centers may have the R- or S-configuration, diastereoisomers may have a syn- or anti-configuration, substituents on bivalent cyclic saturated radicals may have either the cis- or trans-configuration and alkenyl radicals may have the E or Z-configuration. All stereochemically isomeric forms of said compound both in pure form or in admixture with each other are intended to be embraced within the scope of the present invention.

The compounds disclosed herein can exist as therapeutically acceptable salts. The present disclosure includes compounds listed above in the form of salts, including acid addition salts. Suitable salts include those: formed with both organic and inorganic acids. Such acid addition salts will normally be pharmaceutically acceptable. However, salts of non-pharmaceutically acceptable salts can be of utility in the preparation and purification of the compound in question. Basic addition salts can also be formed and be pharmaceutically acceptable. For more complete discussion of the preparation and selection of salts, refer to Pharmaceutical Salts: Properties, Selection, and Use (Stahl, P. Heinrich, Wiley VCHA, Zurich, Switzerland, 2002).

The term "therapeutically acceptable salt," as used herein represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate aspartate, benzoate, benzenesttlfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansullonate (isethionate), lactate, maleate, malonate, DL-mandelate, mesitylenesulfonate, methanesulfonate, naphthylenesulfonate, nicotinate, 2-naplithalenesultanate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quatemized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric,, and phosphoric, and organic acids such as oxalic, maleic, succinic, and citric. Salts can also be formed by coordination of the compounds with an alkali metal or alkaline earth ion. Hence, the present disclosure contemplates sodium, potassium, magnesium, and calcium salts of the compounds disclosed herein, and the like. Non-limiting examples of pharmaceutically acceptable salts of the above compounds include, inorganic acid salts such as hydrochloric acid, hydrobromic acid, nitric acid, sulphuric acid, and also organic acids such as oxalic acid, formic acid, fumaric acid, maleic acid, tartaric acid, citric acid, succinic acid.

Dosages of a compound of Formula (I), (II), (III), (IV), (V) or (VI) can vary between wide limits, depending upon the disease or disorder to be treated, the age and condition of the subject to be treated. In an embodiment where a composition comprising a compound of Formula (I), (II), (III), (IV), (V) or (VI) is contacted with a sample, the concentration of a compound of Formula (I), (II), (III), (IV), (V) or (VI) may be from about 1 μM to about 40 μM. Alternatively, the concentration of a compound of Formula (I), (II), (III), (IV), (V) or (VI) may be from about 5 μM to about 25 μM. For example, the concentration of a compound of Formula (I), (II), (III), (IV), (V) or (VI) may be about 1, about 2.5 about 5, about 6, about 7, about 8, about 9, about 10, about 11, about 12, about 13, about 14, about 15, about 16, about 17, about 18, about 19, about 20, about 21, about 22, about 23, about 24, about 25, about 30, about 35, or about 40 μM. Additionally, the concentration of a compound of Formula (I), (II), (III), (IV), (V) or (VI) may be greater than 40 μM. For example, the concentration of a compound of Formula (I), (II), (III), (IV), (V) or (VI) may be about 40, about 45, about 50, about 55, about 60, about 65, about 70, about 75, about 80, about 85, about 90, about 95, or about 100 μM.

In an embodiment where the composition comprising a compound of Formula (I), (II), (III), (IV), (V) or (VI) is administered to a subject, the dose of a compound of Formula (I), (II), (III), (IV), (V) or (VI) may be from about 0.1 mg/kg to about 500 mg/kg. For example, the dose of a compound of Formula (I), (II), (III), (IV), (V) or (VI) may be about 0.1 mg/kg, about 0.5 mg/kg, about 1 mg/kg, about 5 mg/kg, about 10 mg/kg, about 15 mg/kg, about 20 mg/kg, or about 25 mg/kg. Alternatively, the dose of a compound of Formula (I), (II), (III), (IV), (V) or (VI) may be about 25 mg/kg, about 50 mg/kg, about 75 mg/kg, about 100 mg/kg, about 125 mg/kg, about 150 mg/kg, about 175 mg/kg, about 200 mg/kg, about 225 mg/kg, or about 250 mg/kg. Additionally, the dose of a compound of Formula (I), (II), (III), (IV), (V) or (VI) may be about 300 mg/kg, about 325 mg/kg, about 350 mg/kg, about 375 mg/kg, about 400 mg/kg, about 425 mg/kg, about 450 mg/kg, about 475 mg/kg or about 500 mg/kg.

A composition of the invention may optionally comprise one or more additional drug or therapeutically active agent in addition to the compounds disclosed herein. In some embodiments, the additional drug or therapeutically active agent may be a genotoxic agent (e.g., a DNA-damaging agent or drug). As used herein "genotoxic therapy" refers to a treat of a tumor or cancer which utilizes the destructive properties of the treatment to induce DNA damage into tumor or cancer cells. The treatment is traditionally part of standardized regime. Any damage done to a tumor cancer is passed on to descendent cancer cells as proliferation continues. If this damage is severe enough, it will induce cells to undergo apoptosis. In non-limiting examples, a genotoxic therapy may include g-irradiation, alkylating agents such as nitrogen mustards (chlorambucil, cyclophosphamide, ifosfamide, melphalan), nitrosoureas (streptozocin, carmustine, lomustine), alkyl sulfonates (busulfan), triazines (dacarbazine, temozolomide) and ethylenimines (thiotepa, altretamine), platinum drugs such as cisplatin, carboplatin, oxalaplatin, antimetabolites such as 5-fluorouracil, 6-mercaptopurine, capecitabine, cladribine, clofarabine, cytarabine, floxuridine, fludarabine, gemcitabine, hydroxyurea, methotrexate, pemetrexed, pentostatin, thioguanine, anthracyclines such as daunorubicin, doxorubicin, epirubicin, idarubicin, anti-tumor antibiotics such as actinomycin-D, bleomycin, mitomycin-C, mitoxantrone, topoisomerase inhibitors such as topoisomerase I inhibitors (topotecan, irinotecan) and topoisomerase II inhibitors (etoposide, teniposide, mitoxantrone), mitotic inhibitors such as taxanes (paclitaxel, docetaxel), epothilones (ixabepilone), vinca alkaloids (vinblastine, vincristine, vinorelbine), and estramustine. In some embodiments, the additional active agent is a WEE1 inhibitor, such as AZD1775.

Dosages of an additional drug or therapeutically active agent can vary between wide limits, depending upon the disease or disorder to be treated, the age and condition of the subject to be treated. In an embodiment where the composition further comprising at least one additional drug or therapeutically active agent is contacted with a sample, the concentration of the at least one additional drug or therapeutically active agent may be from about 0.01 μM to about 10 μM. Alternatively, the concentration of the at least one additional drug or therapeutically active agent may be from about 0.01 μM to about 5 μM. For example, the concentration of the at least one additional drug or therapeutically active agent may be about 0.01, about 0.05, about 0.1, about 0.2, about 0.3, about 0.4, about 0.5, about 0.6, about 0.7, about 0.8, about 0.9, about 1, about 2, about 3, about 4, about 5, about 6, about 7, about 8, about 9, or about 10 μM. Additionally, the concentration of the at least one additional drug or therapeutically active agent be greater than 10 μM. For example, the concentration of the at least one additional senolytic agent may be about 10, about 15, about 20, about 25, about 30, about 35, about 40, about 45, about 50, about 55, about 60, about 65, about 70, about 75, about 80, about 85, about 90, about 95, or about 100 μM.

In an embodiment where the composition further comprising at least one additional drug or therapeutically active agent administered to a subject, the dose of the additional drug or therapeutically active agent may be from about 0.1 mg/kg to about 500 mg/kg. For example, the dose of the least one additional drug or therapeutically active agent may be about 0.1 mg/kg, about 0.5 mg/kg, about 1 mg/kg, about 5 mg/kg, about 10 mg/kg, about 15 mg/kg, about 20 mg/kg, or about 25 mg/kg. Alternatively, the dose of the least one additional drug or therapeutically active agent may be about 25 mg/kg, about 50 mg/kg, about 75 mg/kg, about 100 mg/kg, about 125 mg/kg, about 150 mg/kg, about 175 mg/kg, about 200 mg/kg, about 225 mg/kg, or about 250 mg/kg. Additionally, the dose of the least one additional drug or therapeutically active agent may be about 300 mg/kg, about 325 mg/kg, about 350 mg/kg, about 375 mg/kg, about 400 mg/kg, about 425 mg/kg, about 450 mg/kg, about 475 mg/kg, or about 500 mg/kg.

(c) Components of the Composition

The present disclosure also provides pharmaceutical compositions. The pharmaceutical composition comprises a compound of Formula (I), (II), (III), (IV), (V) or (VI), as an active ingredient, and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

(i) Diluent

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

(ii) Binder

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

(iii) Filler

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

(iv) Buffering Agent

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

(v) pH Modifier

In various embodiments, the excipient may be a pH modifier. By way of non-limiting example, the pH modifying agent may be sodium carbonate, sodium bicarbonate, sodium citrate, citric acid, or phosphoric acid.

(vi) Disintegrant

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

(vii) Dispersant

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

(viii) Excipient

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

(ix) Lubricant

In a further embodiment, the excipient may be a lubricant. Non-limiting examples of suitable lubricants include minerals such as talc or silica; and fats such as vegetable stearin, magnesium stearate, or stearic acid.

(x) Taste-Masking Agent

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

(xi) Flavoring Agent

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

(xii) Coloring Agent

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

(d) Administration (i) Dosage Forms

The composition can be formulated into various dosage forms and administered by a number of different means that will deliver a therapeutically effective amount of the active ingredient. Such compositions can be administered orally (e.g. inhalation), parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, intra-articular, or intrasternal injection, or infusion techniques. Formulation of drugs is discussed in, for example, Gennaro, A. R., Remington's Pharmaceutical Sciences, Mack Publishing Co., Easton, Pa. ($18^{th}$ ed, 1995), and Liberman, H. A. and Lachman, L., Eds., Pharmaceutical Dosage Forms, Marcel Dekker Inc., New York, N.Y. (1980). In a specific embodiment, a composition may be a food supplement or a composition may be a cosmetic.

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof. For administration by inhalation, the compounds are delivered in the form of an aerosol spray from pressured container or dispenser which contains a suitable propellant, e.g., a gas such as carbon dioxide, or a nebulizer.

For parenteral administration (including subcutaneous, intradermal, intravenous, intramuscular, intra-articular and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules, and tablets.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols, or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles, and mouth washes. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising a compound of Formula (I), (II), (III), or (IV) is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers, and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of a compound of Formula (I) in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, the compound of Formula (I), (II), (III), or (IV) may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying a compound of Formula (I), (II), (III), or (IV) may be prepared by any known method of preparing liposomes for drug delivery, such as, for example, detailed in U.S. Pat. Nos. 4,241,046; 4,394,448; 4,529,561; 4,755,388; 4,828,837; 4,925,661; 4,954,345; 4,957,735; 5,043,164; 5,064,655; 5,077,211; and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of the compound of Formula (I), (II), (III), or (IV), concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. The compound of Formula (I), (II), (III), (IV), (V) or (VI) may be encapsulated in a microemulsion by any method generally known in the art.

In yet another embodiment, a compound of Formula (I), (II), (III), (IV), (V) or (VI) may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

(II) Methods

The present disclosure provides compounds and pharmaceutical compositions which selectively target and inhibit DNA ploymerases. In some embodiments the DNA-polymerase is a translesion DNA synthesis polymerase. In a specific embodiment, the DNA polymerase is hpol κ. Thus, in some embodiments, the methods are useful in the treatment or prevention of disorders associated with cells that express hpol κ and include, but are not limited to cancer. The present disclosure encompasses a method of modulating DNA-polymerase kappa activity in a sample, the method comprising contacting a composition comprising an effective amount of a compound of Formula (I), a compound of Formula (II), a compound of Formula (III), a compound of Formula (IV), a compound of Formula (V), a compound of Formula (VI) or combinations thereof. In another aspect, the present disclosure encompasses a method of modulating DNA-polymerase kappa activity in a subject in need thereof, the method comprising administering to the subject a composition comprising a therapeutically effective amount of a compound of Formula (I), a compound of Formula (II), a compound of Formula (III), a compound of Formula (IV), a compound of Formula (V), a compound of Formula (VI) or combinations thereof. In yet another aspect, the present disclosure provides a composition comprising effective amount of a compound of Formula (I), a compound of Formula (II), a compound of Formula (III), a compound of Formula (IV), a compound of Formula (V), a compound of Formula (VI) or combinations thereof, for use in vitro, in vivo, or ex vivo. Suitable compositions for use in the methods of the present disclosure are disclosed herein, for instance those described in Section I.

In some embodiments, the present disclosure provides a method of inhibiting DNA polymerase activity, the method generally comprising contacting the DNA polymerase with a compound of Formula (I), a compound of Formula (II), a compound of Formula (III), a compound of Formula (IV), a compound of Formula (V), a compound of Formula (VI) or combinations thereof, under condition sufficient for the compound to bind to the DNA polymerase. In one aspect the DNA polymerase is hpol κ. In certain embodiments, the DNA pol activity is inhibited in a cell. In some embodiments, the cell is in a subject. In some aspects, DNA polymerase activity as used herein refers to the ability of the DNA polymerase to bind DNA. In other aspects, DNA polymerase activity refers to the ability of the polymerase to synthesize DNA.

In some aspects, the compounds of the disclosure inhibit DNA polymerase activity by specifically binding to the DNA polymerase. In some embodiments, a compound of the disclosure disrupts the N-clasp, finger, and/or little finger domains of the DNA polymerase which guide and hold template DNA residues in the pol active site.

In some embodiments, the compounds and pharmaceutical compositions of the present disclosure can be useful in the treatment or prevention of a tumor or cancer.

In certain embodiments, the cancer can be chosen from adenocarcinoma, adult T-cell leukemia/lymphoma, bladder cancer, blastoma, bone cancer, breast cancer, brain cancer, carcinoma, myeloid sarcoma, cervical cancer, colorectal cancer, esophageal cancer, gastrointestinal cancer, glioblastoma multiforme, glioma, gallbladder cancer, gastric cancer, head and neck cancer, Hodgkin's lymphoma, Non-Hodgkin's lymphoma, intestinal cancer, kidney cancer, laryngeal cancer, leukemia, lung cancer, lymphoma, liver cancer, small cell lung cancer, non-small cell lung cancer, mesothelioma, multiple myeloma, ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, synovial sarcoma, T-cell lymphoma, testicular cancer, thyroid cancer, throat cancer, urogenital cancer, urothelial carcinoma uterine cancer, vaginal cancer, or Wilms' tumor.

In particular, embodiments, the cancer can be a glioma, In particular embodiments, the cancer can be glioblastoma multiforme.

In some embodiments, the tumor or cancer cell has increased activation of an aryl hydrocarbon receptor (AhR). The aryl hydrocarbon receptor (AhR or AHR or ahr or ahR) is a protein that in humans is encoded by the AHR gene. The aryl hydrocarbon receptor is a transcription factor that regulates gene expression. It was originally thought to function primarily as a sensor of xenobiotic chemicals and also as the regulator of enzymes such as cytochrome P450s that metabolize these chemicals. The most notable of these xenobiotic chemicals are aromatic (aryl) hydrocarbons from which the receptor derives its name. Activation of the kynurenine pathway (KP) has been shown to lead to increased hpol κ expression in cancer cells through the action of the aryl hydrocarbon receptor (AhR). Aberrant activation of the KP exerts a multifaceted effect on cancer phenotypes that includes suppression of antitumor immune response and the promotion of malignancy, at least in part, through activation of the AhR.

In some embodiments, the tumor or cancer cell has modulated expression of a DNA polymerase. In certain aspects, the tumor or cancer cell overexpresses hpol κ. In some embodiments, hpol κ expression is compared to normal tissues. In other embodiments, hpol κ expression is compared to a tumor or cancer cell in obtained from the same or another subject.

In some embodiments, the methods of the present disclosure provide a method to inhibit a tumor stem cell or cancer stem cell growth or differentiation. Cancer stem cells (CSCs) are cancer cells (found within tumors or hematological cancers) that possess characteristics associated with normal stem cells, specifically the ability to give rise to all cell types found in a particular cancer sample. CSCs are therefore tumorigenic (tumor-forming), perhaps in contrast to other non-tumorigenic cancer cells. CSCs may generate tumors through the stem cell processes of self-renewal and differentiation into multiple cell types. Such cells are hypothesized to persist in tumors as a distinct population and cause relapse and metastasis by giving rise to new tumors. In certain aspects, the cancer stem cell is a glioblastoma stem cell.

In some embodiments, the present disclosure provides a methods for treating tumors or cancer cells which are resistant to standard genotoxic agents, the method generally comprising administering a compound of Formula (I), a compound of Formula (II), a compound of Formula (III), a compound of Formula (IV), a compound of Formula (V), a compound of Formula (VI) or combinations thereof. In some embodiments, a compound of the disclosure is administered as an adjuvant to a genotoxic therapy. Therefore, the present disclosure provides methods of treating a tumor or cancer cell comprising administering a compound of the disclosure and a genotoxic therapy. In non-limiting examples, a genotoxic therapy to which the tumor cell or cancer cell is resistant may include γ-irradiation, alkylating agents such as nitrogen mustards (chlorambucil, cyclophosphamide, ifosfamide, melphalan), nitrosoureas (streptozocin, carmustine, lomustine), alkyl sulfonates (busulfan), triazines (dacarbazine, temozolomide) and ethylenimines (thiotepa, altretamine), platinum drugs such as cisplatin, carboplatin, oxalaplatin, antimetabolites such as 5-fluorouracil, 6-mercaptopurine, capecitabine, cladribine, clofarabine, cytarabine, floxuridine, fludarabine, gemcitabine, hydroxyurea, methotrexate, pemetrexed, pentostatin, thioguanine, anthracyclines such as daunorubicin, doxorubicin, epirubicin, idarubicin, anti-tumor antibiotics such as actinomycin-D, bleomycin, mitomycin-C, mitoxantrone, topoisomerase inhibitors such as topoisomerase I inhibitors (topotecan, irinotecan) and topoisomerase II inhibitors (etoposide, teniposide, mitoxantrone), mitotic inhibitors such as taxanes (paclitaxel, docetaxel), epothilones (ixabepilone), *vinca* alkaloids (vinblastine, vincristine, vinorelbine), and estramustine. In some embodiments, the resistant tumor or cancer cells are treated by administering a compound of the disclosure in combination which a genotoxic agent. When a compound of the disclosure is administered which an additional active agent the administration of the additional agent may be sequentially or simultaneously. When administered sequentially the additional agent may be administered before or after the compound of the disclosure.

In preferred aspects, a method of the disclosure is used to treat a neoplasm or cancer. The neoplasm may be malignant or benign, the cancer may be primary or metastatic; the neoplasm or cancer may be early stage or late stage. A cancer or a neoplasm may be treated by delivering a compound of the disclosure to at least one neoplasm or cancer cell in a subject. The cancer or neoplasm may be treated by slowing cancer cell growth or killing cancer cells.

In some aspects, a compound of the disclosure of may treat a cancer or a neoplasm by inhibiting DNA polymerase function in a neoplasm or cancer cell in a subject in vivo. Non-limiting examples of neoplasms or cancers that may be treated with a method of the invention may include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas), breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sézary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-cell lymphoma (cutaneous), T-cell leukemia and lymphoma, testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), unknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, or Wilms tumor (childhood).

In certain aspects, a therapeutically effective amount of a composition of the invention may be administered to a subject. Administration is performed using standard effective techniques, including peripherally (i.e. not by administration into the central nervous system) or locally to the central nervous system. Peripheral administration includes but is not limited to oral, inhalation, intravenous, intraperitoneal, intra-articular, subcutaneous, pulmonary, transdermal, intramuscular, intranasal, buccal, sublingual, or suppository administration. Local administration, including directly into the central nervous system (CNS) includes but is not limited to via a lumbar, intraventricular or intraparenchymal catheter or using a surgically implanted controlled release formulation. The route of administration may be dictated by the disease or condition to be treated.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents, and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners.

For therapeutic applications, a therapeutically effective amount of a composition of the invention is administered to a subject. A "therapeutically effective amount" is an amount of the therapeutic composition sufficient to produce a measurable response (e.g., cell death, or an improvement in symptoms associated with a DNA-polymerase kappa disease). Actual dosage levels of active ingredients in a therapeutic composition of the invention can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, age, the disease or condition, the function-decreasing disorder, the symptoms, and the physical condition and prior medical history of the subject being treated. In some embodiments, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine.

The frequency of dosing may be daily or once, twice, three times, or more per week or per month, as needed as to effectively treat the symptoms. The timing of administration of the treatment relative to the disease itself and duration of treatment will be determined by the circumstances surrounding the case. Treatment could begin immediately, such as at the site of the injury as administered by emergency medical personnel. Treatment could begin in a hospital or clinic itself, or at a later time after discharge from the hospital or after being seen in an outpatient clinic. Duration of treatment could range from a single dose administered on a one-time basis to a life-long course of therapeutic treatments.

Typical dosage levels can be determined and optimized using standard clinical techniques and will be dependent on the mode of administration.

A subject may be a rodent, a human, a livestock animal, a companion animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In still another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a preferred embodiment, the subject is a human.

III. Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to a compound of Formula (I), a compound of Formula (II), a compound of Formula (III), a compound of Formula (IV), a compound of Formula (V), a compound of Formula (VI) or combinations thereof. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

When introducing elements of the present disclosure or the preferred aspects(s) thereof, the articles "a," "an," "the," and "said" are intended to mean that there are one or more of the elements. The terms "comprising," "including," and "having" are intended to be inclusive and mean that there may be additional elements other than the listed elements.

As used herein, the following definitions shall apply unless otherwise indicated. For purposes of this invention, the chemical elements are identified in accordance with the Periodic Table of the Elements, CAS version, and the Handbook of Chemistry and Physics, $75^{th}$ Ed. 1994. Additionally, general principles of organic chemistry are described in "Organic Chemistry," Thomas Sorrell, University Science Books, Sausalito: 1999, and "March's Advanced Organic Chemistry," $5^{th}$ Ed., Smith, M. B. and March, J., eds. John Wiley & Sons, New York: 2001, the entire contents of which are hereby incorporated by reference.

The term "alkyl" as used herein alone or as part of a group refers to saturated monovalent hydrocarbon radicals having straight or branched hydrocarbon chains or, in the event that at least 3 carbon atoms are present, cyclic hydrocarbons or combinations thereof and contains 1 to 20 carbon atoms (C.sub.1-20alkyl), suitably 1 to 10 carbon atoms (C.sub.1-10alkyl), preferably 1 to 8 carbon atoms (C.sub.1-8alkyl), more preferably 1 to 6 carbon atoms (C.sub.1-4alkyl), and even more preferably 1 to 4 carbon atoms (C.sub.1-4alkyl). Examples of alkyl radicals include methyl, ethyl, propyl, isopropyl, n-butyl, isobutyl, sec-butyl, tert-butyl, pentyl, isoamyl, hexyl, cyclopropyl, cyclobutyl, cyclopentyl, cyclohexyl, and the like.

The term "alkenyl" as used herein alone or as part of a group refers to monovalent hydrocarbon radicals having a straight or branched hydrocarbon chains having one or more double bonds and containing from 2 to about 18 carbon atoms, preferably from 2 to about 8 carbon atoms, more preferably from 2 to about 5 carbon atoms. Examples of suitable alkenyl radicals include ethenyl, propenyl, alkyl, 1,4-butadienyl, and the like.

The term "alkynyl" as used herein alone or as part of a group refers to monovalent hydrocarbon radicals having a straight or branched hydrocarbon chains having one or more triple bonds and containing from 2 to about 10 carbon atoms, more preferably from 2 to about 5 carbon atoms. Examples of alkynyl radicals include ethynyl, propynyl, (propargyl), butyny, I and the like.

The term "aryl" as used herein, alone or as part of a group, includes an organic radical derived from an aromatic hydrocarbon by removal of one hydrogen, and includes monocyclic and polycyclic radicals, such as phenyl, biphenyl, naphthyl.

The term "alkoxy" as used herein, alone or as part of a group, refers to an alkyl ether radical wherein the term alkyl is as defined above. Examples of alkyl ether radical include methoxy, ethoxy, n-propoxy, isopropoxy, n-butoxy, isobutoxy, sec-butoxy, tert-butoxy, and the like.

The term "cycloalkyl" as used herein, alone or in combination, means a saturated or partially saturated monocyclic, bicyclic or tricyclic alkyl radical wherein each cyclic moiety contains from about 3 to about 8 carbon atoms, more preferably from about 3 to about 6 carbon atoms. Examples of such cycloalkyl radicals include cyclopropyl, cyclobutyl, cyclopentyl, cyclohexyl, and the like.

The term "cycloalkylalkyl" as used herein, alone or in combination, means an alkyl radical as defined above which is substituted by a cycloalkyl radical as defined above. Examples of such cycloalkylalkyl radicals include cyclopropylmethyl, cyclobutyl-methyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, cyclohexylbutyl, and the like.

The term "substituted" as used herein means that one or more of the hydrogen atoms bonded to carbon atoms in the chain or ring have been replaced with other substituents. Suitable substituents include monovalent hydrocarbon groups including alkyl groups such as methyl groups and monovalent heterogeneous groups including alkoxy groups such as methoxy groups.

The term "unsubstituted" as used herein means that the carbon chain or ring contains no other substituents other than carbon and hydrogen.

The term "branched" as used herein means that the carbon chain is not simply a linear chain. "Unbranched" means that the carbon chain is a linear carbon chain.

The term "saturated" as used herein means that the carbon chain or ring does not contain any double or triple bonds. "Unsaturated" means that the carbon chain or ring contains at least one double bond. An unsaturated carbon chain or ring may include more than one double bond.

The term "hydrocarbon group" means a chain of 1 to 25 carbon atoms, suitably 1 to 12 carbon atoms, more suitably 1 to 10 carbon atoms, and most suitably 1 to 8 carbon atoms. Hydrocarbon groups may have a linear or branched chain structure. Suitably the hydrocarbon groups have one branch.

The term "carbocyclic group" means a saturated or unsaturated hydrocarbon ring. Carbocyclic groups are not aromatic. Carbocyclic groups are monocyclic or polycyclic. Polycyclic carbocyclic groups can be fused, spiro, or bridged ring systems. Monocyclic carbocyclic groups contain 4 to 10 carbon atoms, suitably 4 to 7 carbon atoms, and more suitably 5 to 6 carbon atoms in the ring. Bicyclic carbocyclic groups contain 8 to 12 carbon atoms, preferably 9 to 10 carbon atoms in the rings.

The term "heteroatom" means an atom other than carbon e.g., in the ring of a heterocyclic group or the chain of a heterogeneous group. Preferably, heteroatoms are selected from the group consisting of sulfur, phosphorous, nitrogen and oxygen atoms. Groups containing more than one heteroatom may contain different heteroatoms.

The term "heterocyclic group" means a saturated or unsaturated ring structure containing carbon atoms and 1 or more heteroatoms in the ring. Heterocyclic groups are not aromatic. Heterocyclic groups are monocyclic or polycyclic. Polycyclic heteroaromatic groups can be fused, spiro, or bridged ring systems. Monocyclic heterocyclic groups contain 4 to 10 member atoms (i.e., including both carbon atoms and at least 1 heteroatom), suitably 4 to 7, and more suitably 5 to 6 in the ring. Bicyclic heterocyclic groups contain 8 to 18 member atoms, suitably 9 or 10 in the rings.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as Molecular Cloning: A Laboratory Manual, second edition (Sambrook, et al., 1989) Cold Spring Harbor Press; Oligonucleotide Synthesis (M. J. Gait, ed. 1984); Methods in Molecular Biology, Humana Press; Cell Biology: A Laboratory Notebook (J. E. Cellis, ed., 1989) Academic Press; Animal Cell Culture (R. I. Freshney, ed. 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); DNA Cloning: A practical Approach, Volumes I and II (D. N. Glover ed. 1985); Nucleic Acid Hybridization (B. D. Hames & S. J. Higgins eds. (1985»; Transcription and Translation (B. D. Hames & S. J. Higgins, eds. (1984»; Animal Cell Culture (R.I. Freshney, ed. (1986»; Immobilized Cells and Enzymes (IRL Press, (1986»; and B. Perbal, A practical Guide To Molecular Cloning (1984); F. M. Ausubel et al. (eds.).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Synthesis of Indole-Derived Compounds

A series of indoleaminoguanidine (IAG) analogs were synthesized by the reaction of an appropriate aryl aldehyde (1.25 equivalents) with aminoguanidine hydrochloride (1.0 equivalent). These reactants were dissolved in a minimal amount of methanol, and the solution heated to reflux and then stirred for a period of 4-6 hours. After completion of the reaction the alcohol was removed by concentration under reduced pressure, and the residue obtained was triturated in dichloromethane for 15 minutes to obtain a solid. This solid was then filtered, washed with dichloromethane or chloroform and dried under reduced pressure to remove any remaining solvent (see, e.g., Scheme1, Scheme 2). The structure and purity of these products were verified by $^1$H and $^{13}$C-NMR spectroscopy.

Scheme 1.
Synthesis of ((E)-2-((1-(1-naphthoyl or 1-naphthalenylmethyl or (naphthalen-1-yl-sulfonyl))-1H-indol-3-yl)methylene)hydrazine-1-carboximidamide hydrochlorides

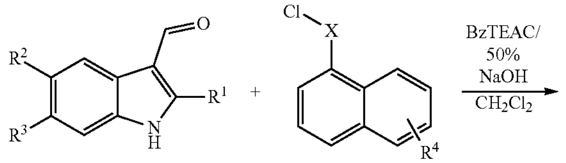

X = $CH_2$, CO, $SO_2$,
$R^1$ = H, $CH_3$, Cl, Br, $COOC_2H_5$, OH, COOH, $COOCH_3$
$R^2$ = $R^3$ = $R^4$ = H, $CH_3$, F, Cl, Br, $OCH_3$, OH, CN, $NH_2$, $CH_2$—OH, $CH_2NH_2$—O—$CH_2$—N—$(C_2H_5)_2$; —O—$CH_2$—$CH_2$—N—$(CH_2)_2$, $CH_2$—O—$PO_3^{-2}$, NH—$SO_2$—$CH_3$, $CF_3$, $OCHF_2$, —O—$CH_2$—$CH_2$—$NH_2$.

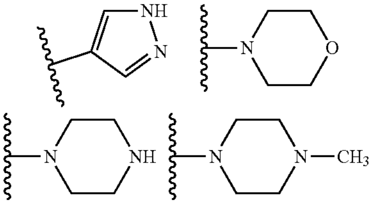

-continued

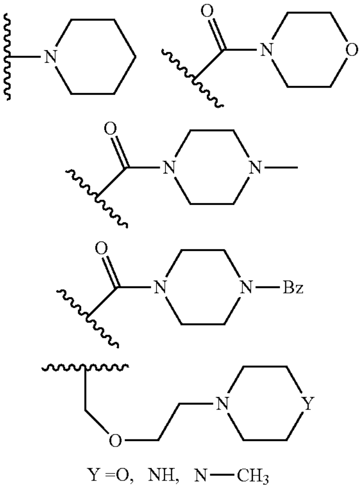

Y =O, NH, N—$CH_3$

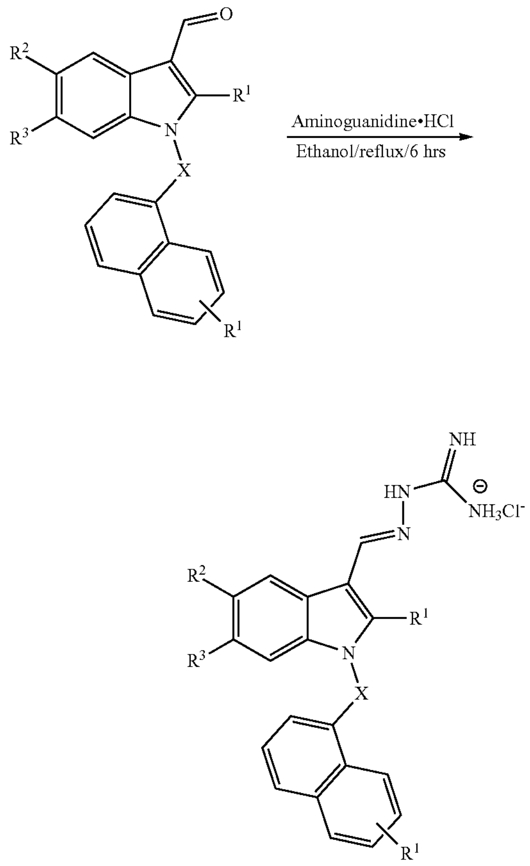

X = CO; $R^1$ = $R^3$ = $R^4$ = H, $R^2$ = Cl
X = $CH_2$; $R^1$ = $R^3$ = $R^4$ = H, $R^2$ = Cl
X = $CH_2$; $R^2$ = $OCH_3$, $R^3$ = $R^4$ = H, $R^1$ = $CH_3$
X = CO; $R^1$ = $R^3$ = $R^4$ = H, $R^2$ = $OCH_3$
X = $CH_2$; $R^1$ = $R^2$ = $R^3$ = $R^4$ = H
X = $CH_2$; $R^1$ = $R^3$ = $R^4$ = H, $R^2$ = Br
X = $CH_2$; $R^1$ = $R^3$ = $R^4$ = H, $R^2$ = $OCH_3$
X = CO; $R^2$ = $R^3$ = $R^4$ = H, $R^2$ = $CH_3$

Scheme 2. Synthesis of ((E)-2-((1-(2-naphthoyl or 2-naphthalenylmethyl or (naphthalen-2-ylsulfonyl))-1H-indol-3-yl)methylene)hydrazine-1-carboximidamide hydrochlorides

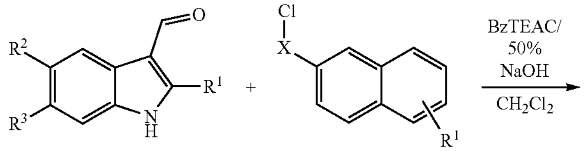

X = $CH_2$, CO, $SO_2$,
$R^1$ = H, $CH_3$, Cl, Br, $COOC_2H_5$, OH, COOH, $COOCH_3$,
$R^2 = R^3 = R^4$ = H, $CH_3$, F, Cl, Br, $OCH_3$, OH, CN, $NH_2$,
$CH_2$—OH, $CH_2NH_2$,—O—$CH_2$—$CH_2$—N—$(CH_3)_2$,
$CH_2$—O—$PO_3^{-2}$, NH—$SO_2$—$CH_3$, $CF_3$, $OCHF_2$,
—O—$CH_2$—$CH_2$—$NH_2$.

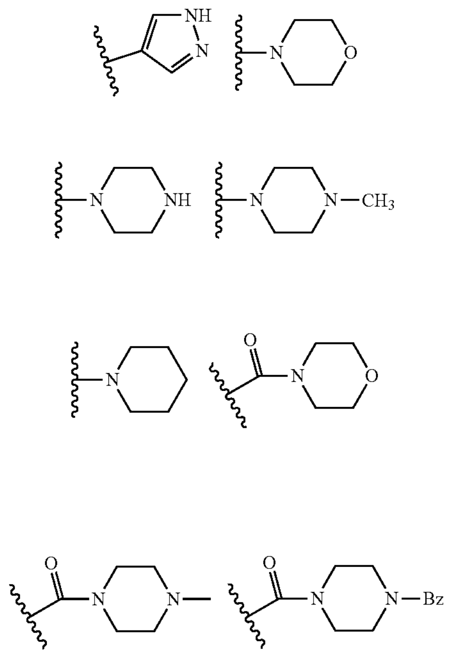

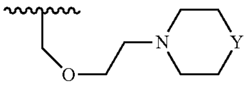

Y = O, NH, N—$CH_3$

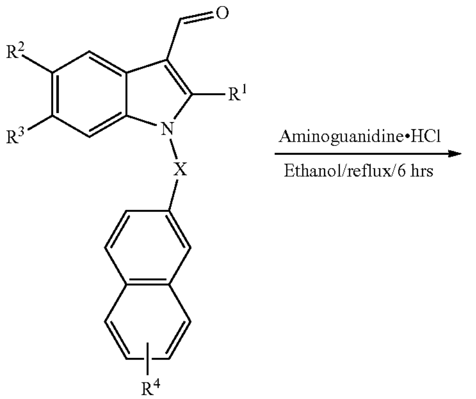

-continued

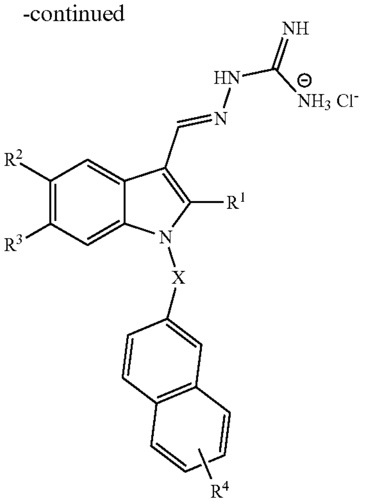

X = CO; $R^1 = R^3 = R^4$ = H, $R^2$ = Cl
X = $CH_2$; $R^1 = R^3 = R^4$ = H, $R^2$ = Cl
X = $CH_2$; $R^1 = R^3 = R^4$ = H, $R^2$ = Cl
X = $CH_2$; $R^1 = R^3 = R^4$ = H, $R^2$ = $OCH_3$
X = $CH_2$; $R^1 = R^2 = R^3 = R^4$ = H

Example 2: Inhibition of Human DNA Polymerases with Indole-Derived Molecules

The goal of this study was to investigate molecules comprising an indole scaffold as translesion DNA synthesis polymerases (TLS pols) inhibitors, which could prove useful as a strategy for improving cancer patient response to genotoxic drugs. The ability of tumor cells to bypass DNA damage inflicted by cancer therapeutics is one mechanism that promotes resistance to these drugs. Central to this process are the socalled TLS pols, and included among these nonessential enzymes is human pol kappa (hpol κ). In evolutionary terms, hpol κ is considered to be a homologue of bacterial pol IV encoded by the dinB gene in *Escherichia coli*. A number of studies have highlighted a role for hpol κ in tolerating bulky DNA adducts such as those induced following bioactivation of polycyclic aromatic hydrocarbons (PAHs). Animals and cells lacking pol κ exhibit sensitivity to other sources of DNA damage such as UV light, mitomycin C (MMC), and conditions that promote oxidative stress. There also appears to be a role for pol κ in the maintenance of endogenous barriers to replication, including AT-rich microsatellites, common fragile sites, and G-rich quadruplex forming motifs. Emerging evidence supports the idea that hpol κ may also serve as a means of resolving replication intermediates by protecting regressed forks and by activating the replication stress response (RSR) by synthesizing short DNA primers near stalled forks, which then facilitate recruitment of proteins and enzymes involved in signaling through the ATR kinase. Other studies have implicated misregulation of hpol κ in the etiology of cancer.

In 2010, overexpression of hpol κ in glioblastoma patients was reported to be an independent prognostic indicator of shorter survival. A follow-up to that study revealed that hpol κ expression promotes resistance to temozolomide (TMZ), an alkylating agent often used to treat aggressive brain tumors. The mechanism of hpol κ-mediated resistance to TMZ involved activation of ATR/Chk I signaling to stimulate resolution of replication stress and homologous recombination mediated repair of alkylation-induced DNA damage. Yet, the mechanisms driving overexpression of hpol κ in glioblastoma remained unknown.

Building off these reports, work from the inventors found that activation of the kynurenine pathway (KP) increased hpol κ expression in glioblastoma-derived cells through the action of the aryl hydrocarbon receptor (AhR). Aberrant activation of the KP occurs in glioblastoma and exerts a multifaceted effect on cancer phenotypes that includes suppression of antitumor immune response and the promotion of malignancy, at least in part, through activation of the AhR. Pioneering work from the laboratory of Dr. Haruo Ohmori established a regulatory link between AhR activation and upregulation of pol expression in a murine model. Experiments in rats also support a role for the AhR in regulation of pol κ. Subsequent work helped elucidate a crucial role for hpol κ in the tolerance of DNA damage induced by AhR ligands such as benzo[a]-pyrene (B[a]P). Thus, a picture begins to emerge, painting hpol κ as having evolved to promote tolerance of bioactivated AhR ligands with some aspect of this pathway contributing to glioblastoma biology. Additional studies have illustrated that upregulation of hpol κ can have a detrimental effect on genome stability, including disruption of fork dynamics, aberrant stimulation of homologous recombination, increased micronuclei formation, and aneuploidy, supporting the notion that overexpression of hpol κ can have a detrimental impact on genome stability. However, it is clear that the relationships among pol κ, tolerance of replication stress, and genome stability involve multiple variables and are not simple affairs, as demonstrated by the fact that pol κ protects stalled forks from degradation and helps resolve DNA replication intermediates in cells that have CDK2 activity artificially induced. Despite the double-edged nature of pol κ action, it is generally accepted that pol κ inhibition might help improve the anticancer activity of genotoxic therapies.

As efforts to develop targeted cancer therapeutics progress, several groups have sought to identify inhibitors of DNA damage tolerance as a way of improving existing treatments. A number of studies have identified small-molecule TLS pol inhibitors, and new strategies include targeting mechanisms that promote TLS pol recruitment to sites of replication stress/DNA damage. Previous work lead to the identification of candesartan cilexetil and MK-886 as inhibitors of the Y-family members. The inhibitory actions of indole barbituric/thiobarbituric acid (IBA) derivatives against hpol η have also been reported. Although MK-886 seemed to exhibit some specificity for hpol ι and the IBA derivatives inhibited hpol η with modest specificity, it was difficult to identify a compound that selectively inhibits hpol κ over the other Y-family members. Most recently, work from the inventors synthesized a compound that inhibits hpol η with a low micromolar $IC_{50}$ value and acts synergistically to potentiate the cytotoxic effects of cisplatin in a target-dependent manner.

In the present example overcomes the barrier to specificity for hpol κ. Remarkably, the novel indole aminoguanidine (IAG) scaffold reported here acts through a mechanism that is distinct from IBA derivatives and appears to disrupt the interaction between the N-clasp, which is unique to hpol κ, and the core Y-family pol structure to inhibit TLS action. In addition, the target-dependent potentiation of TMZ, a standard-of-care treatment for glioblastoma is reported.

Methods

Reagents

All chemicals were of molecular biology grade or higher. Only ultrapure $H_2O$ was used. The novel IAG compounds tested for inhibitory properties against the DNA polymerases were synthesized utilizing previously published procedures (Ring, J. R., et. al., Bioorg. Med. Chem. 21, (2013) pp 1764-1774). TMZ was purchased from Millipore Sigma (Burlington, MA). TMZ is an alkylating agent used in the treatment of cancer.

Protein Expression and Purification

Bacterial overexpression and purification of the core polymerase domain of Y-family members hpol κ (residues 19-526), hpol η (residues 1-437), hpol ι (residues 1-446), and hRevl (residues 330-833) have been described previously. Similarly, the expression and purification for representative members of the B-family (pol Dpol from *Sulfolobus solfataricus*) and A-family (DNA pol I from *Mycobacterium tuberculosis*) have been previously described. Purified human DNA pol beta (hpol β) was a kind gift from Dr. Samuel Wilson (NIEHS). The purified catalytic core of human DNA pol lambda (hpol λ, residues 1-325) was a kind gift from Dr. Miguel Garcia-Diaz (Stony Brook University). Both hpol β and hpol λ served as representative members from the X-family of polymerases.

Fluorescence-Based Assay to Screen for Inhibition of DNA Polymerase Activity 53 compounds, based on indole-barbituric acid (IBA) and indole-aminoguanidine (IAG) chemical scaffolds, were evaluated for inhibition of polymerase activity of hpol κ and the other polymerases described above, using an assay monitoring fluorescence of a 5-carboxytetramethylrhodamine (TAMRA) labeled oligonucleotide. The DNA substrate was prepared as described previously. Briefly, a TAMRA-labeled reporter (or displaced) strand (5'-TTT TTT TTG C-TAMRA-3') (SEQ ID NO: 58) and unlabeled primer strand (5'-TCA CCC TCG TAC GAC TCT T-3') (SEQ ID NO: 59) were annealed to a Black Hole Quencher (BHQ)-labeled template strand (5'-BHQ2-GCA AAA AAAAAA GAG TCG TAC GAG GGT GA-3') (SEQ ID NO: 60) in a solution containing 10 mM Tris (pH 8.0), 50 mM NaCl, 2 mM $MgCl_2$, and $H_2O$. The template (T), primer (P) and displaced strand (D) oligonucleotides were mixed in a 1:1.5:1.5 (T:P:D) molar ratio for annealing. After an incubation period of three minutes at 95° C., the DNA was allowed to slowly cool to room temperature overnight. The assay was used to screen 53 compounds for inhibition of hpol κ activity (Tables 1 and 2).

TABLE 1
Chemical structures of IBA-derived compounds and hpol κ activity in the presence of each compound.[a]
| Compound | | Chemical | % Activity | |
|---|---|---|---|---|
| Number | I. D. | Structure | Mean | S. D. |
| 1 | IBA-1 | 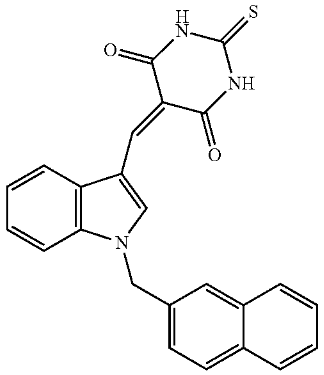 [SMILES: O=C1NC(=S)NC(=O)C1=Cc1cn(Cc2ccc3ccccc3c2)c2ccccc12] | 116.2 | 11.1 |
| 2 | IBA-2 | 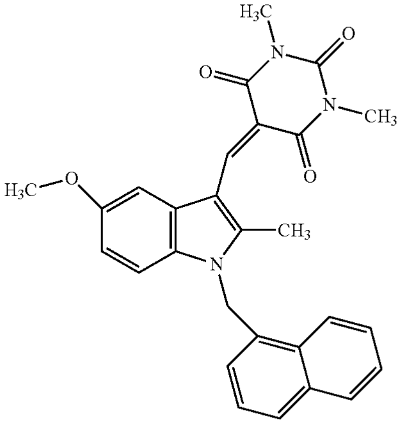 [SMILES: COc1ccc2c(c1)c(C=C1C(=O)N(C)C(=O)N(C)C1=O)c(C)n2Cc1cccc2ccccc12] | 113.8 | 11.5 |
| 3 | IBA-3 | 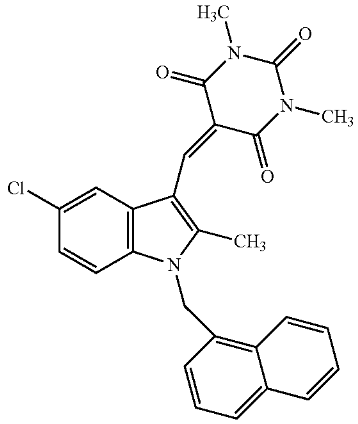 [SMILES: Cc1c(C=C2C(=O)N(C)C(=O)N(C)C2=O)c2cc(Cl)ccc2n1Cc1cccc2ccccc12] | 111.0 | 7.3 |

TABLE 1-continued
| Number | Compound I. D. | Chemical Structure | % Activity Mean | % Activity S. D. |
|---|---|---|---|---|
| Chemical structures of IBA-derived compounds and hpol κ activity in the presence of each compound.[a] | | | | |
| 4 | IBA-4 | 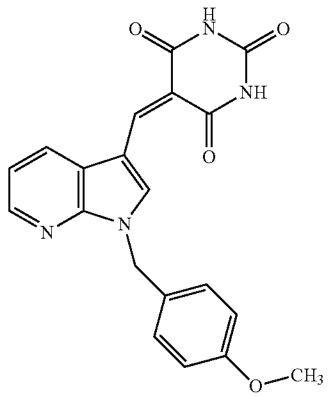 [SMILES: COc1ccc(Cn2cc(C=C3C(=O)NC(=O)NC3=O)c3cccnc32)cc1] | 109.6 | 4.4 |
| 5 | IBA-5 | 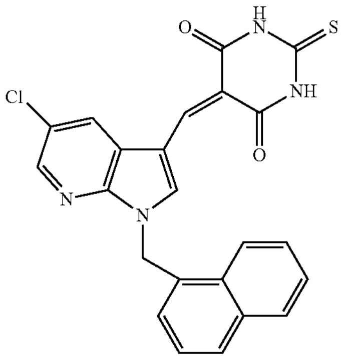 [SMILES: O=C1NC(=S)NC(=O)C1=Cc1cn(Cc2cccc3ccccc23)c2ncc(Cl)cc12] | 109.0 | 20.4 |
| 6 | IBA-6 | 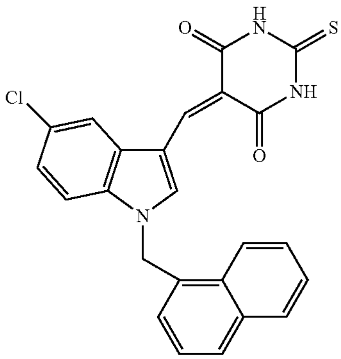 [SMILES: O=C1NC(=S)NC(=O)C1=Cc1cn(Cc2cccc3ccccc23)c2ccc(Cl)cc12] | 107.7 | 5.4 |
| 7 | IBA-7 | 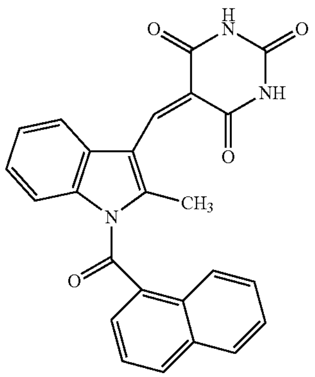 [SMILES: Cc1c(C=C2C(=O)NC(=O)NC2=O)c2ccccc2n1C(=O)c1cccc2ccccc12] | 107.0 | 8.1 |

TABLE 1-continued
| Chemical structures of IBA-derived compounds and hpol κ activity in the presence of each compound.[a] | | | | |
|---|---|---|---|---|
| Compound | | Chemical | % Activity | |
| Number | I. D. | Structure | Mean | S. D. |
| 8 | IBA-8 | 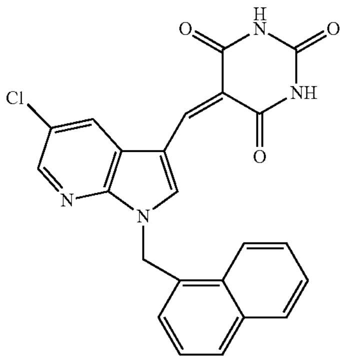 [SMILES: O=C1NC(=O)C(=Cc2cn(Cc3cccc4ccccc34)c3ncc(Cl)cc23)C(=O)N1] | 103.2 | 6.0 |
| 9 | IBA-9 | 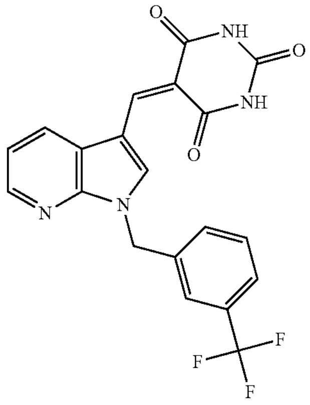 [SMILES: O=C1NC(=O)C(=Cc2cn(Cc3cccc(C(F)(F)F)c3)c3ncccc23)C(=O)N1] | 102.6 | 4.5 |
| 10 | IBA-10 | 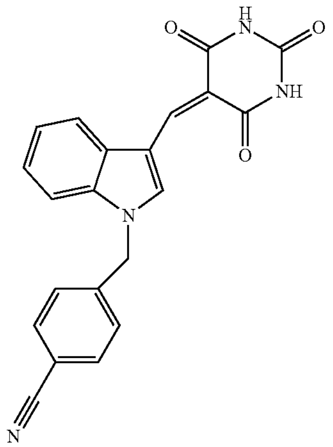 [SMILES: N#Cc1ccc(Cn2cc(C=C3C(=O)NC(=O)NC3=O)c3ccccc32)cc1] | 101.5 | 15.6 |

TABLE 1-continued
Chemical structures of IBA-derived compounds and hpol κ activity in the presence of each compound.[a]
| Compound Number | Compound I. D. | Chemical Structure | % Activity Mean | % Activity S. D. |
|---|---|---|---|---|
| 11 | IBA-11 | 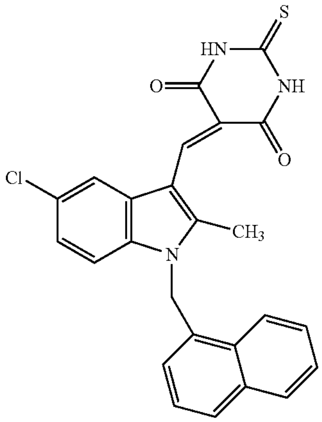 [SMILES: Cc1c(C=C2C(=O)NC(=S)NC2=O)c2cc(Cl)ccc2n1Cc1cccc2ccccc12] | 99.1 | 9.9 |
| 12 | IBA-12 | 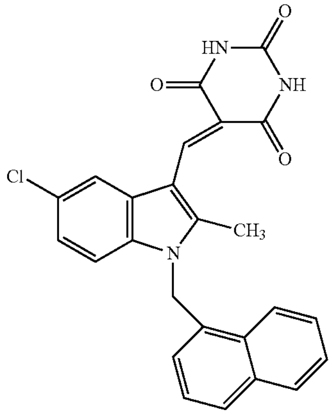 [SMILES: Cc1c(C=C2C(=O)NC(=O)NC2=O)c2cc(Cl)ccc2n1Cc1cccc2ccccc12] | 96.6 | 17.3 |
| 13 | IBA-13 | 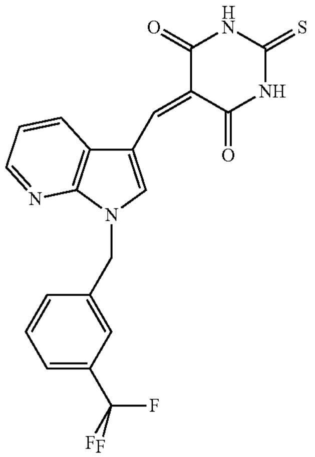 [SMILES: O=C1NC(=S)NC(=O)C1=Cc1cn(Cc2cccc(C(F)(F)F)c2)c2ncccc12] | 96.6 | 12.5 |

TABLE 1-continued
| Chemical structures of IBA-derived compounds and hpol κ activity in the presence of each compound.[a] | | | | |
|---|---|---|---|---|
| Compound | | Chemical | % Activity | |
| Number | I. D. | Structure | Mean | S. D. |
| 14 | IBA-14 | 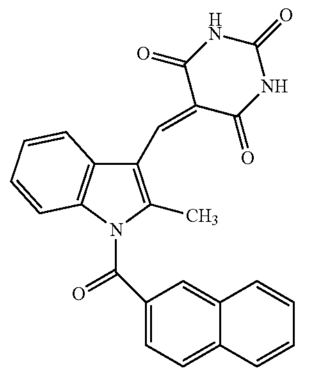 [SMILES: Cc1c(C=C2C(=O)NC(=O)NC2=O)c2ccccc2n1C(=O)c1ccc2ccccc2c1] | 95.7 | 11.1 |
| 15 | IBA-15 | 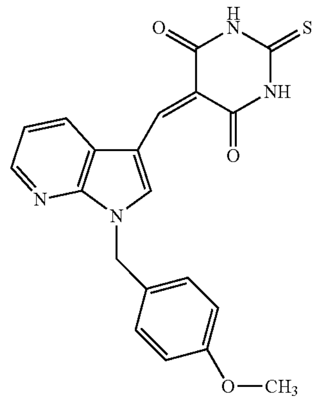 [SMILES: COc1ccc(Cn2cc(C=C3C(=O)NC(=S)NC3=O)c3cccnc32)cc1] | 95.1 | 4.7 |
| 16 | IBA-16 | 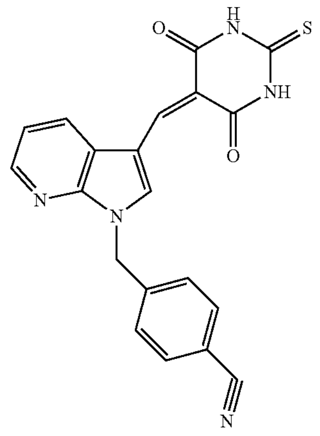 [SMILES: N#Cc1ccc(Cn2cc(C=C3C(=O)NC(=S)NC3=O)c3cccnc32)cc1] | 94.5 | 1.6 |

TABLE 1-continued
| Chemical structures of IBA-derived compounds and hpol κ activity in the presence of each compound.[a] | | | | |
|---|---|---|---|---|
| Compound | | Chemical | % Activity | |
| Number | I. D. | Structure | Mean | S. D. |
| 17 | IBA-17 | 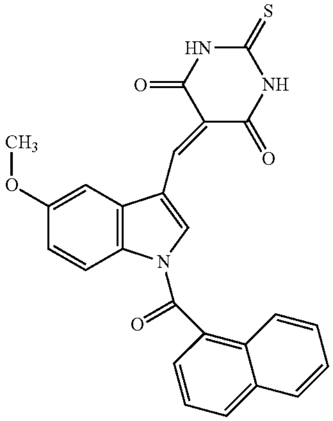 [SMILES: COc1ccc2c(c1)c(C=C1C(=O)NC(=S)NC1=O)cn2C(=O)c1cccc2ccccc12] | 93.8 | 7.3 |
| 18 | IBA-18 | 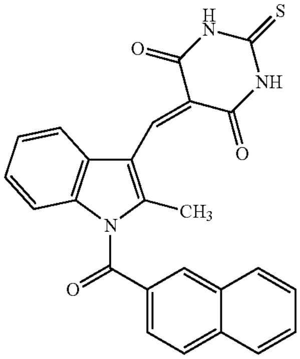 [SMILES: Cc1c(C=C2C(=O)NC(=S)NC2=O)c2ccccc2n1C(=O)c1ccc2ccccc2c1] | 93.5 | 6.4 |
| 19 | IBA-19 | 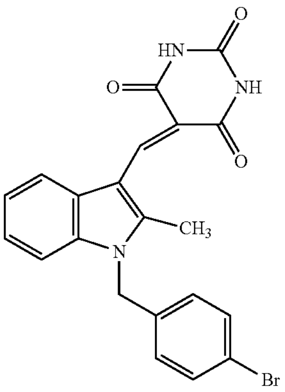 [SMILES: Cc1c(C=C2C(=O)NC(=O)NC2=O)c2ccccc2n1Cc1ccc(Br)cc1] | 93.3 | 8.4 |

TABLE 1-continued
Chemical structures of IBA-derived compounds and hpol κ activity in the presence of each compound.[a]
| Compound Number | Compound I. D. | Chemical Structure | % Activity Mean | % Activity S. D. |
|---|---|---|---|---|
| 20 | IBA-20 | 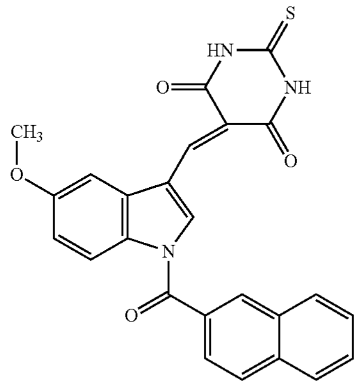 [SMILES: COc1ccc2c(c1)c(C=C1C(=O)NC(=S)NC1=O)cn2C(=O)c1ccc2ccccc2c1] | 92.9 | 7.9 |
| 21 | IBA-21 | 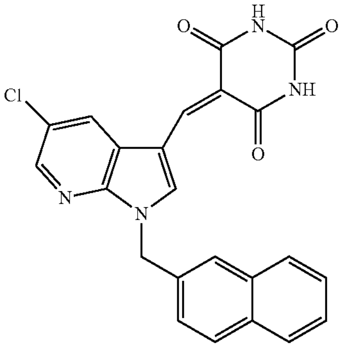 [SMILES: O=C1NC(=O)C(=Cc2cn(Cc3ccc4ccccc4c3)c3ncc(Cl)cc23)C(=O)N1] | 92.2 | 13.2 |
| 22 | IBA-22 | 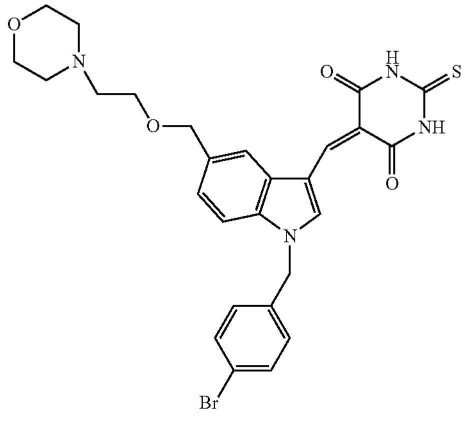 [SMILES: O=C1NC(=S)NC(=O)C1=Cc1cn(Cc2ccc(Br)cc2)c2ccc(COCCN3CCOCC3)cc12] | 91.1 | 2.6 |

TABLE 1-continued
| Chemical structures of IBA-derived compounds and hpol κ activity in the presence of each compound.[a] | | | | |
|---|---|---|---|---|
| Compound | | Chemical | % Activity | |
| Number | I. D. | Structure | Mean | S. D. |
| 23 | IBA-23 | 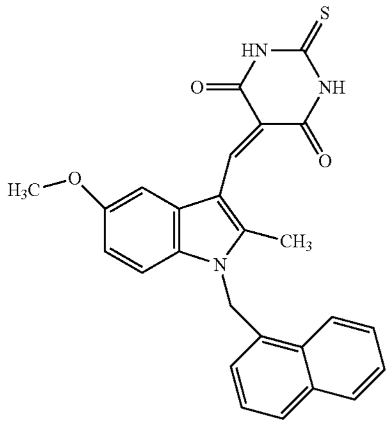 [SMILES: COc1ccc2c(c1)c(C=C1C(=O)NC(=S)NC1=O)c(C)n2Cc1cccc2ccccc12] | 91.0 | 14.1 |
| 24 | IBA-24 | 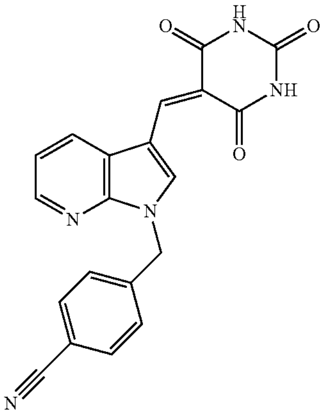 [SMILES: N#Cc1ccc(Cn2cc(C=C3C(=O)NC(=O)NC3=O)c3cccnc32)cc1] | 88.8 | 3.6 |
| 25 | IBA-25 | 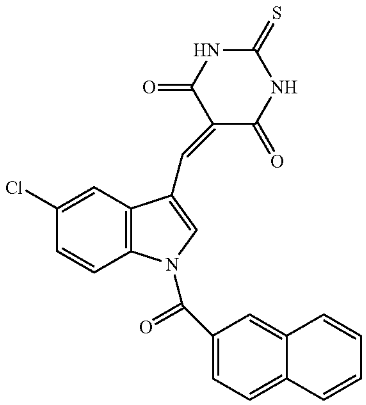 [SMILES: O=C1NC(=S)NC(=O)C1=Cc1cn(C(=O)c2ccc3ccccc3c2)c2ccc(Cl)cc12] | 87.6 | 9.5 |

TABLE 1-continued
Chemical structures of IBA-derived compounds and hpol κ activity in the presence of each compound.[a]
| Compound Number | Compound I. D. | Chemical Structure | % Activity Mean | % Activity S. D. |
|---|---|---|---|---|
| 26 | IBA-26 | 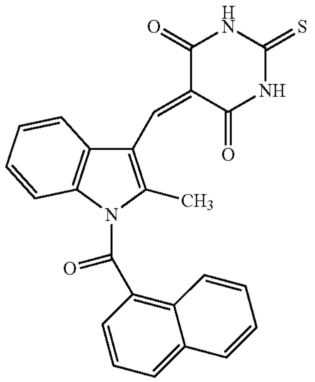 [SMILES: Cc1c(C=C2C(=O)NC(=S)NC2=O)c2ccccc2n1C(=O)c1cccc2ccccc12] | 86.4 | 2.98 |
| 27 | IBA-27 | 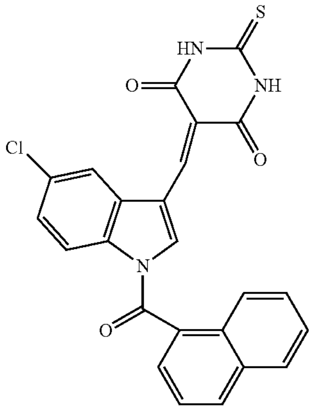 [SMILES: O=C1NC(=S)NC(=O)C1=Cc1cn(C(=O)c2cccc3ccccc23)c2ccc(Cl)cc12] | 85.8 | 14.01 |
| 28 | IBA-28 | 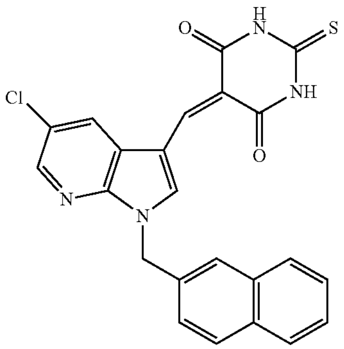 [SMILES: O=C1NC(=S)NC(=O)C1=Cc1cn(Cc2ccc3ccccc3c2)c2ncc(Cl)cc12] | 84.4 | 5.49 |

TABLE 1-continued
| Chemical structures of IBA-derived compounds and hpol κ activity in the presence of each compound.[a] | | | | |
|---|---|---|---|---|
| Compound | | Chemical | % Activity | |
| Number | I. D. | Structure | Mean | S. D. |
| 29 | IBA-29 | 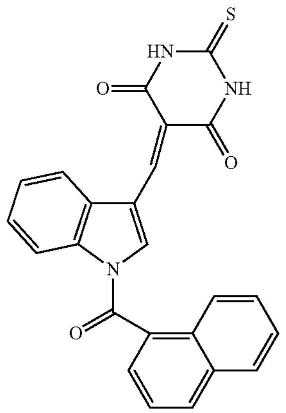 [SMILES: O=C1NC(=S)NC(=O)C1=Cc1cn(C(=O)c2cccc3ccccc23)c2ccccc12] | 83.3 | 1.9 |
| 30 | IBA-30 | 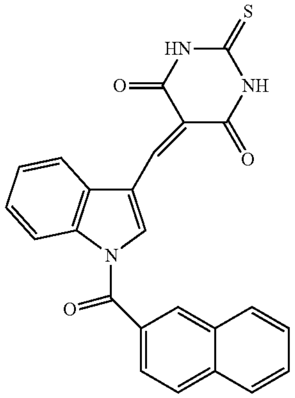 [SMILES: O=C1NC(=S)NC(=O)C1=Cc1cn(C(=O)c2ccc3ccccc3c2)c2ccccc12] | 81.4 | 2.8 |
| 31 | IBA-31 | 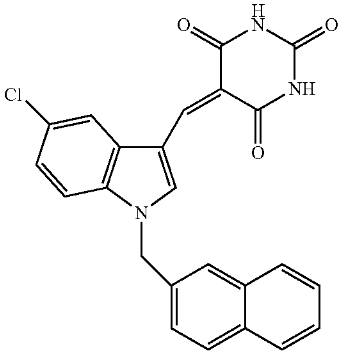 [SMILES: O=C1NC(=O)C(=Cc2cn(Cc3ccc4ccccc4c3)c3ccc(Cl)cc23)C(=O)N1] | 67.6 | 3.0 |

TABLE 1-continued

| Chemical structures of IBA-derived compounds and hpol κ activity in the presence of each compound.[a] | | | | |
|---|---|---|---|---|
| Compound | | Chemical | % Activity | |
| Number | I. D. | Structure | Mean | S. D. |
| 32 | IBA-32 | 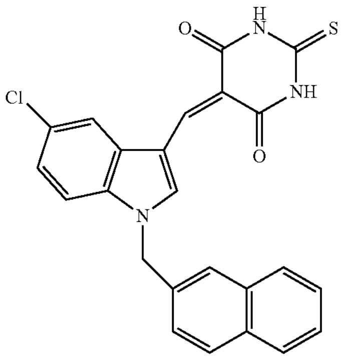 [SMILES: O=C1NC(=S)NC(=O)C1=Cc1cn(Cc2ccc3ccccc3c2)c2ccc(Cl)cc12] | 56.5 | 3.7 |
| 33 | IBA-33 | 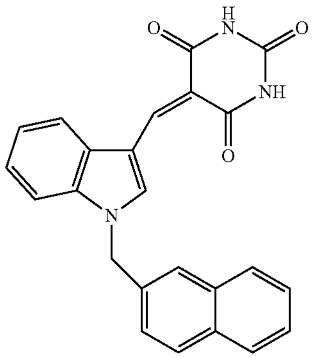 [SMILES: O=C1NC(=O)C(=Cc2cn(Cc3ccc4ccccc4c3)c3ccccc23)C(=O)N1] | 17.9 | 13.8 |
| 34 | IBA-34 | 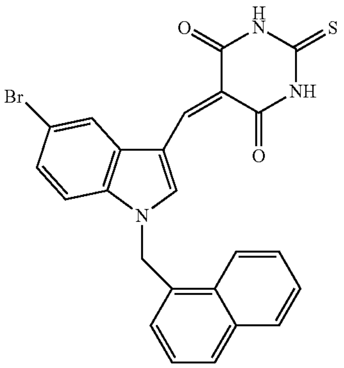 [SMILES: O=C1NC(=S)NC(=O)C1=Cc1cn(Cc2cccc3ccccc23)c2ccc(Br)cc12] | 3.7 | 6.5 |

[a]The percent activity was calculated by measuring the rate of product formation as a function of time in the presence of each compound (40 μM) and dividing by the rate of the DMSO control experiment. The results shown represent the mean (± s.d.) of three independent experiments.

TABLE 2
Chemical structures of IAG-derived compounds and hpol $\kappa$ activity in the presence of each compound.[b]
| Compound | | Chemical | % Activity | |
|---|---|---|---|---|
| Number | I. D. | Structure | Mean | S. D. |
| 1 | IAG-1 | 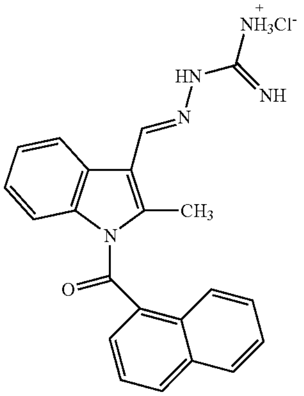 | 105.0 | 9.5 |
| 2 | IAG-2 | 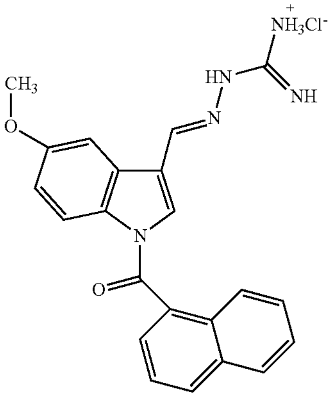 | 104.0 | 4.3 |
| 3 | IAG-3 | 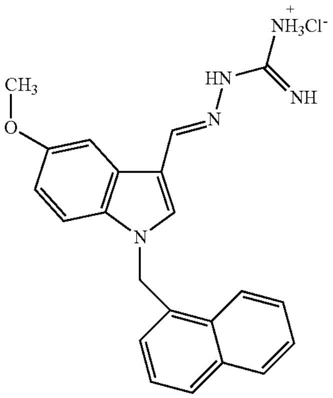 | 101.0 | 13.8 |

TABLE 2-continued
| Chemical structures of IAG-derived compounds and hpol κ activity in the presence of each compound.[b] | | | | |
|---|---|---|---|---|
| Compound | | Chemical | % Activity | |
| Number | I. D. | Structure | Mean | S. D. |
| 4 | IAG-4 | 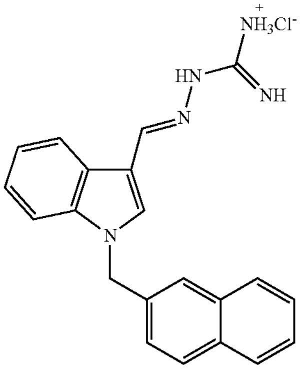 | 95.0 | 5.4 |
| 5 | IAG-5 | 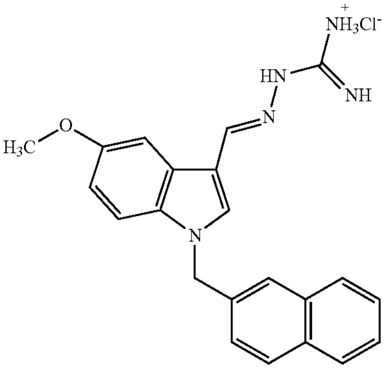 | 94.0 | 11.2 |
| 6 | IAG-6 | 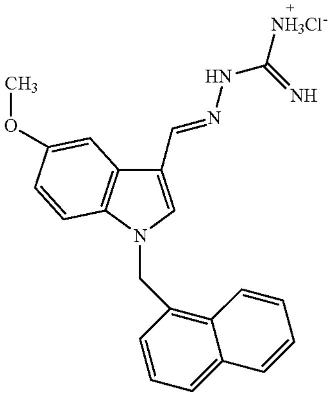 | 87.0 | 12.8 |

TABLE 2-continued
| Chemical structures of IAG-derived compounds and hpol κ activity in the presence of each compound.[b] | | | | |
|---|---|---|---|---|
| Compound | | Chemical | % Activity | |
| Number | I. D. | Structure | Mean | S. D. |
| 7 | IAG-7 | 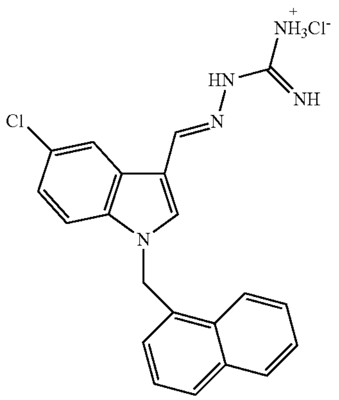 | 64.0 | 12.5 |
| 8 | IAG-8 | 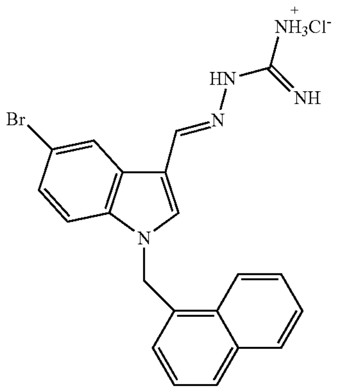 | 57.0 | 6.3 |
| 9 | IAG-9 | 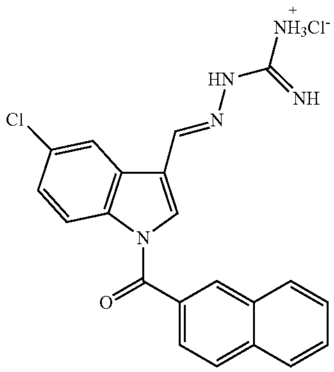 | 30.0 | 2.1 |

TABLE 2-continued

| Chemical structures of IAG-derived compounds and hpol κ activity in the presence of each compound.[b] | | | | |
|---|---|---|---|---|
| Compound | | Chemical | % Activity | |
| Number | I. D. | Structure | Mean | S. D. |
| 10 | IAG-10 | 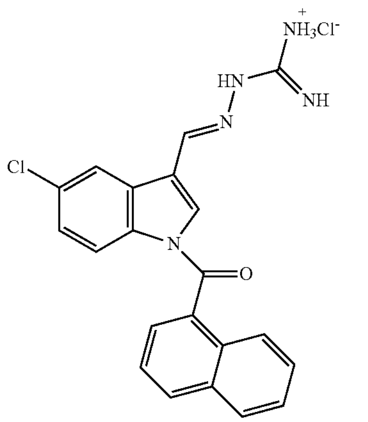 | 0.0 | 0.0 |

[b]The percent activity was calculated by measuring the rate of product formation as a function of time in the presence of each compound (40 μM) and dividing by the rate of the DMSO control experiment. The results shown represent the mean (± s.d.) of three independent experiments.

The assay conditions included 1 nM hpol κ, 50 nM DNA, 40 μM test compound (dissolved in DMSO), 100 μM dTTP and 1 mM $MgCl_2$. The reactions were performed in 50 mM Tris (pH 8.0) buffer containing 40 mM NaCl, 2 mM dithiothreitol and 0.01% (v/v) Tween-20. In control reactions, DMSO was added instead of the compound, to a similar final concentration of 10% v/v. The enzyme, test compound (or DMSO) and dTTP were combined with the reaction buffer in individual wells and incubated for 5-10 minutes to allow the compound to bind to the enzyme. Subsequently, the reaction was initiated by addition of DNA substrate and the plate was read immediately using a BioTek SynergyH4 plate reader ($\lambda_{ex}$=525 nm, $\lambda_{em}$=598 nm). The final reaction volume was typically 200 μL. Fluorescence was monitored for 60 to 90 minutes for most reactions. All fluorescence-based polymerase assays were performed at 25° C. The initial linear portion of the velocity curve was analyzed to calculate an observed rate of product formation. For each data set, we averaged eight DMSO control experiments to obtain our measure of 100% activity. Rates of product formation in the presence of each compound were then divided by the rate of the DMSO control to produce a relative measure of polymerase activity. The $IC_{50}$ value was estimated using a four-parameter logistic model defined by equation 1:

$$y = \text{bottom} + \frac{(\text{top} - \text{bottom})}{1 + (x/IC_{50})^{slope}} \quad \text{Eq. 1}$$

The experiments were performed in triplicate and the mean (±standard deviation) of the $IC_{50}$ values calculated for each data set is reported.

The fluorescence-based assay, as described above, was also employed to help elucidate the mechanism of inhibition of hpol κ by IAG-10. Briefly, the steady-state kinetic parameters for hpol κ activity were determined in the presence of multiple concentrations of dTTP (0, 0.2, 0.4, 0.8, 1.6, 3.2, 6.4, 12.8, 20, 30, 40 and 50 μM). The hpol κ enzyme was used at 0.5 nM, while the TAMRA-labeled DNA substrate (described above) was used at 25 nM. The activity of hpol κ was determined for each dTTP concentration by monitoring the change in fluorescence as a function of time and using the linear portion of each curve to calculate the reaction velocity. The rate of product formation was then plotted as a function of dTTP concentration and fit to a hyperbola to estimate the Michealis constant ($K_{M,dTTP}$). The turnover number ($k_{cat}$) was calculated after correcting for the enzyme concentration. These experiments were then repeated in the presence of IAG-10 (0-10 μM) to determine the effect of the small-molecule upon Michaelis-Menten kinetics and to help elucidate the mechanism of inhibition of hpol κ by IAG-10.

Gel-Based Primer Extension Assay Measuring DNA Polymerase Activity

The Y-family member hRevl was not easily amenable to the fluorescence-based assay used for the other polymerases. Therefore, we used a gel-based assay to determine the polymerase activity of all four human Y-family polymerases (hpol κ, hpol η, hpol ι and Rev1) in the absence or presence of IAG-10, in order to determine the degree of specificity of inhibition of the compound towards hpol κ. For this assay, extension of a 13/18-mer primer-template DNA substrate by each DNA polymerase was studied. The DNA substrate was prepared by annealing the FAM labeled primer to a complementary template oligonucleotide (1:2, primer:template molar ratio) by incubating at 95° C. for 5 min followed by slow cooling to RT. The polymerase extension assay was performed in 50 mM HEPES (pH 7.5) buffer containing 50 mM NaCl, 1 mM DTT, 0.1 mg mL-1 BSA, and 10% (v/v) glycerol. The enzymes were used at the following concentrations: 1 nM hpol κ, 2 nM hpol η, 10 nM hpol ι and 10 nM hRev1. Each enzyme was incubated with 10% DMSO (control) or 10 μM of IAG-10 for five minutes, before initiating the reaction by the addition of DNA•dNTP•$Mg^{2+}$ (200 nM DNA, 100 μM of each dNTP and 5 mM $MgCl_2$) at 37° C. The reactions were terminated by adding quench solution (20 mM EDTA and 95% v/v formamide) to each reaction followed by heating at 95° C. The samples were separated using a 15% (w/v) polyacrylamide-7 M urea gel, and the product formation was analyzed as described previously. The experiments were performed in triplicate, and for each enzyme, percent (%) activity was calculated by normalizing to the specific activity in the DMSO-control condition (taken as 100%). The polymerase extension assay was performed in 50 mM HEPES (pH 7.5) buffer containing 50 mM NaCl, 1 mM DTT, 0.1 mg/mL BSA and 10% (v/v) glycerol. The enzymes were used at the following concentrations: The reactions were terminated by adding quench solution (20 mM EDTA and 95% v/v formamide) to each reaction followed by heating at 95° C. The samples were separated using a 15% (w/v) polyacrylamide-7 M urea gel, and the product formation was analyzed as described previously. The experiments were performed in triplicate, and for each enzyme, percent (%) activity was calculated by normalizing to the specific activity in the DMSO-control condition (taken as 100%). Members representing the other DNA pol families (hpol β, hpol λ—X-family; TB pol I—A-family; Dpo1—B-family) were also assayed for specificity of inhibition by IAG-10 at a single dose of 10 μM using the fluorescence-based assay.

DNA Binding Analysis

Fluorescence anisotropy DNA binding assays were performed as described previously, to determine the effect of the compounds UAMS-48 on the DNA-binding affinity of hpol κ. Briefly, an 11-mer oligo was mixed with a fluorescein-labeled 28-mer oligo in a 1:1.2 molar ratio, incubated at 95° C. for 5 min followed by slow-cooling to room temperature. The annealed FAM-labeled duplex DNA substrate (2 nM) was incubated with increasing concentrations of hpol κ, and fluorescence polarization was measured in a Biotek SynergyH4 plate reader using the appropriate filter sets ($\lambda_{ex}$=485±20 nm and $\lambda_{em}$=525±20 nm). All titrations were performed at 25° C. in 50 mM HEPES buffer (pH 7.5) containing 10 mM KOAc, 10 mM $MgCl_2$, 10 mM KCl, 2 mM β-mercaptoethanol (β-ME), 10% (v/v) dimethyl sulfoxide (DMSO) and 0.1 mg/mL BSA. The experiments were performed in the presence of increasing concentrations of UAMS-48, in the range (0-10 μM) bracketing its $IC_{50}$ for hpol κ. The resulting polarization data were fit to a quadratic equation to estimate the equilibrium dissociation constant ($K_{D,DNA}$) for hpol κ binding to the duplex DNA.

p-Hydroxyphenylglyoxal (HPG) Labeling of Hpol κ to Identify Binding Sites for IAG-10

HPG is a commonly used amino-acid modifier, which when reacted with a protein, modifies the L-arginine side chains selectively. HPG labeling experiments were performed with hpol κ (10 μM) in the presence or absence of UAMS-48. Briefly, hpol κ was pre-incubated with either 20 μM (1:2 molar ratio) or 100 μM (1:10 molar ratio) IAG-10 for 10 mins at 37° C. in 50 mM HEPES buffer (pH 7.8) containing 200 mM NaCl, 10 mM $MgCl_2$, and 10% v/v DMSO. The HPG labeling was carried out at 37° C. in the dark for 1 hr by adding 500 μM of HPG to the pre-incubated reaction mix, followed by addition of 200 mM of free L-arginine to quench the reaction after 1 hr. The samples were then resolved on an SDS-PAGE gel and submitted to the UAMS Proteomics Core Facility for analysis by mass spectrometry. In-gel trypsin digestion was employed to obtain peptides, which were then subjected to tandem liquid chromatography-mass spectrometric (LC-MS) analysis.

Quantification of HPG Labeled Peptides

Unmodified and HPG-modified peptides were both identified as described previously (Zafar et al. 2018), using Scaffold Viewer (Proteome Software Inc.). The modified peptides have a molecular weight of the peptide fragment plus the 132-Da HPG adduct (Table 3).

TABLE 3

Hpol κ-derived peptides (trypsin-digested) identified by mass spectrometry.

| Peptide sequence (Trypsin cleavage sites in parentheses) | m/z | M.W. | Charge State | Residue: Start-End |
|---|---|---|---|---|
| (K)AGMEGLDKEK(I) (SEQ ID NO: 3) | 539.27 | 1076.52 | +2 | 26-35 |
| (K)AGmEGLDKEK(I)* (SEQ ID NO: 3) | 547.26 | 1092.51 | +2 | 26-35 |
| (K)AGmEGLDKEKINK(I) (SEQ ID NO: 4) | 724.87 | 1447.73 | +2 | 26-38 |
| (K)AGmEGLDKEKINK(I) (SEQ ID NO: 4) | 483.59 | 1447.73 | +3 | 26-38 |
| (K)INKIIMEATKGSR(F) (SEQ ID NO: 5) | 487.61 | 1459.82 | +3 | 36-48 |
| (K)GS**R**FYGNELKK(E)** (SEQ ID NO: 6) | 715.86 | 1429.70 | +2 | 46-56 |
| (K)GSRFYGNELKK(E) (SEQ ID NO: 6) | 433.57 | 1297.68 | +3 | 46-56 |
| (R)FYGNELKKEK(Q) (SEQ ID NO: 7) | 628.34 | 1254.66 | +2 | 49-58 |
| (K)EKQVNQ**R**IENMMQQK(A) (SEQ ID NO: 8) | 679.33 | 2034.96 | +3 | 57-71 |
| (K)EKQVNQRIENmmQQK(A) (SEQ ID NO: 8) | 645.98 | 1934.93 | +3 | 57-71 |
| (K)QVNQ**R**IENmmQQK(A) (SEQ ID NO: 9) | 905.91 | 1809.81 | +2 | 59-71 |
| (K)QVNQRIENmmQQK(A) (SEQ ID NO: 9) | 839.90 | 1677.79 | +2 | 59-71 |
| (R)IENMMQQKAQITSQQLR(K) (SEQ ID NO: 10) | 683.02 | 2046.03 | +3 | 64-80 |
| (R)IENmmQQKAQITSQQLR(K) (SEQ ID NO: 10) | 693.68 | 2078.03 | +3 | 64-80 |
| (K)AQITSQQL**R**K(A) (SEQ ID NO: 11) | 652.85 | 1303.69 | +2 | 72-81 |
| (K)AQITSQQLRK(A) (SEQ ID NO: 11) | 391.56 | 1171.67 | +3 | 72-81 |
| (R)KAQLQVD**R**FAMELEQSR(N) (SEQ ID NO: 12) | 727.70 | 2180.07 | +3 | 81-97 |
| (R)KAQLQVDRFAMELEQSR(N) (SEQ ID NO: 12) | 683.69 | 2048.05 | +3 | 81-97 |
| (R)KAQLQVD**R**FAmELEQSR(N) (SEQ ID NO: 12) | 733.03 | 2196.06 | +3 | 81-97 |
| (R)NLSNTIVHIDMDAFYAAVEMR(D) (SEQ ID NO: 13) | 804.06 | 2409.15 | +3 | 98-118 |
| (R)NLSNTIVHIDmDAFYAAVEmR(D) (SEQ ID NO: 13) | 814.72 | 2441.13 | +3 | 98-118 |
| (R)NLSNTIVHIDmDAFYAAVEmRDNPELK(D) (SEQ ID NO: 14) | 1046.83 | 3137.48 | +3 | 98-124 |
| (R)NLSNTIVHIDMDAFYAAVEMRDNPELK(D) (SEQ ID NO: 14) | 1036.17 | 3105.49 | +3 | 98-124 |
| (R)DNPELKDKPIAVGSMSMLSTSNYHAR(R) (SEQ ID NO: 15) | 716.10 | 2860.38 | +4 | 119-124 |
| (R)DNPELKDKPIAVGSmSmLSTSNYHAR(R) (SEQ ID NO: 15) | 724.10 | 2892.37 | +4 | 119-144 |
| (K)DKPIAVGSmSMLSTSNYHA**R**R(F) (SEQ ID NO: 16) | 618.05 | 2468.16 | +4 | 125-145 |
| (K)DKPIAVGSMSmLSTSNYHA**R**R(F) (SEQ ID NO: 16) | 618.05 | 2468.16 | +4 | 125-145 |
| (R)RFGV**R**AAMPGFIAK(R) (SEQ ID NO: 17) | 551.63 | 1651.87 | +3 | 145-158 |
| (R)**R**FGVRAAMPGFIAK(R) (SEQ ID NO: 17) | 551.63 | 1651.86 | +3 | 145-158 |
| (K)RLcPQLIIVPPNFDK(Y)* (SEQ ID NO: 18) | 905.51 | 1809.00 | +2 | 159-173 |
| (K)**R**LcPQLIIVPPNFDK(Y) (SEQ ID NO: 18) | 648.01 | 1941.02 | +3 | 159-173 |

TABLE 3-continued

Hpol κ-derived peptides (trypsin-digested) identified by mass spectrometry.

| Peptide sequence (Trypsin cleavage sites in parentheses) | m/z | M.W. | Charge State | Residue: Start-End |
|---|---|---|---|---|
| (K)**R**LcPQLIIVPPNFDKYR(A) (SEQ ID NO: 19) | 566.05 | 2260.18 | +4 | 159-175 |
| (K)RLcPQLIIVPPNFDKYR(A) (SEQ ID NO: 19) | 533.05 | 2128.16 | +4 | 159-175 |
| (K)EVKEILADYDPNFMAMSLDEAYLNITK(H) (SEQ ID NO: 20) | 1045.18 | 3132.51 | +3 | 180-206 |
| (K)EILADYDPNFMAMSLDEAYLNITK(H) (SEQ ID NO: 21) | 1389.16 | 2776.30 | +2 | 183-206 |
| (K)EILADYDPNFmAmSLDEAYLNITK(H) (SEQ ID NO: 21) | 937.10 | 2808.29 | +3 | 183-206 |
| (R)QNWPEDKRR(Y) (SEQ ID NO: 22) | 410.21 | 1227.61 | +3 | 212-220 |
| (R)YFIKMGSSVENDNPGK(E) (SEQ ID NO: 23) | 595.95 | 1784.84 | +3 | 221-236 |
| (R)YFIKmGSSVENDNPGK(E) (SEQ ID NO: 23) | 601.29 | 1800.83 | +3 | 221-236 |
| (K)MGSSVENDNPGKEVNK(L) (SEQ ID NO: 24) | 568.93 | 1703.78 | +3 | 225-240 |
| (K)mGSSVENDNPGKEVNK(L) (SEQ ID NO: 24) | 574.26 | 1719.77 | +3 | 225-240 |
| (K)EVNKLSEHER(S) (SEQ ID NO: 25) | 620.82 | 1239.62 | +2 | 237-246 |
| (R)SISPLLFEESPSDVQPPGDPFQVNFEEQNNPQILQNSVVFGTSAQEVVK(E) (SEQ ID NO: 26) | 1347.17 | 5384.64 | +4 | 247-295 |
| (R)FRIEQKTTLTASAGIAPNTmLAK(V) (SEQ ID NO: 27) | 620.34 | 2477.33 | +4 | 299-321 |
| (K)TTLTASAGIAPNTMLAK(V) (SEQ ID NO: 28) | 554.30 | 1659.89 | +3 | 305-321 |
| (K)TTLTASAGIAPNTMLAKVcSDK(N) (SEQ ID NO: 29) | 750.72 | 2249.14 | +3 | 305-326 |
| (K)VcSDKNKPNGQYQILPNR(Q) (SEQ ID NO: 30) | 533.52 | 2130.06 | +4 | 322-339 |
| (K)NKPNGQYQILPNR(Q) (SEQ ID NO: 31) | 771.41 | 1540.81 | +2 | 327-339 |
| (R)QAVmDFIKDLPIRK(V) (SEQ ID NO: 32) | 423.24 | 1688.93 | +4 | 340-353 |
| (R)QAVMDFIKDLPIRK(V) (SEQ ID NO: 32) | 419.24 | 1672.93 | +4 | 340-353 |
| (R)QAVmDFIKDLPI**R**K(V) (SEQ ID NO: 32) | 456.24 | 1820.95 | +4 | 340-353 |
| (R)KVSGIGKVTEK(M) (SEQ ID NO: 33) | 382.57 | 1144.68 | +3 | 353-363 |
| (K)VSGIGKVTEK(M) (SEQ ID NO: 34) | 509.30 | 1016.59 | +2 | 354-363 |
| (K)mLKALGIITcTELYQQR(A) (SEQ ID NO: 35) | 685.36 | 2053.07 | +3 | 364-380 |
| (K)ALGIITcTELYQQR(A) (SEQ ID NO: 36) | 833.43 | 1664.85 | +2 | 367-380 |
| (R)ALLSLLFSETSWHYFLHISLGLGSTHLTR(D) (SEQ ID NO: 37) | 1100.59 | 3298.75 | +3 | 381-409 |
| (R)DGERKSMSVER(T) (SEQ ID NO: 38) | 431.88 | 1292.61 | +3 | 410-420 |
| (R)KSmSVER(T) (SEQ ID NO: 39) | 426.72 | 851.42 | +2 | 414-420 |
| (R)TFSEINKAEEQYSLcQELcSELAQDLQK(E) (SEQ ID NO: 40) | 1121.19 | 3360.56 | +3 | 421-448 |
| (K)AEEQYSLcQELcSELAQDLQK(E) (SEQ ID NO: 41) | 1271.58 | 2541.14 | +2 | 428-448 |
| (R)LKGRTVTIKLKNVNFEVK(T) (SEQ ID NO: 42) | 418.26 | 2086.26 | +5 | 451-468 |
| (K)G**R**TVTIK(L) (SEQ ID NO: 43) | 453.76 | 905.50 | +2 | 453-459 |
| (R)TVTIKLKNVNFEVK(T) (SEQ ID NO: 44) | 409.00 | 1631.96 | +4 | 455-468 |
| (R)TVTIKLKNVNFEVKTR(A) (SEQ ID NO: 45) | 378.83 | 1889.11 | +5 | 455-470 |
| (K)LKNVNFEVK(T) (SEQ ID NO: 46) | 545.82 | 1089.62 | +2 | 460-468 |
| (K)TRASTVSSVVSTAEEIFAIAK(E) (SEQ ID NO: 47) | 1084.09 | 2166.16 | +2 | 469-489 |
| (K)TRASTVSSVVSTAEEIFAIAKELLKTEIDADFPHPLR(L) (SEQ ID NO: 48) | 809.24 | 4041.14 | +5 | 469-505 |
| (R)ASTVSSVVSTAEEIFAIAK(E) (SEQ ID NO: 49) | 955.51 | 1909.00 | +2 | 471-489 |
| (R)ASTVSSVVSTAEEIFAIAKELLK(T) (SEQ ID NO: 50) | 798.44 | 2392.31 | +3 | 471-493 |
| (R)ASTVSSVVSTAEEIFAIAKELLKTEIDADFPHPLR(L) (SEQ ID NO: 51) | 757.81 | 3783.99 | +5 | 471-505 |
| (R)ASTVSSVVSTAEEIFAIAKELLKTEIDADFPHPLRLR(L) (SEQ ID NO: 52) | 811.64 | 4053.18 | +5 | 471-507 |
| (K)TEIDADFPHPLRL**R**(L) (SEQ ID NO: 53) | 604.64 | 1810.90 | +3 | 494-507 |
| (R)L**R**LmGVR(I) (SEQ ID NO: 54) | 496.77 | 991.53 | +2 | 506-512 |
| (R)LRLMGVR(I) (SEQ ID NO: 54) | 422.76 | 843.51 | +2 | 506-512 |
| (R)LMGV**R**ISSFPNEEDR(K) (SEQ ID NO: 55) | 627.96 | 1880.87 | +3 | 508-522 |
| (R)LMGVRISSFPNEEDRK(H) (SEQ ID NO: 56) | 626.66 | 1876.95 | +3 | 508-523 |
| (R)ISSFPNEEDRK(H) (SEQ ID NO: 57) | 441.22 | 1320.63 | +3 | 513-523 |
| (R)ISSFPNEED**R**K(H) (SEQ ID NO: 57) | 485.22 | 1452.65 | +3 | 513-523 |

*Lowercase 'm' indicates oxidation (+16), and lowercase 'c' indicates carbamidomethyl modification (+57) of Met residues.

**Arg residues highlighted in BOLD were modified by HPG (+132).

The peak intensity was then quantified manually using the corresponding m/z value and the relative abundance for each modified peptide was calculated as a function of area under the peak in Xcalibur™ software (ThermoFisher Scientific). The percentage of modified arginine measured by mass spectrometry was calculated as a fraction of total arginine (i.e. unmodified+HPG modified) quantified for a specific residue. The data for each peptide was normalized to the hpol κ-HPG alone sample to calculate the change in HPG modification after treatment with IAG-10.

Human Cell Culture and Clonogenic Survival Assay

HAP-1 and hpol $\kappa^{KO}$ cells were purchased from Horizons Discovery Group LLC (Cambridge, UK). The company generated the Hap1 cells using CRISPR-Cas9 technology and the elimination of kappa expression was confirmed by Sanger sequence genome editing. We further confirmed the elimination of hpol κ protein expression by Western blotting (data not shown). Hap1 cells were cultured in Iscove's modified Dulbecco's medium (IMDM; Invitrogen, CA, USA) supplemented with 10% (v/v) fetal bovine serum (FBS; Atlas Biologicals, CO, USA) and 1% (v/v) antibiotic/antimycotic solution (Sigma-Aldrich, MO, USA).T98G cells were purchased from ATCC (American Type Culture Collection, VA, USA). T98G cells were cultured in MEM (Minimum Essential Medium) (Invitrogen, CA, USA) supplemented with 10% (v/v) FBS (Fetal Bovine Serum, Atlas Biologicals, CO, USA) and antibiotic/antimycotic solution (1%, v/v) (Sigma-Aldrich, MO, USA). NT2 cells were kindly provided by Dr. Michael Borrelli (University of Arkansas for Medical Sciences, AR, USA). NT2 cells were cultured in DMEM/F12 (Dulbecco's Modified Eagle Medium) supplemented with 10% (v/v) FCS (Fetal Calf Serum) and antibiotic/antimycotic solution (1%) (Sigma-Aldrich, MO, USA).

To measure the clonogenic ability, cells were plated (500 cells per well) in 6-well dishes. In the case of HAP-1 cells, cells were treated the following day after plating, with temozolomide (TMZ) (0, 1, 5, 50, 125 and 250 μM) alone or in combination with UAMS-48 (0.1 and 0.5 μM) for 1 hour. In the case of T98G and NT2 cells, treatment was done on the following day of plating, with increasing concentrations of TMZ alone or in combination with UAMS-48 (50 nM) for 3 hrs. T98G and NT2 cells were treated with increasing concentrations of UAMS-48 for 3 hrs. After treatment, cells were cultured in fresh IMDM supplemented with 10% FBS for 10 days. The colonies were gently washed with 1×PBS, fixed with 3.7% (v/v) formaldehyde for 20 mins at RT and stained with crystal violet solution (Sigma-Aldrich, MO, USA) for 30 mins at RT.

The fixed crystal-violet stained colonies in each 6-well plate were examined under an EVOS XL Core imaging system (Thermo Fisher Scientific) under bright-field, and the colonies were inspected manually. By considering a group of ~50 cells as one colony for hpol κ-proficient HAP-1, T98G and NT2 cells (hpol κ-deficient cells showed consistently smaller colonies, hence for these, ~25 cells together were considered one colony), an average minimum radius was determined for one colony. Color images of each 6-well plate were captured and opened for processing using the Fiji version of the freely available software ImageJ. Setting the appropriate threshold for counting colonies for each cell type, corresponding to the respective radii calculated previously, the colonies were counted using the Colony Area plugin of ImageJ. Manual counting was performed on a few wells picked randomly, and the colony count so obtained was tallied with the number obtained using ImageJ, to ensure they matched reasonably. All experiments were performed in triplicate, and the colony number for each well was expressed as the mean (±standard deviation). The results were plotted to generate a dose response curve for TMZ treatment using the software Graphpad Prism, where the mean number of colonies was plotted along the Y-axis, and the TMZ concentration along the X-axis. Bar charts comparing the mean number of colonies as a function of the various conditions were also plotted for both cell types. Combination index values were calculated using the Chou-Talalay method (Chou 2010).

Alkaline Comet Assay

To evaluate DNA damage upon treatment with TMZ and the compound IAG-10, the alkaline comet assay was performed using protocol as described by the manufacturer (Trevigen, Gaithersburg, MD). Briefly, 100 000 HAP-1 cells per well for both the hpol κ-proficient and hpol κ-deficient cell types were plated in a 12-well dish. Both types of cells were treated with 0.5 μM of IAG-10 alone or in combination with TMZ (100 μM) for 1 h. Cells treated with DMSO served as the control. Following treatment, cells were harvested, washed in ice-cold Ix PBS, and counted. The cells were then suspended in low-melting agarose to a final dilution of 200-300 cells per well on the comet slide. The comet slides with wells coated with cell/agarose mixture were incubated at 4° C. in the dark to allow the agarose to solidify before immersing the slides in proprietary lysis solution for 1 h. Each comet slide was then immersed in an alkaline unwinding solution (200 mM NaOH, 1 mM EDTA) for 20 min at RT before placing them in the electrophoresis unit in mL of the same solution. Samples were electrophoresed at 21 V for 30 min at 4° C. The comet slides were washed and dried completely at 37° C. before staining with SYBR Gold diluted in TE buffer (10 mM Tris-HCl, pH 7.5, 1 mM EDTA). The comets were visualized using an EVOS FL Auto microscope (Life Technologies, Carlsbad, CA) set at 10× magnification and were scored using CometScore software. All experiments were repeated in 3 biological replicates with at least 60 comets scored for each condition. Results were plotted using Graphpad Prism, as the percent of DNA in the tail of each comet, and statistical significance between treatment conditions was calculated using one-way ANOVA with the Bonferroni posthoc correction.

supF Mutagenesis Assay

HAP-1 hpol κ-proficient and hpol κ-deficient cells were cultured in 10 cm dishes to ~80% confluency in Iscove's modified Dulbecco's medium (Invitrogen) containing 10% (v/v) FBS supplemented with Ix antibiotic antimycotic solution (Sigma). They were transfected with unmodified (control) and methylmethanesulfonate (MMS)-modified pSP189 plasmid harboring the supF gene either in the absence or presence of 1 μM IAG-10. For plasmid modification with MMS, the pSP189 plasmid was first incubated with 100 mM MMS in 10 mM HEPES buffer (pH 7.5) containing 50 mM KCl, 5 mM $MgCl_2$, and 1 mM dithiothreitol at RT for 1 h. The MMS-modified plasmid was then purified by ethanol precipitation and used in subsequent transfections, similar to the unmodified plasmid. The HAP-1 hpol κ-proficient and hpol κ-deficient cells were transfected for 24 h with the unmodified or MMS-modified pSP189 plasmids (10 μg plasmid per 10 cm dish) using Lipofectamine 3000 as per manufacturer's instructions, either in the presence or absence of 1 μM IAG-10, followed by harvesting of the cells. Plasmids were extracted using plasmid miniprep kit (Qiagen) from the cell pellets of all samples and digested with the Dpn I endonudease to eliminate unreplicated plasmids. The recovered plasmids (75-100 ng) were then transformed into *E. coli* MBM7070 strain by electroporation, and the transformed bacterial cells were plated on LB-agar plates containing 100 μg/mL ampicillin, 1 mM isopropyl-I-thio-fi-Dgalactopyranoside (IPTG) and 100 μg/mL X-gaL The resulting blue (nonmutated) and white (mutated) colonies were counted. The mutation frequency was calculated as the ratio of mutant (white) colonies to total (blue+white) colonies. At least 10 000 colonies were counted for each condition, and the results reported represent the mean (±SD) of experiments performed in biological triplicate.

Synthetic Procedure and Analytical Data for the Indoleaminoguanidine Hydrochloride Derivatives Aminoguanidine hydrochloride (1.0 mmol, 1.0 equivalent,) and the appropriate N-1 or 2-naphthalenylmethyl, N-1 or 2-naphthoyl or N-naphthalene-1-ylsulfonyl/N-naphthalene-2-yl sulfonyl indole aldehyde (1.25 mmol, 1.25 equivalents) were dissolved in methanol (10 ml), the solution heated to reflux, and then stirred for a period of 4-6 hours (Prasad and McKay 1967). After completion of the reaction the alcohol was removed by concentration under reduced pressure, and the residue obtained was triturated in dichloromethane for 15 minutes to obtain a solid. The solid was filtered, washed with dichloromethane or chloroform to remove unreacted aldehyde, and dried under reduced pressure to afford the desired indoleaminoguanidine hydrochloride analogs. (Scheme 1). The structure and purity of these derivatives were verified by $^1H$ and $^{13}C$-NMR spectroscopy.

Synthetic Procedure for the Indoleaminoguanidine Freebase Derivatives

Simple and substituted N-1 or 2-naphthoyl, 1 or 2-naphthalenylmethyl and naphthalene-1-yl sulfonyl/naphthalene-2-yl sulfonyl indoleaminoguanidine hydrochlorides (1.0 mmol) were stirred with sodium bicarbonate (1.0 mmol) in water (10 ml) for 30 minutes at room temperature to afford 1 or 2-naphthoyl, 1 or 2-naphthalenylmethyl and naphthalene-1-yl sulfonyl/naphthalene-2-yl sulfonyl indoleaminoguanyl hydrazones.

UAMS-48

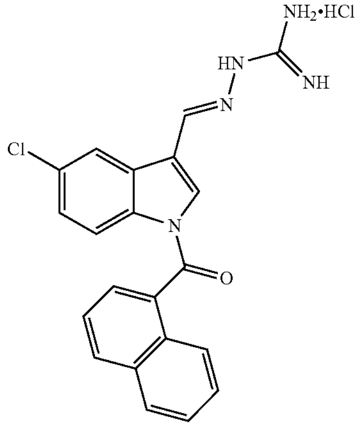

UAMS-48:

Mol. F: $C_{21}H_{17}C_{12}N_5O$, Mol. W: 426.34, $^1H$ NMR (DMSO-$d_6$, 400 MHz): δ 11.62 (brs, 3H, $NH_3^+$), 8.45 (d, J=2.0 Hz 1H,), 8.40 (d, J=8.4 Hz, 1H), 8.24 (d, J=8.4 Hz, 1H, ArH), 8.20 (s, 1H, =CH), 8.11 (d, J=8.0 Hz, 1H, C7-H), 7.89-7.91 (m, 2H, ArH and C2-H), 7.83 (d, J=8.4 Hz, 1H, C6-H), 7.55-7.73 (m, 6H, ArH) ppm. $^{18}C$ NMR (100 MHz, DMSO-$d_6$): δ 168.38, 155.60, 143.20, 135.03, 134.42, 133.55, 132.10, 131.21, 129.97, 129.13, 128.48, 128.33, 127.80, 127.34, 126.57, 125.58, 124.70, 122.73, 117.72, 116.33 ppm.

UAMS-61

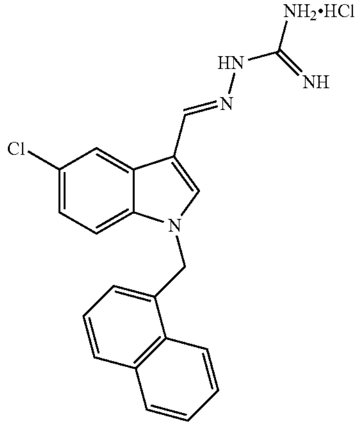

UAMS-61:

Mol.F: $C_{21}H_{19}Cl_2N_5$; Mol. W: 412.32; $^1H$ NMR (400 MHz, DMSO-$d_6$): δ 11.46 (brs, 3H, $NH_3^+$), 8.36 (s, 1H), 8.29 (s, 1H), 8.11 (d, J=7.4 Hz, 1H), 8.05-7.94 (m, 2H), 7.90 (d, J=7.9 Hz, 1H), 7.60 (dd, J=11.2, 6.5 Hz, 3H), 7.48-7.38 (m, 2H), 7.27 (d, J=8.8 Hz, 1H), 6.93 (d, J=6.8 Hz, 1H), 6.00 (s, 2H) ppm. $^{13}C$ NMR (100 MHz, DMSO-$d_6$): δ 155.28, 148.08, 144.42, 136.31, 134.27, 133.75, 133.29, 132.88, 132.03, 130.81, 130.38, 129.04, 126.64, 125.73, 125.18, 124.60, 123.80, 122.56, 112.89, 110.60, 48.01 ppm.

UAMS-64

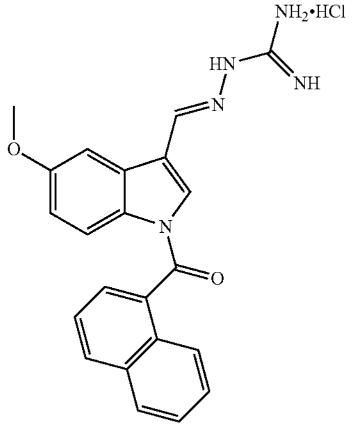

UAMS-64:

Mol. F: $C_{22}H_{20}ClN_5O_2$; Mol. W: 421.88, $^1H$ NMR (400 MHz, DMSO-$d_6$): δ 11.61 (brs, 3H, $NH_3^+$), 8.31 (d, J=9.0 Hz, 1H), 8.29-8.20 (m, 2H), 8.13 (d, J=7.6 Hz, 1H), 7.88 (dd, J=7.1, 1.1 Hz, 1H), 7.82 (dd, J=8.3, 5.5 Hz, 2H), 7.77 (s, 1H), 7.65 (m, 5H), 7.14 (dd, J=9.1, 2.6 Hz, 1H), 3.90 (s, 3H, $OCH_3$) ppm. $^{13}C$ NMR (100 MHz, DMSO-$d_6$): δ 168.14, 157.43, 155.59, 143.58, 133.53, 133.26, 131.80, 131.66, 130.91, 129.97, 129.11, 128.40, 128.26, 127.42, 127.30, 125.61, 124.67, 117.09, 116.90, 114.41, 106.49, 55.92 ppm.

UAMS-65

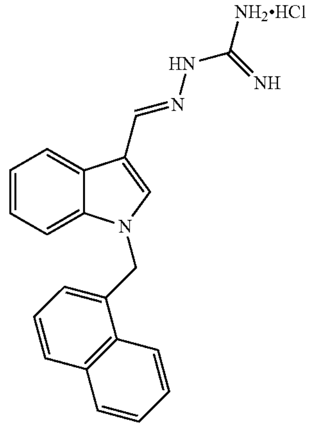

UAMS-65:

Mol. F: $C_{21}H_{20}ClN_5$; Mol. W: 377.87, $^1H$ NMR (400 MHz, DMSO-$d_6$): δ 11.80 (brs, 3H, $NH_3^+$), 8.38 (d, J=7.4 Hz, 1H), 8.35 (s, 1H), 8.14 (d, J=7.4 Hz, 1H), 8.03-7.96 (m, 1H), 7.95 (s, 1H), 7.88 (d, J=8.2 Hz, 1H), 7.63-7.49 (m, 4H), 7.43-7.36 (m, 2H), 7.28-7.17 (m, 2H), 6.93 (d, J=7.0 Hz, 1H), 5.97 (s, 2H, $CH_2$) ppm. $^{13}C$ NMR (100 MHz, DMSO-$d_6$): δ 155.26, 144.67, 137.74, 135.17, 133.73, 133.12, 130.84, 129.09, 128.60, 127.02, 126.55, 125.92, 125.18, 124.86, 123.58, 123.54, 123.24, 121.64, 110.89, 47.80 ppm.

UAMS-66

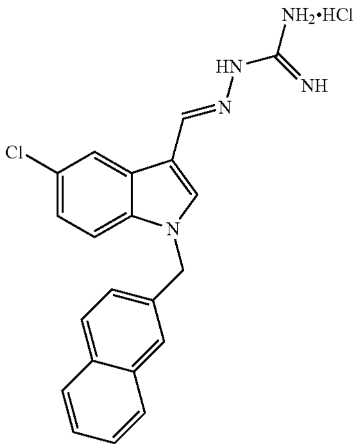

UAMS-66:

Mol. F: $C_{21}H_{19}Cl_2N_5$; Mol. W: 412.32, $^1$H NMR (400 MHz, DMSO-$d_6$): δ 11.86 (brs, 3H, $NH_3^+$), 8.40-8.32 (m, 2H), 8.22 (s, 1H), 7.92-7.81 (m, 3H), 7.80 (s, 1H), 7.61 (d, J=8.8 Hz, 2H), 7.54-7.45 (m, 3H), 7.38 (dd, J=8.5, 1.5 Hz, 1H), 7.23 (dd, J=8.8, 2.1 Hz, 1H), 5.64 (s, 2H, $CH_2$) ppm. $^{13}$C NMR (100 MHz, DMSO-$d_6$): δ 155.28, 144.38, 136.64, 135.93, 135.00, 133.17, 132.77, 128.87, 128.11, 128.00, 126.91, 126.61, 126.59, 126.29, 125.85, 125.65, 123.59, 122.01, 112.77, 110.45, 50.22 ppm.

UAMS-68

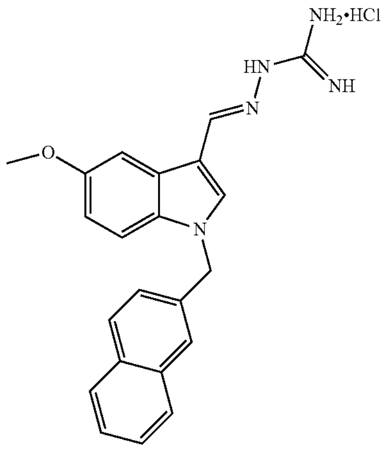

UAMS-68:

Mol. F: $C_{22}H_{22}ClN_5O$; Mol. W: 407.90, $^1$H NMR (400 MHz, DMSO-$d_6$): δ 11.78 (brs, 3H, $NH_3^+$), 8.37 (s, 1H), 8.09 (s, 1H), 7.90-7.81 (m, 4H), 7.79 (s, 1H), 7.70 (d, J=2.4 Hz, 1H), 7.48 (td, J=9.5, 5.1 Hz, 4H), 7.37 (dd, J=8.5, 1.4 Hz, 1H), 6.85 (dd, J=8.9, 2.4 Hz, 1H), 5.59 (s, 2H, $CH_2$), 3.81 (s, 3H, $OCH_3$) ppm. $^{13}$C NMR (100 MHz, DMSO-$d_6$): δ 155.41, 155.31, 144.93, 135.44, 135.36, 133.18, 132.75, 132.43, 128.79, 128.08, 128.00, 126.87, 126.54, 126.20, 125.67, 112.96, 111.95, 110.29, 105.09, 55.90, 50.22 ppm.

UAMS-69

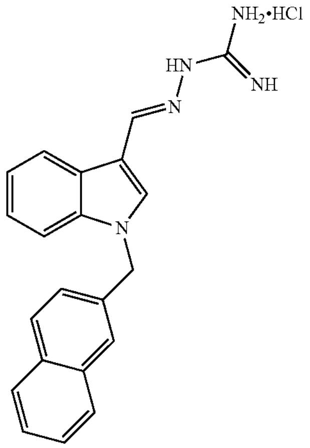

UAMS-69:

Mol. F: $C_{21}H_{20}ClN_5$; Mol. W: 377.87, $^1$H NMR (400 MHz, DMSO-$d_6$): δ 11.82 (brs, 3H, $NH_3^+$), 8.38 (s, 1H), 8.35 (d, J=7.7 Hz, 1H), 8.14 (s, 1H), 7.85 (m, 4H), 7.80 (s, 1H), 7.57 (d, J=8.0 Hz, 1H), 7.52-7.47 (m, 3H), 7.39 (d, J=8.4 Hz, 1H), 7.19 (dd, J=14.4, 7.6 Hz, 2H), 5.63 (s, 2H) ppm. $^{13}$C NMR (100 MHz, DMSO-$d_6$): δ 155.23, 144.66, 137.39, 135.31, 135.28, 133.18, 132.75, 128.81, 128.09, 128.00, 126.88, 126.55, 126.26, 125.72, 124.99, 123.46, 123.18, 121.56, 111.10, 110.76, 50.06 ppm.

UAMS-70

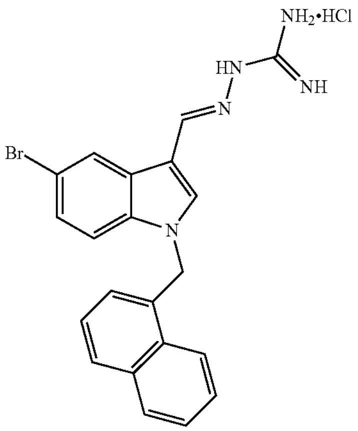

UAMS-70:

Mol. F: $C_{21}H_{19}BrClN_5$, Mol. W: 456.77, $^1$H NMR (400 MHz, DMSO-$d_6$): δ 11.80 (brs, 3H, $NH_3^+$), 8.49 (d, J=1.9 Hz, 1H), 8.33 (s, 1H), 8.15-8.08 (m, 1H), 8.03-7.95 (m, 2H), 7.87 (dd, J=15.1, 7.3 Hz, 1H), 7.63-7.50 (m, 4H), 7.45-7.33 (m, 3H), 6.91 (d, J=7.0 Hz, 1H), 5.99 (s, 2H) ppm. $^{13}$C NMR (100 MHz, DMSO-$d_6$): δ 155.34, 144.38, 136.55, 136.31, 133.74, 132.83, 130.78, 129.11, 128.70, 127.06, 126.59, 126.34, 126.32, 125.94, 125.14, 124.89, 123.50, 114.72, 113.20, 110.51, 47.99 ppm.

Results (i) Expansion of Chemical Library and Identification of Indole-Aminoguanidine Analogues as Inhibitors of Hpol κ.

Figure 1B:
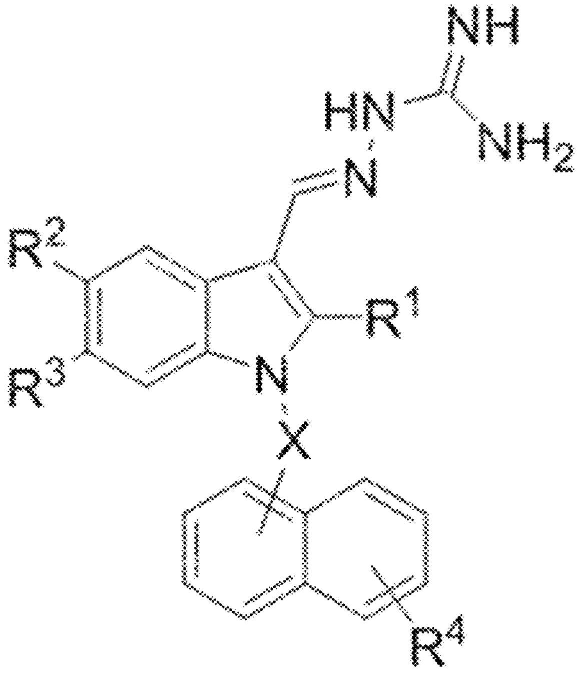
Figure 1C:
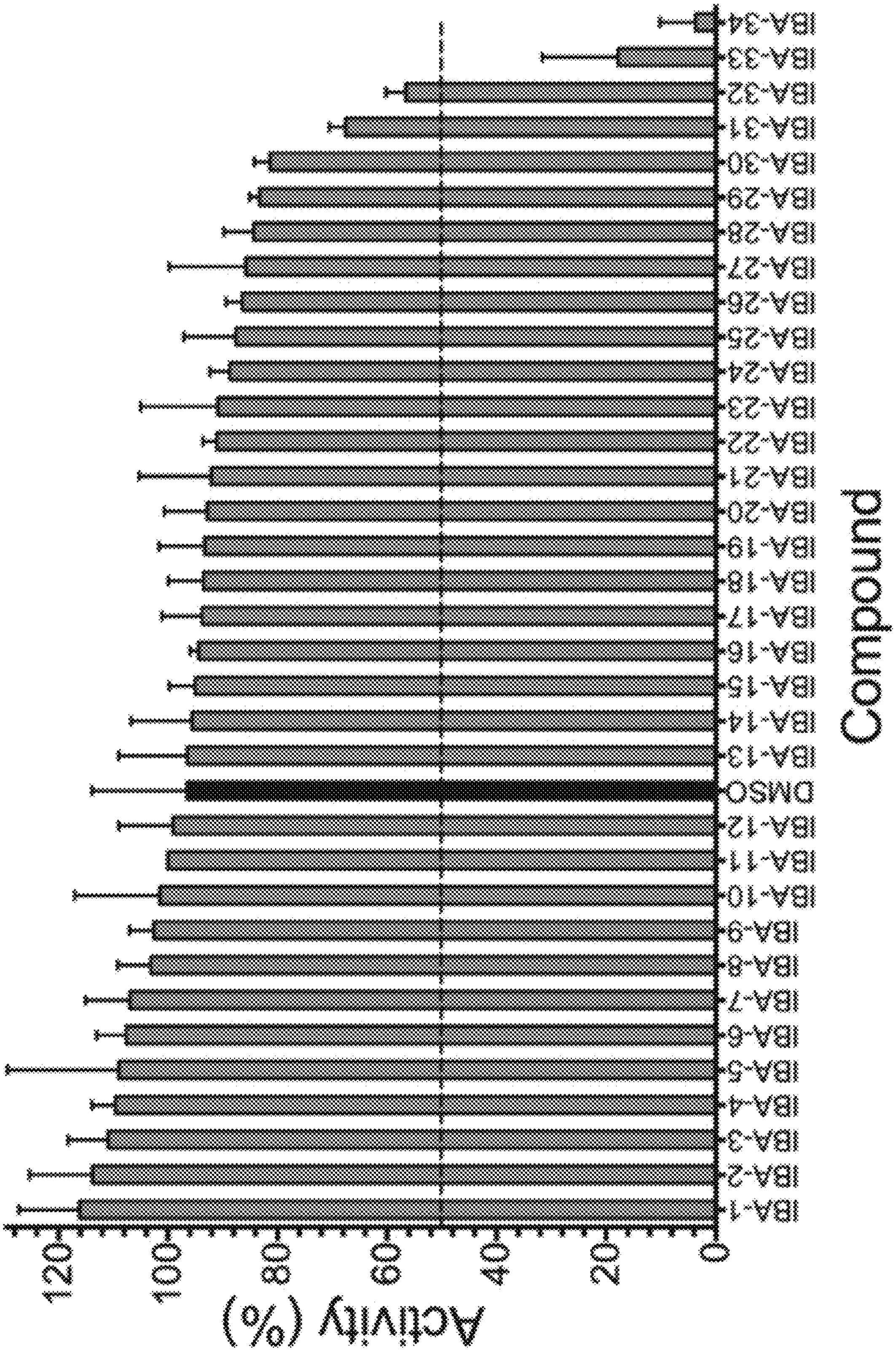
Figure 1D:
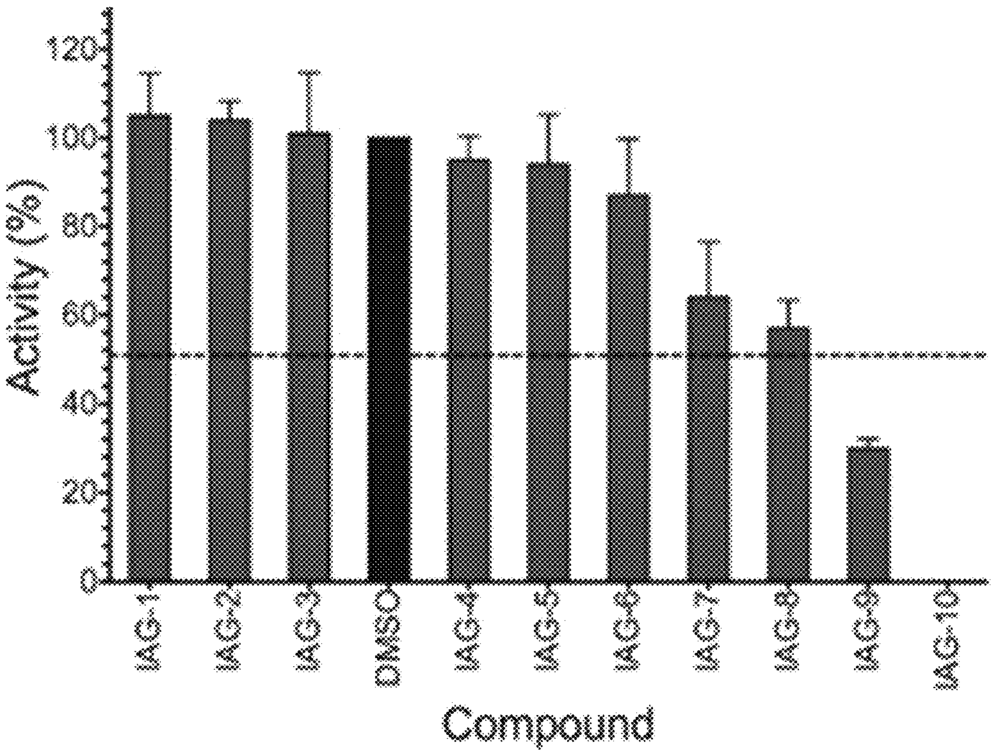
Figure 2A:
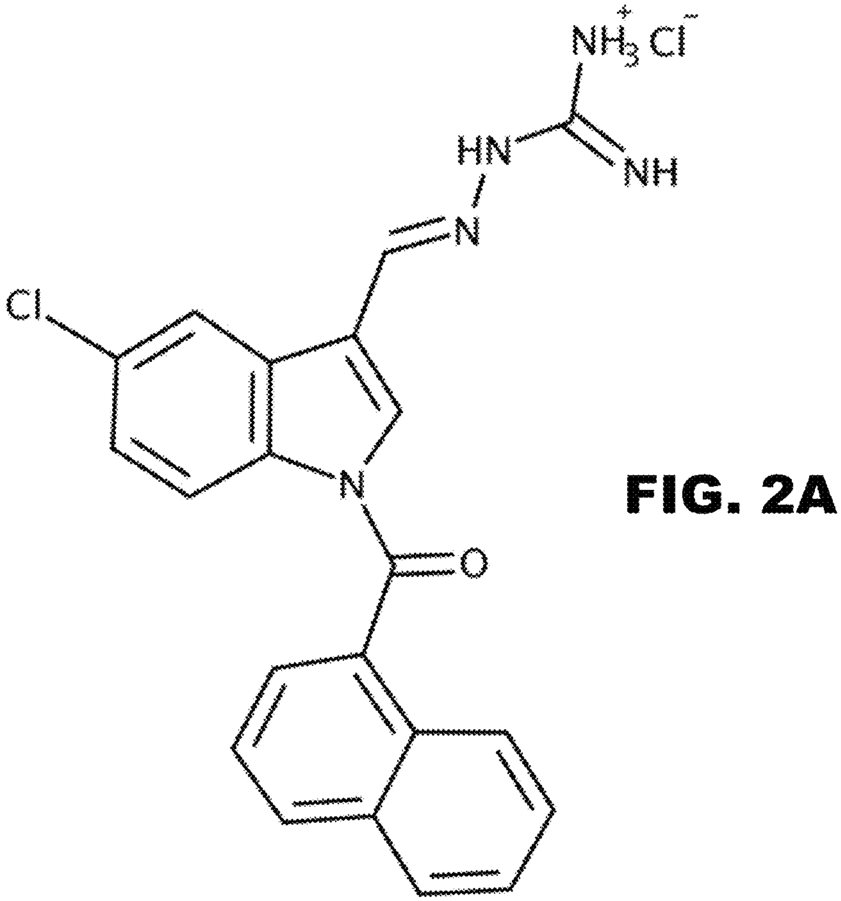
FIG. 2A-2D show IAG-10 is a selective inhibitor of hpol κ.

As with previous work, a fluorescence based assay developed at NIH to screen for pol inhibitors was used. Briefly, the assay involves pol-catalyzed extension of an unlabeled DNA primer, as well as a 5-carboxytetramethylrhodamine (TAMRA)-labeled (displaced) strand, both annealed to a BHQ-labeled template. Primer extension leads to displacement of the TAMRA-labeled strand and an increase in TAMRA fluorescence due to separation from the BHQ-labeled template. The rate of increase in fluorescence is reduced or prevented if the pol is inhibited. This assay had led to our successful identification of IBA analogues as inhibitors of hpol κ activity. In the present study focused on the identification of hpol κ inhibitors and expanded the IBA scaffold library to include compounds in which the barbituric acid moiety had been replaced with an aminoguanidine moiety (FIG. 1A and FIG. 1B). A total of 44 IBA and IAG derivatives were tested at a final concentration of 40 μM for inhibition of hpol κ activity. Several compounds inhibited enzyme activity by more than 50% in the initial screen (FIG. 1C and FIG. 1D). The chemical structures and a summary of the results of the screen against hpol κ may be found in Tables 1 and 2. Of the compounds tested, IAG-10 exerted the greatest inhibitory action against hpol κ (FIG. 1D). The chemical structure of IAG-10 is reminiscent of the most potent inhibitors of hpol κ identified in our previous work in that the indole substituent is a N-naphthoyl moiety (FIG. 2A). Replacement of the barbituric acid moiety with an aminoguanidine moiety is of interest because of the improved water-solubility afforded by the latter group. Next, the structure-activity relationships important for inhibition of hpol κ by the IAG compounds were investigated.

(ii) Structure—Activity Studies with the IAG Derivatives.

Analogue (E)-2-((1-(1-naphthoyl)-5-chloro-1H-indol-3-yl) methylene)hydrazine-1-carboximidamide hydrochloride (IAG-10) exhibited the most potent inhibitory action against hpol κ ($IC_{50}$=7.2 μM, Table 2). The $IC_{50}$ value for 13 IAG derivatives (Table 2) related to IAG-10 were then measured. While none of the other chemical changes improved activity over that of IAG-10, some interesting trends emerged. The presence of a halogen moiety at the fifth position of the indole ring combined with an indolic N-naphthoyl (IAG-10 and IAG-9) or N-naphthyl group (IAG-8, IAG-13, and IAG-7) generated the top five most potent inhibitors with $IC_{50}$ values ranging from 7.2 to 24.2 μM. Replacement of the indole N-1-(1-naphthoyl) moiety in IAG-10 with an isomeric N-1-(2 naphthoyl) moiety (IAG-9) reduced inhibitory potency against hpol κ by about half ($IC_{50}$=18.8 μM) (Table 2). Replacement of the 5-chloro substituent on the indole ring with a methoxy group (IAG-2) in IAG-10 decreased potency against the target ($IC_{50}$=68.6 μM, Table 2). Introducing a methyl group at the 2-position of the indole ring also reduced potency (IAG-1; $IC_{50}$=84.6 μM) against hpol κ, and removal of the N-1-(1-naphthoyl) moiety from the indole ring (IAG-11) completely eliminated inhibitory activity ($IC_{50}$>200 μM; Table 2). Replacement of the indole N-1-(1-naphthoyl) substituent in IAG-10 with either an N-1-(1-naphthylidene) or N-1-(2-naphthylidene) moiety (IAG-7 and IAG-13, respectively) led to reduced inhibitory potency against hpol κ (24.2 and 22.7 μM, respectively), and replacement of the indole 5-chloro substituent in IAG-7 with bromo, methoxy, or hydrogen afforded analogues with $IC_{50}$ values in the range 22.3-52.0 μM. Similarly, replacement of the indole 5-chloro substituent in IAG-13 with methoxy or hydrogen resulted in analogues with reduced potency (IAG-5 and IAG-4 $IC_{50}$ values of 43.7 and 48.3 μM, respectively). Thus, the presence of 5-chloro and N-naphthoyl/naphthyl indole substituents combined to inhibit hpol κ with the greatest potency. This is similar to previous observations for IBA-mediated inhibition of hpol η. Next, the selectivity of IAG-10 for hpol κ was tested by testing for inhibition of other DNA pols.

(iii) Selectivity of Hpol κ Inhibition by IAG-10

Figure 2B:
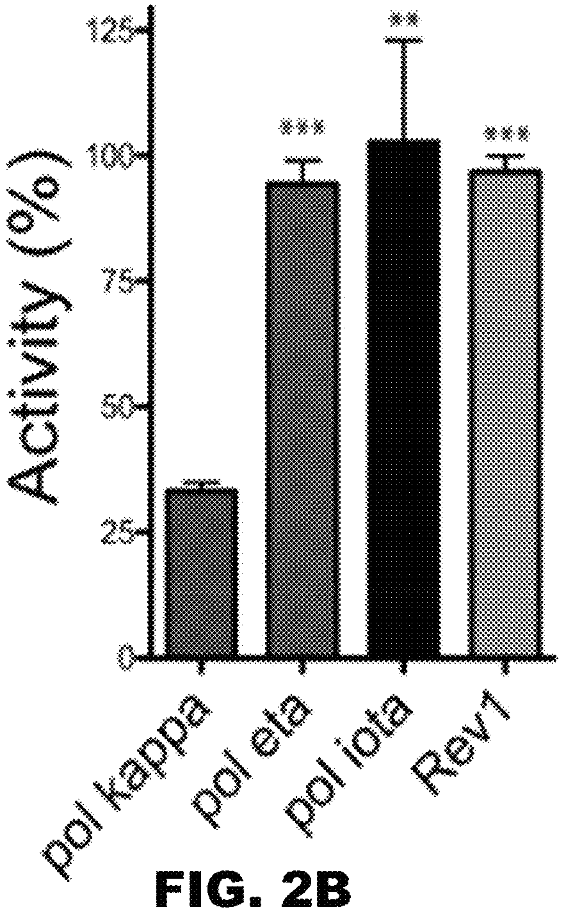
Figure 2C:
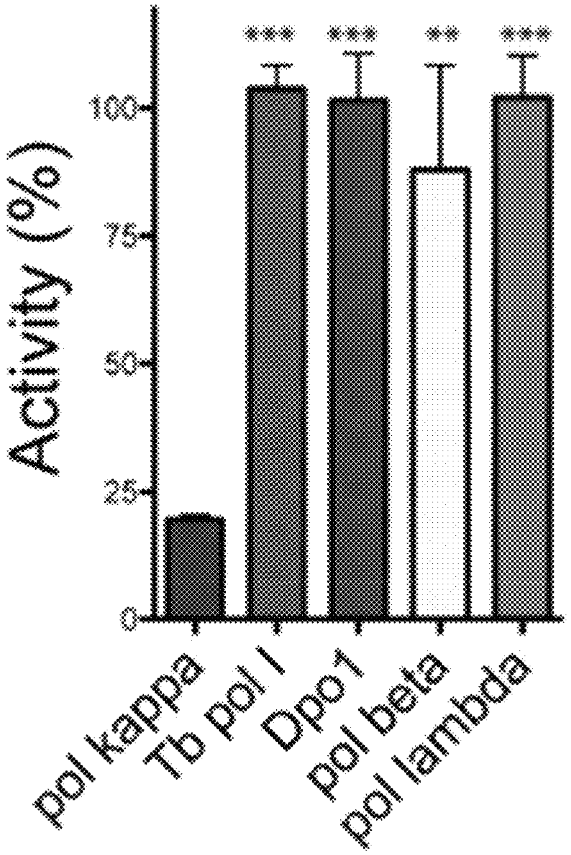
Figure 2D:
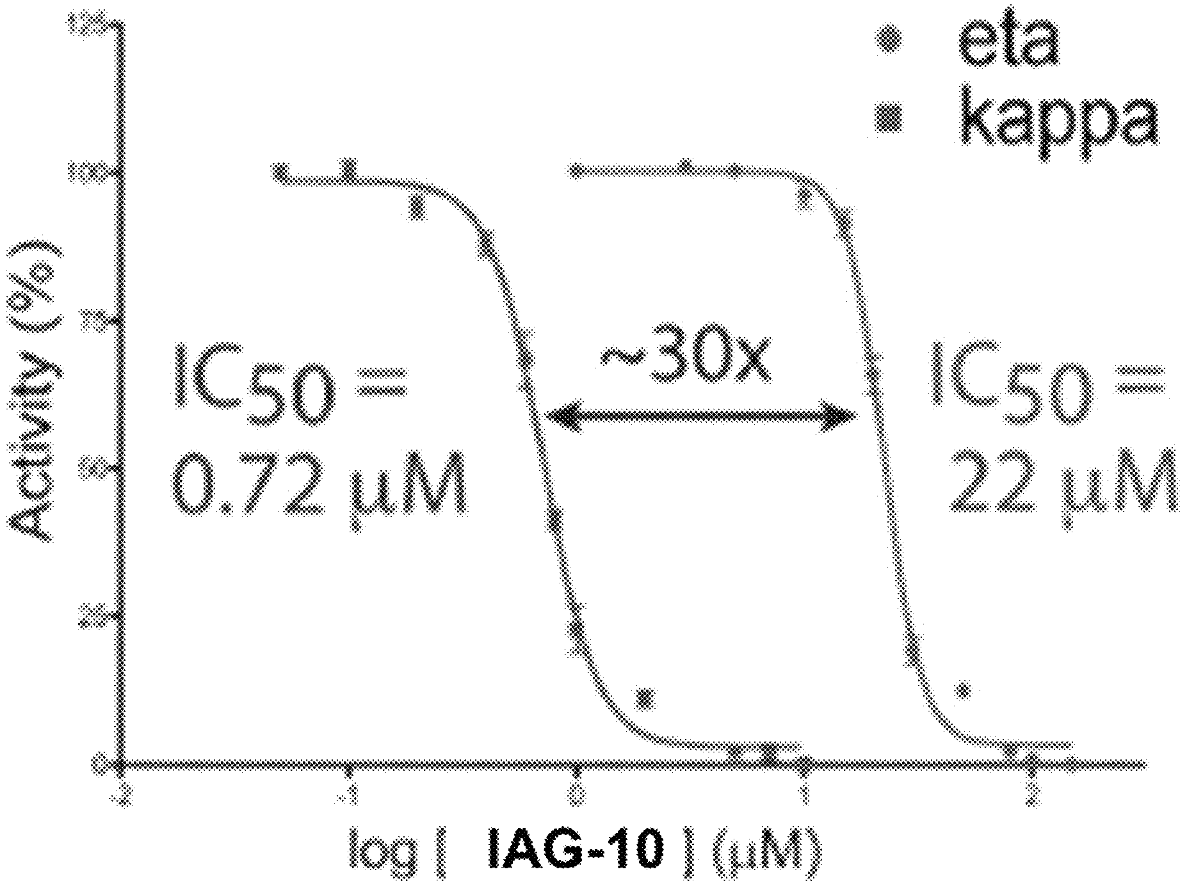

Previously, it was shown that several indole-derived compounds inhibit the DNA polymerase activity of hpol κ, but in every instance, those molecules inhibited hpol (or another TLS pol) more potently than hpol κ. IAG-10 (10 μM) was tested for activity against the other three human Y-family members, but only hpol κ was inhibited under these conditions (FIG. 2A and FIG. 2D). Then, the activity of enzymes from different pol families (A, B, and X) in the presence of IAG-10 were measured and found that, once again, only hpol κ activity was inhibited (FIG. 2B). These results make IAG-10 one of the most selective inhibitors of hpol κ identified to date.

(iv) IAG-10 Disrupts Hpol κ Binding to Primer-Template DNA

Figure 3A:
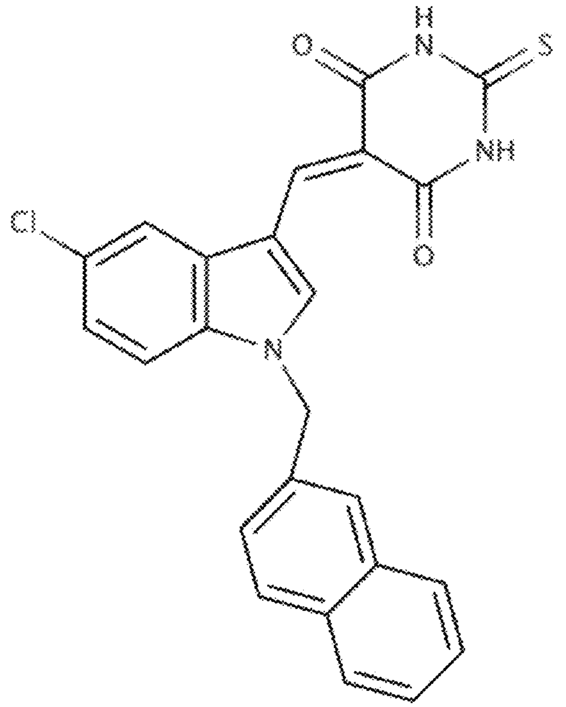
FIG. 3A-3C show indole-derived compounds decrease the affinity of hpol κ for primer-template DNA.
Figure 3B:
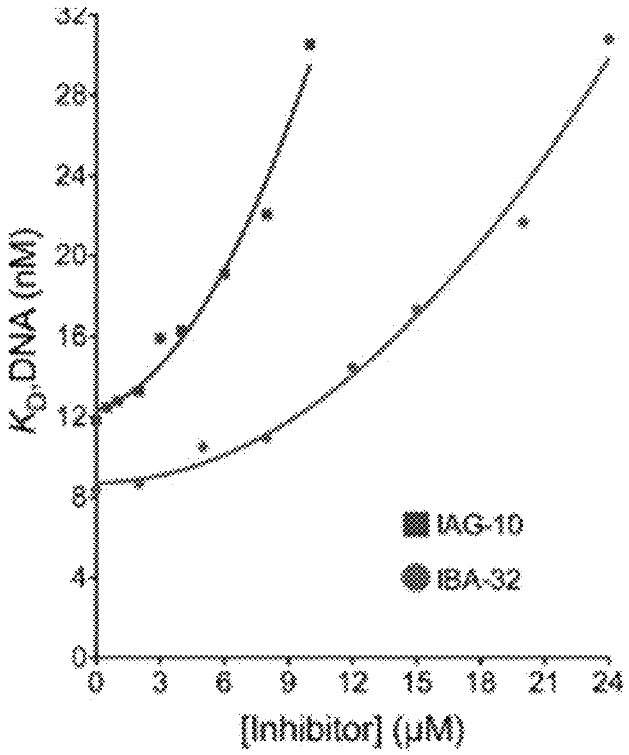
Figure 3C:
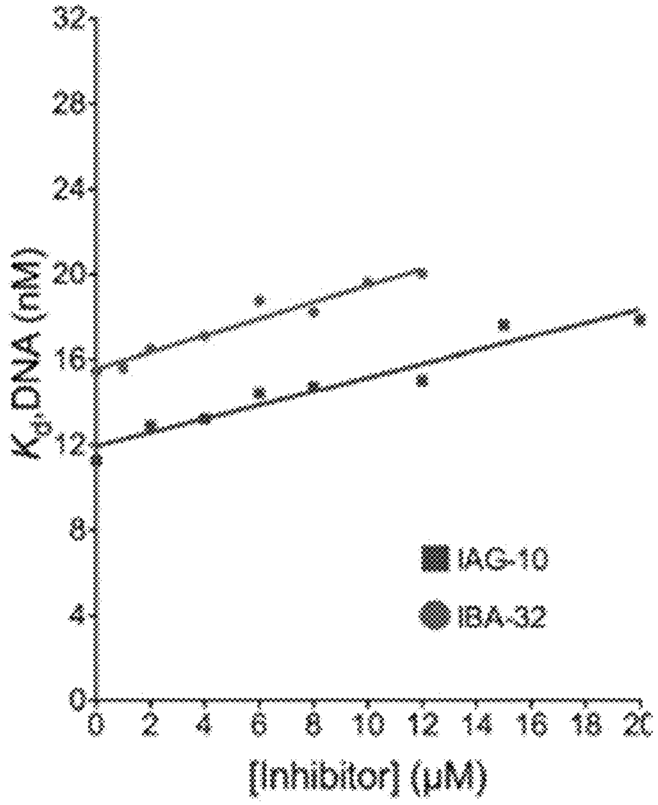

Next, the ability of IAG derivative IAG10 and IBA derivative IBA-32 (FIG. 3A) was investigated to disrupt hpol binding to primer-template DNA (p/t-DNA). The equilibrium dissociation constant ($K_{D,DNA}$) was determined by titrating protein (0-400 nM) into a solution containing FAM-labeled p/t-DNA (2 nM) at various concentrations of inhibitor and measuring changes in fluorescence anisotropy. Fitting the results to a quadratic equation produced an estimate of DNA binding affinity for hpol κ in the presence of the inhibitors. Both compounds IAG-10 and IBA-32 inhibited hpol κ binding to p/t-DNA (FIG. 3B). The equilibrium dissociation constant ($K_{D,DNA}$) increased approximately 2- to 3-fold (100-200%) at concentrations of inhibitor near the $IC_{50}$ measured for inhibition of pol activity. The increase in the $K_{D,DNA}$ that occurred as a function of inhibitor concentration clearly followed a nonlinear trend upward, indicative of an allosteric effect of the inhibitors on pol binding to DNA. The effect of IAG-10 and IBA-32 on DNA binding by hpol η was also measured. In contrast to what was observed with hpol κ, there is only about a 20-30% increase in the $K_{D,DNA}$ at concentrations of inhibitor near the $IC_{50}$ for inhibition of pol activity (FIG. 3C). Also, the small effect of the inhibitors on the affinity of hpol for p/t-DNA is linear in nature. These results suggest that the effect of IAG-10 and IBA-32 on the DNA binding affinity of hpol κ is quite distinct from the modest effects on DNA binding observed for hpol η indicative of a different mechanism of inhibition for the two enzymes.

(v) Effect of Enzyme and DNA Concentration on the Measured $IC_{50}$ Against Hpols η and κ.

Figure 4A:
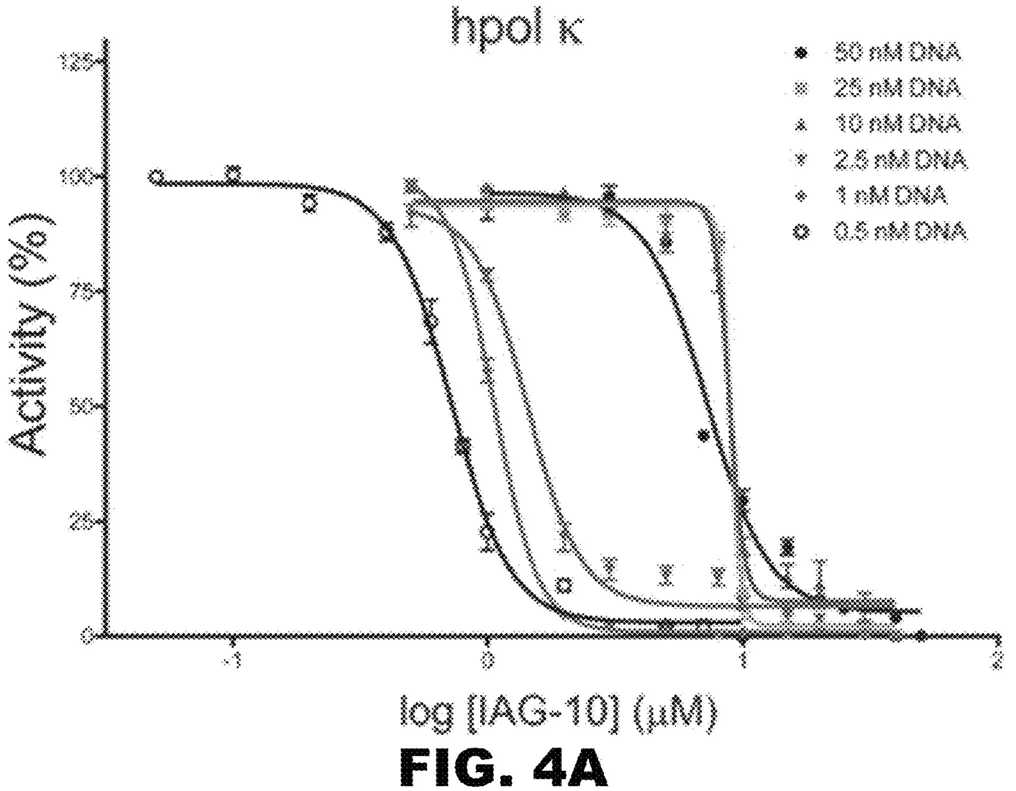
FIG. 4A-4B provide the $IC_{50}$ value for inhibition of hpol κ by IAG-10 is sensitive to the concentration of enzyme and DNA.
Figure 4B:
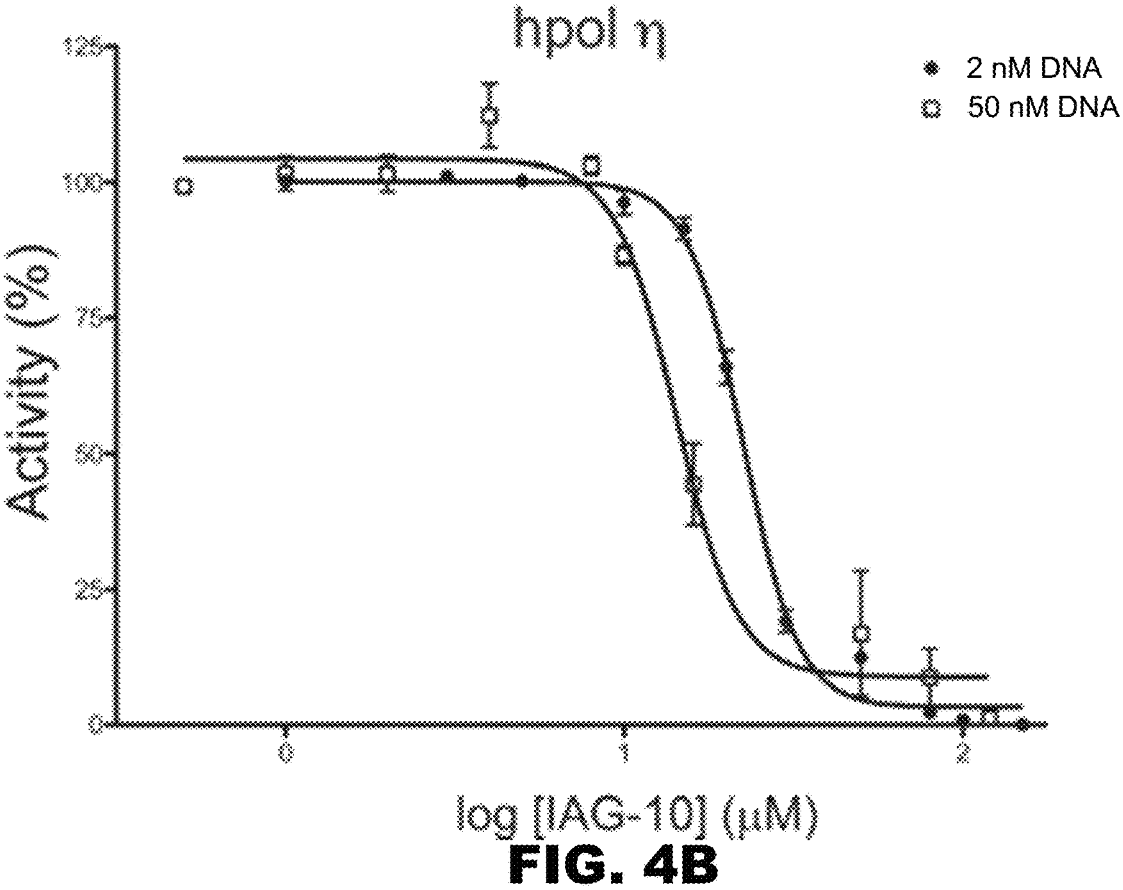

The impact of IAG-10 on the affinity of hpol κ for DNA was an important insight and one that had not been observed previously with MK-886. It was reasoned that decreasing the concentration of either enzyme or DNA, might affect the $IC_{50}$ value by shifting the equilibrium away from the formation of binary hpol c: DNA complex and toward the enzyme-inhibitor complex. To investigate this idea, the concentration of hpol and p/t-DNA was varied in the reaction mixture and measured the $IC_{50}$ value for IAG-10. Decreasing the enzyme and DNA in solution led to a dramatic decrease in the $IC_{50}$ for IAG-10 against hpol κ (FIG. 4A). At the lowest concentration of hpol κ and DNA tested (0.1 and 0.5 nM, respectively), the $IC_{50}$ was 0.72 μM (FIG. 4A, open circles), an order of magnitude lower than that measured at p/t-DNA concentrations >10 nM. Then, similar experiments were performed with hpol η by varying the concentration of enzyme and DNA in the reaction mixture an determining the $IC_{50}$ value for IAG-10-mediated inhibition. Notably, the $IC_{50}$ value for inhibition of hpol η by IAG-10 increased slightly when the concentration of DNA and enzyme was decreased (FIG. 4B). These results were again supportive of IAG-10 inhibiting hpols η and κ through different modes of action with hpol κ being much more sensitive to destabilization of binary complex formation.

(vi) IAG-10 Inhibits Hpol κ and Hpol η Through Distinct Mechanisms of Action.

Figure 5A:
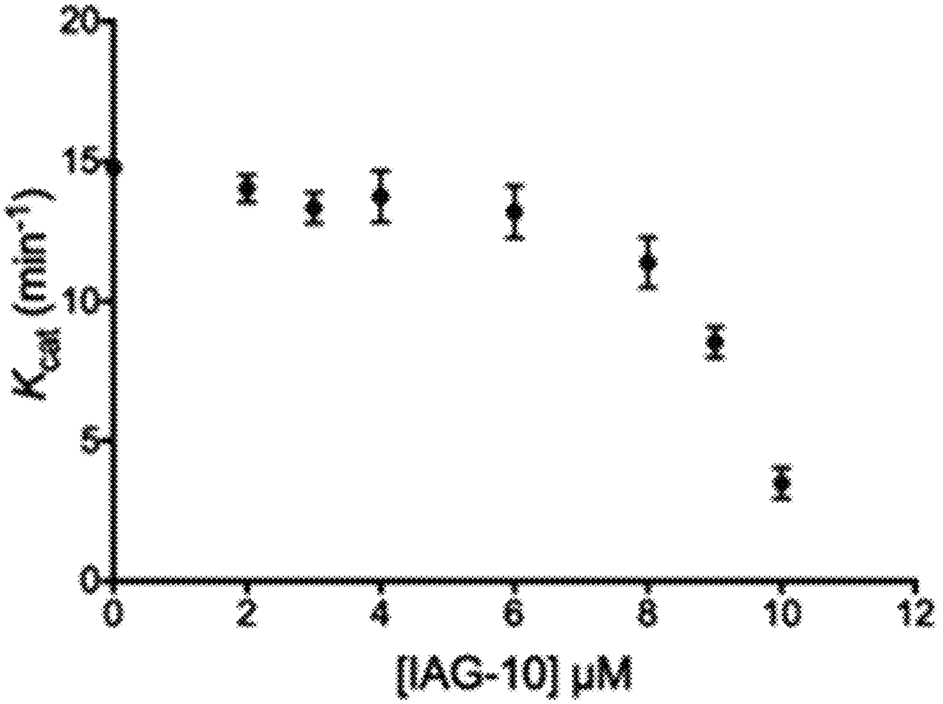
FIG. 5A-5F show steady-state kinetic analysis of the mechanism of pol inhibition by indole-derived compounds.
Figure 5B:
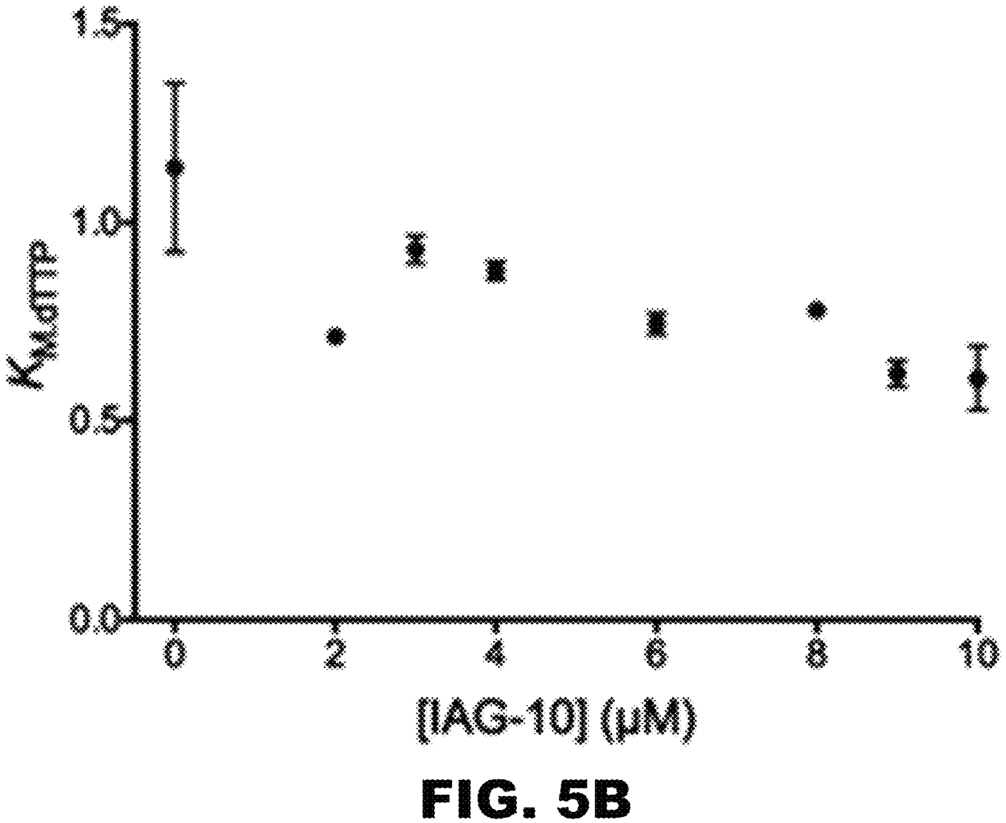
Figure 5C:
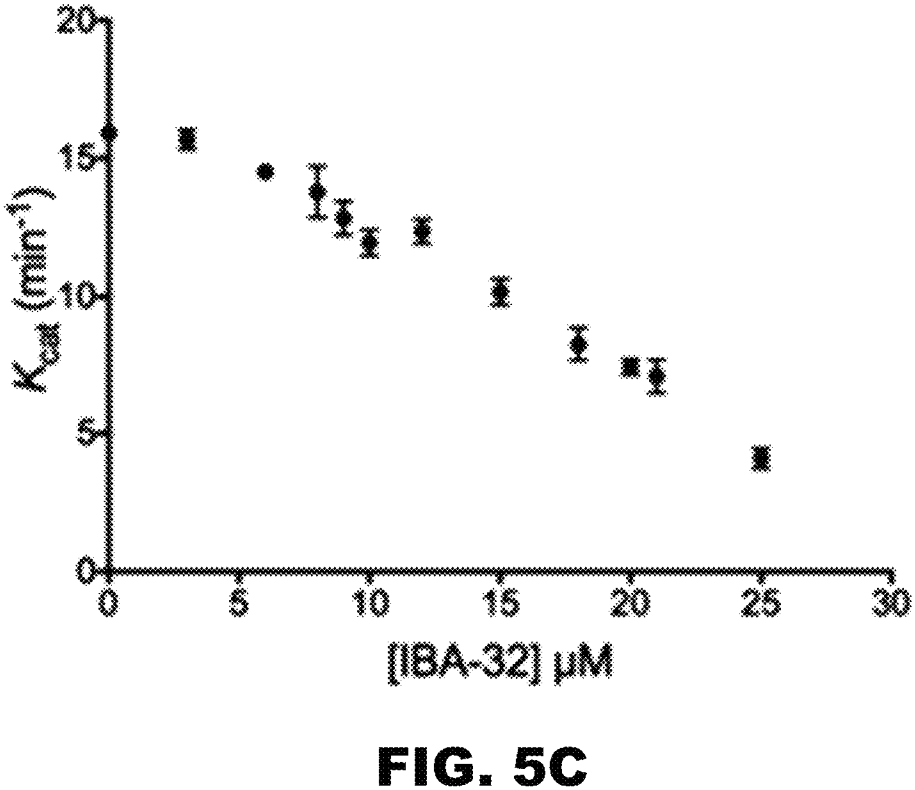
Figure 5D:
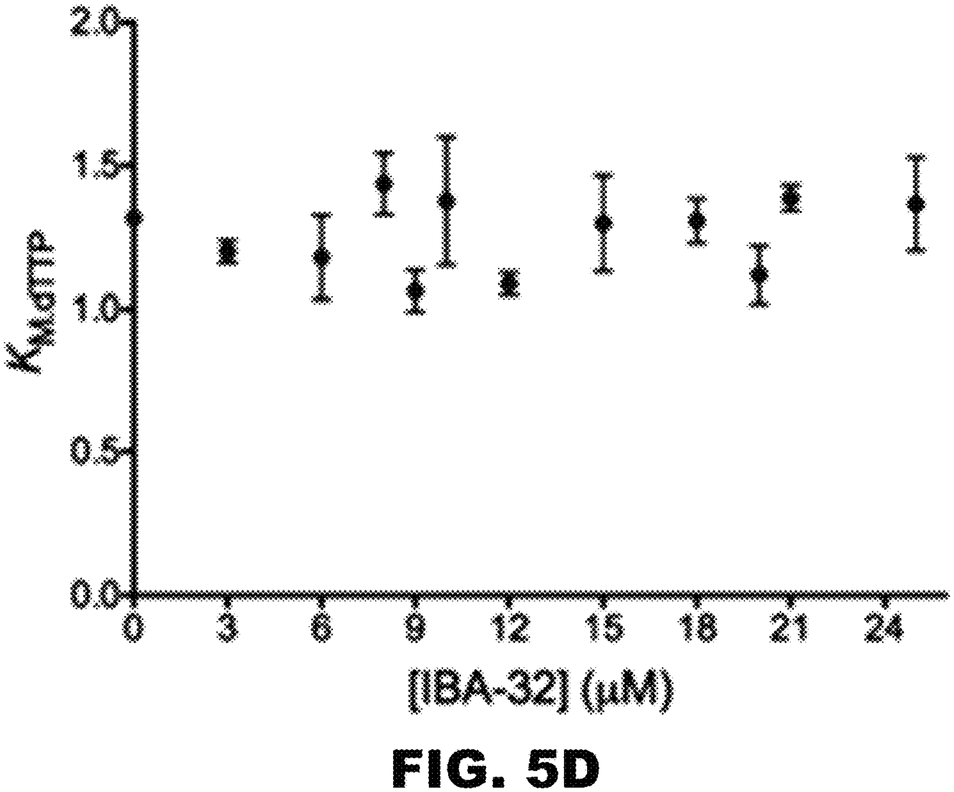
Figure 5E:
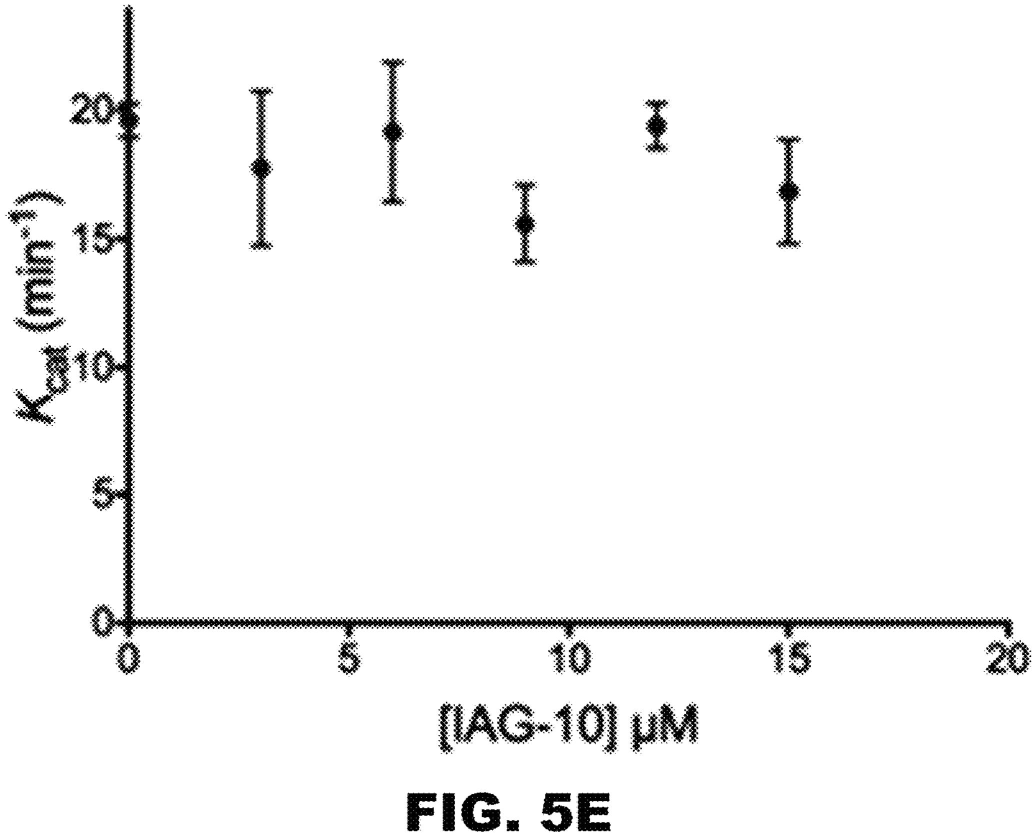
Figure 5F:
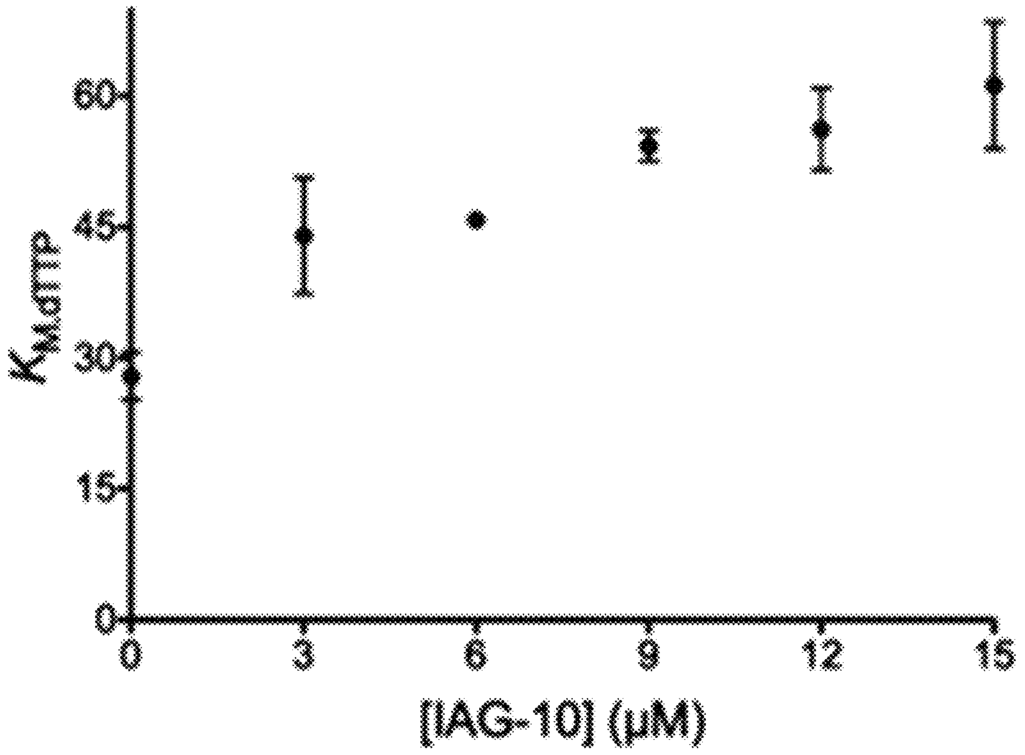

Next, the impact of IAG-10 and IBA-32 on nucleotide selection by hpol κ was examined. Steady-state kinetic analysis of nucleotide insertion in the presence of either IAG-10 or IBA-32 revealed that both compounds had a similar effect on hpol κ activity. The turnover number ($k_{cat}$) exhibited a sharp decrease when the concentration of IAG-10 exceeded the $IC_{50}$ value, whereas the Michaelis constant ($K_{M,dNTP}$) exhibited very little change at inhibitor concentrations in the range of 2-10 μM (FIG. 5A and FIG. 5B). The effect was somewhat less acute with IBA-32, but again, it was the $k_{cat}$ and not the $K_{dNTP}$ that was altered by the presence of the inhibitor (FIG. 5C and FIG. 5D). These results are consistent with a model for inhibition where IAG-10 impedes a step in the hpol κ catalytic cycle that occurs prior to nucleotide binding and are in direct contrast to those reported previously for IBA derivatives tested against hpol η. Previously, it was observed a nonlinear increase in the $K_{dNTP}$ when hpol η activity was measured in the presence of IBA-32. This led to the conclusion that IBA-32 inhibited hpol η through a partial competitive mechanism of action. A similar steady-state kinetic analysis was performed with hpol η and IAG-10. Intriguingly, there was no measurable change in the $k_{cat}$, but a linear increase in the Michaelis constant accompanied the increase in IAG-10 concentration (FIG. 5E and FIG. 5F). These results are consistent with a competitive mechanism of inhibition distinct from what was reported for IBA-32 but also quite different from that observed for hpol κ and IAG-10.

(vii) Chemical Footprinting Helps Identify Changes in Hpol κ Structure Induced by IAG-10

Figure 6A:
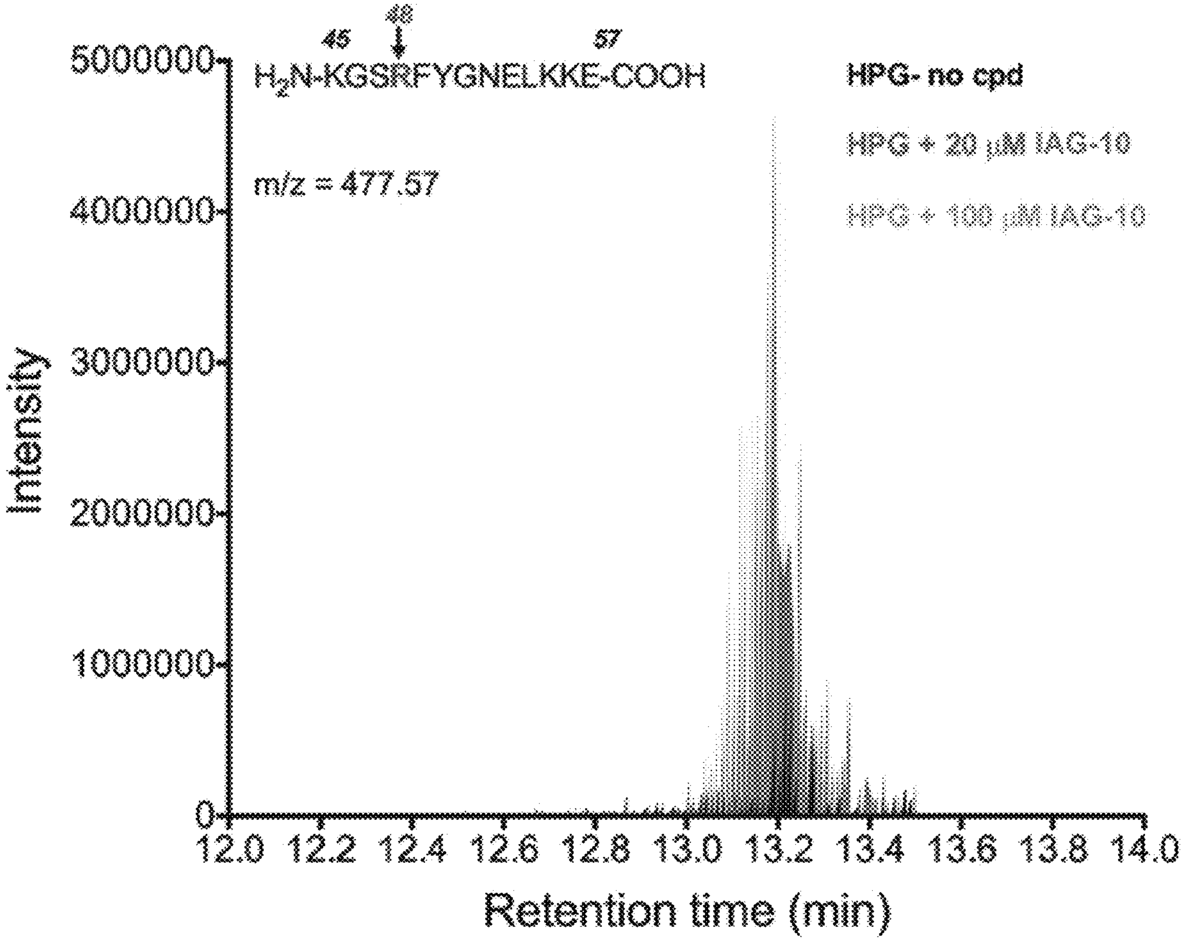
FIG. 6A-6D provide LC-MS analysis of HPG labeling which identified a possible binding interface for IAG-10 on hpol κ.
Figure 6B:
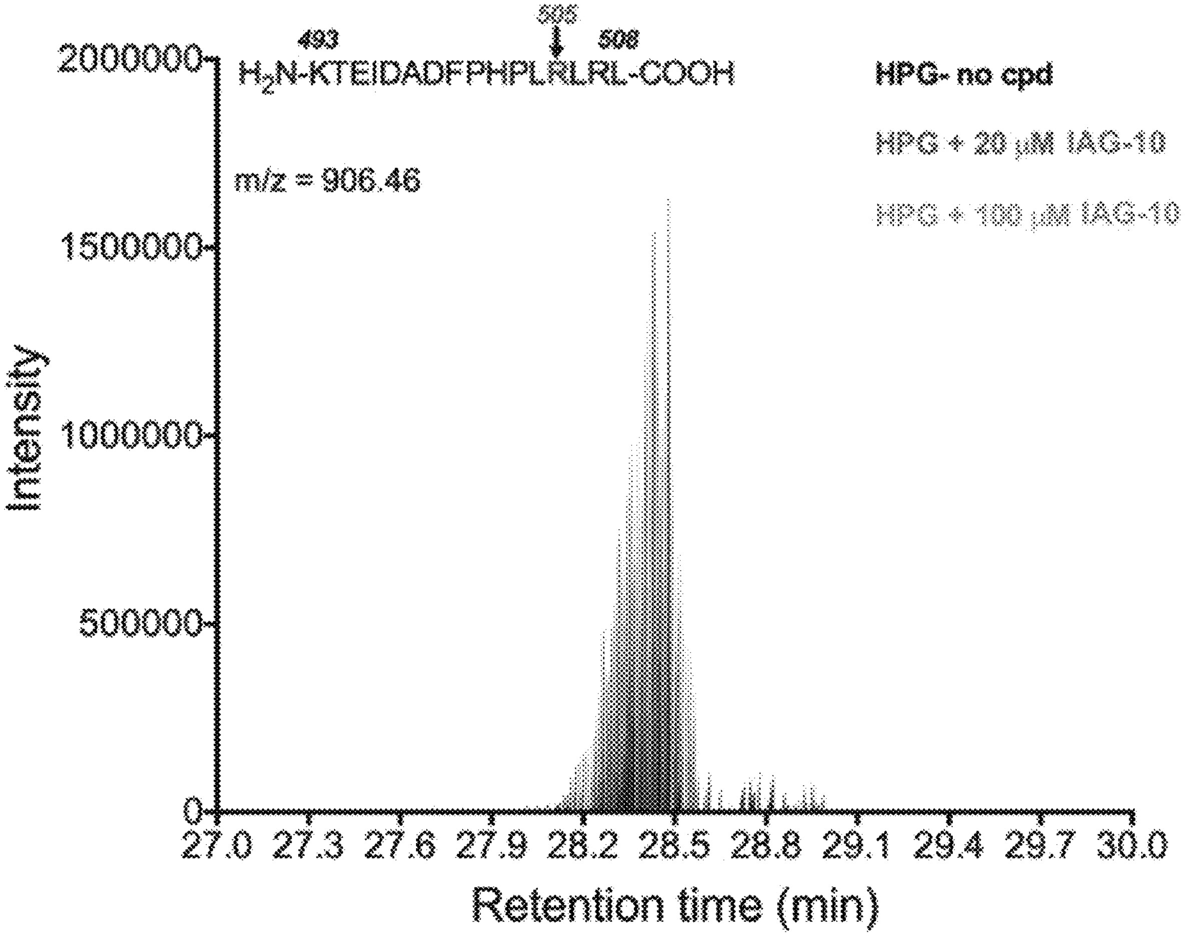
Figure 6C:
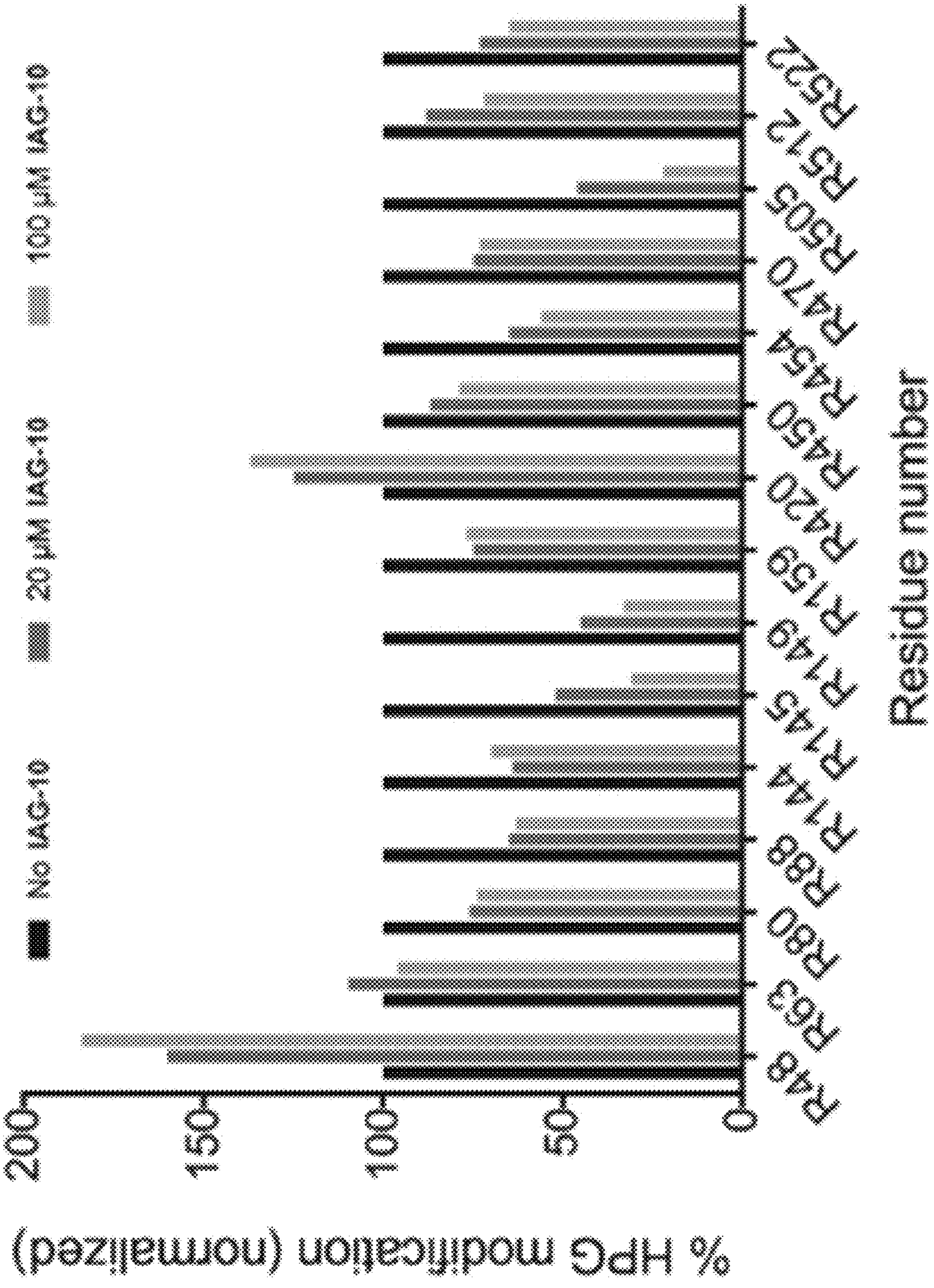
Figure 6D:
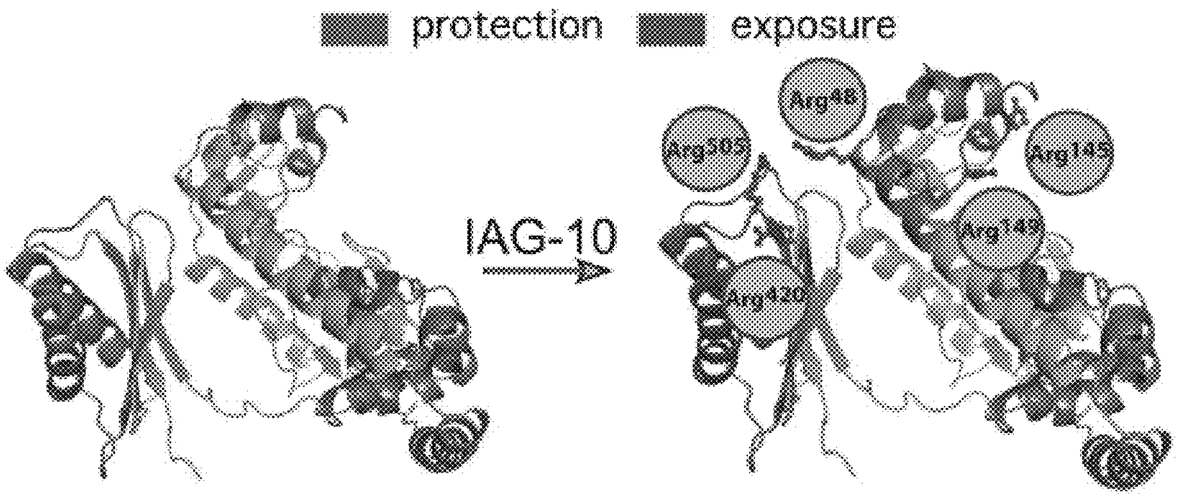

Next, Chemical footprinting was used in an effort to ascertain the binding site of IAG-10 on hpol κ. Recombinant hpol κ was incubated with the arginine-reactive probe HPG alone or in the presence of IAG-10 (20 and 100 μM). After quenching the reaction and gel electrophoresis, the modified protein was trypsin-digested, and the resulting peptides were analyzed by LC-MS. By quantifying the peak intensity of HPG-modified peptides as a fraction of the total intensity measured for peptides containing a given arginine residue, it was determined whether the addition of IAG-10 alters the reactivity of that site (FIG. 6A-6C). A decrease in the fraction of HPG-modified peptides was interpreted as evidence for protection from HPG-reactivity by IAG-10. 15 arginine residues were identified (out of 30 arginine residues occurring between amino acids 19-526) that were modified by HPG (FIG. 6C). Of those 15 residues, three of them (Arg145, Arg149, and Arg505) exhibited a >50% decrease in the fraction of HPG-modified peptides when IAG-10 was added to the reaction mixture (FIG. 6C). These three residues map to the finger and little finger domains of hpol κ (FIG. 6D) in a cleft similar to the one identified in our study with hpol η. Perhaps most striking of all was the large increase in the fraction of HPG-modified peptides containing Arg48 upon addition of IAG-10 (FIG. 6C).

The increase in HPG reactivity for Arg48 is indicative of increased exposure in the presence of IAG-10. Because Arg48 resides in the N-clasp, it is reasonable to assume that binding of IAG-10 disrupts contacts occurring between the N-clasp, finger, and little finger domains of hpol κ and results in a conformational change that exposes the N-clasp to solvent. Indeed, the N-clasp allows hpol κ to encircle the DNA substrate and is required for optimal polymerase activity. An important function of the N-clasp is to stabilize the position of the little finger domain, which makes the largest number of contacts with the DNA substrate. Loss of this stabilization would presumably impact DNA binding affinity.

(viii) IAG-10 Potentiates the Antiproliferative Effects of TMZ in a Target-Dependent Manner Earlier work has shown that hpol κ activity is important for cellular responses to alkylation damage, including abasic sites and $0^6$-methylguanine adducts produced by TMZ, and further, that the enzyme promotes TMZ-resistance in both in vitro and in vivo models of glioblastoma multiforme. The ability of IAG-10 to inhibit hpol c in the cellular context and also the potential of using IAG-10 or other potent hpol inhibitors as a potential way of enhancing the antiproliferative properties of TMZ was investigated. Toward this goal, clonogenic survival for hpol κ-proficient (wt HAP-1) and hpol κ-deficient (hpol κ knockout) cell lines were treated with the chemotherapeutic drug TMZ, either alone or in combination with IAG-10.

Figure 7A:
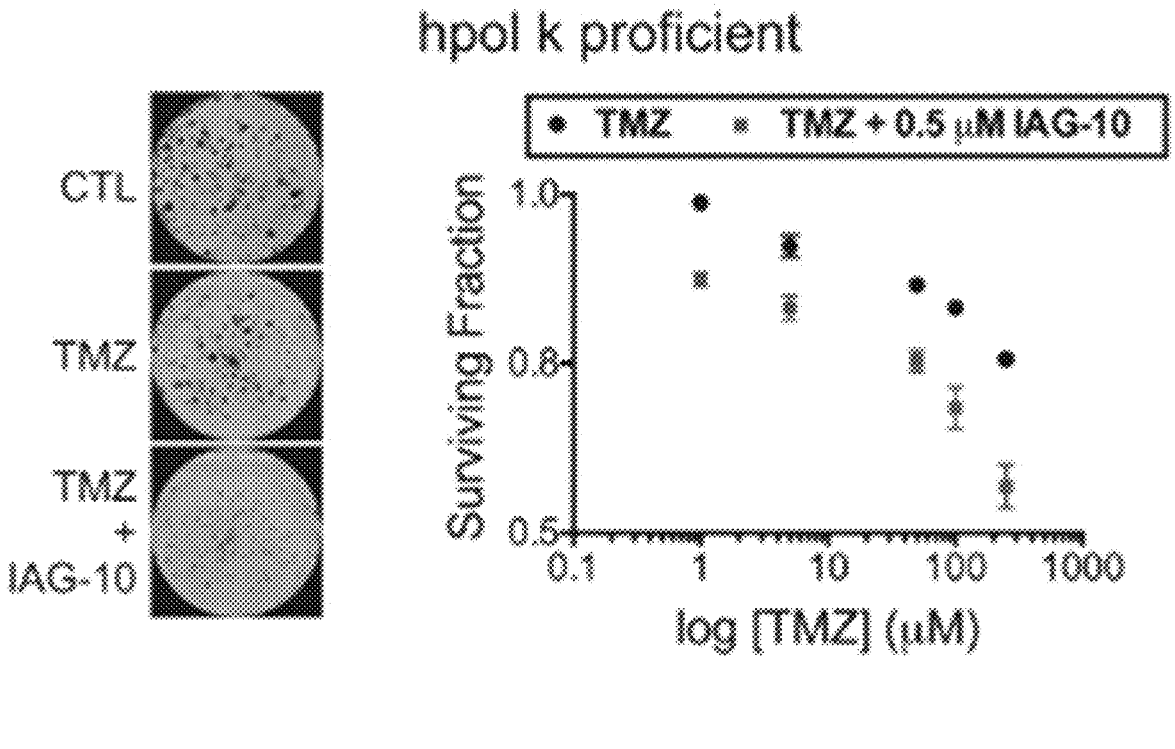
FIG. 7A-7E show IAG-10 potentiates the antiproliferative and DNA damaging effects of TMZ. Clonogenic assays were performed to assess the effect of IAG-10 on the survival of HAP-1 cells (both hpol κ-proficient and hpol κ-deficient) upon treatment with increasing concentration of TMZ.
Figure 7B:
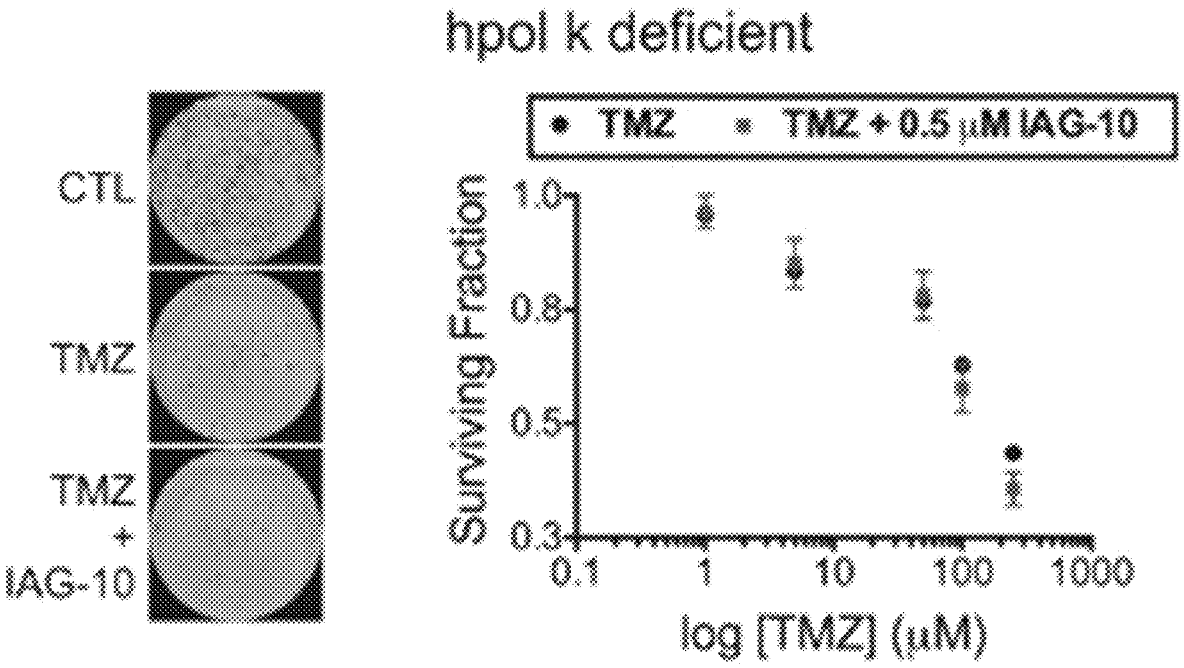
Figure 7C:
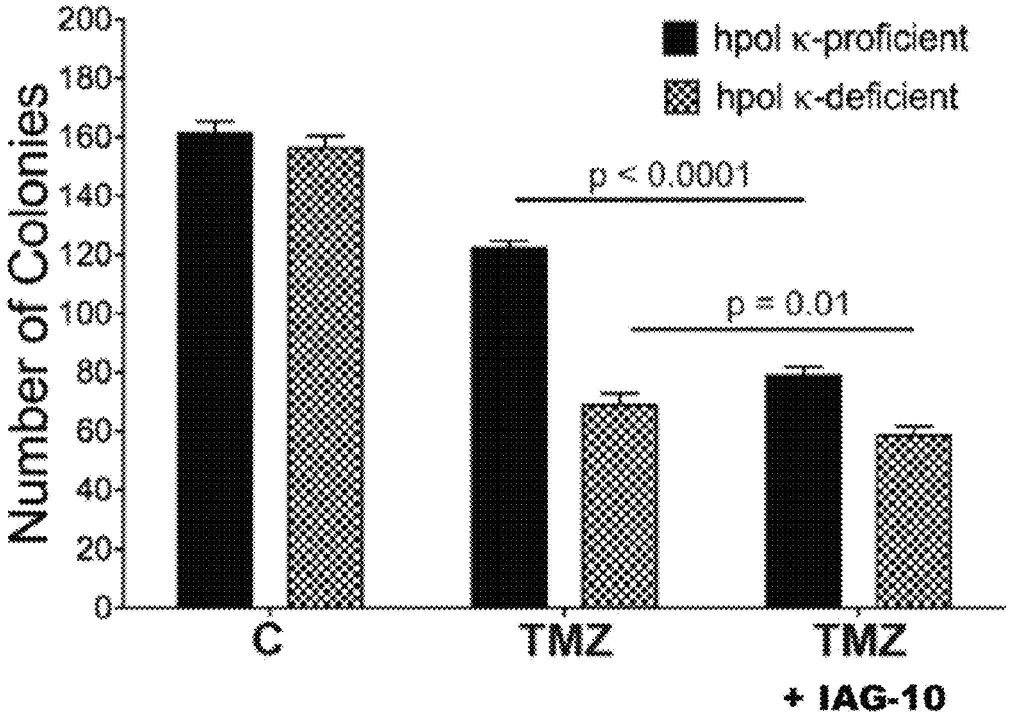

The number of colonies formed by hpol κ-proficient HAP-1 cells exposed to increasing concentrations of TMZ was first measured. As expected, there was a dose-dependent decrease in the number of colonies formed in the presence of TMZ (FIG. 7A). For co-treatment experiments, 0.5 μM IAG-10 was used: a concentration that does not impair colony formation by either cell line. It was found that cotreatment with TMZ and IAG-10 reduced the number of colonies formed by hpol κ-proficient cells at every TMZ concentration tested compared to those treated with TMZ alone (FIG. 7A). At the highest concentration (250 μM) of TMZ, the IAG-10 co-treated cells formed only ~40% as many colonies as untreated cells, while the cells treated with 250 μM TMZ alone were able to form ~75% of control (FIG. 7B). In stark contrast, the hpol κ-deficient cells did not show any significant reduction in colony forming ability when co-treated with TMZ and IAG-10 over TMZ alone (FIG. 7B). The number of colonies formed by the hpol κ-deficient cells exposed to 250 μM TMZ was reduced to less than 50% of the untreated cells (FIGS. 7A and 7B). Thus, compared to the hpol κ-proficient cells, the hpol κ-deficient HAP-1 cells were twice as sensitive to TMZ treatment, consistent with similar observations reported in earlier studies with different cell lines.

The results of our clonogenic survival experiments strongly suggest that the synergistic effect on TMZ toxicity exhibited by IAG-10 is dependent upon the presence of hpol c, although secondary targets for IAG-10 action cannot be ruled out. Yet, the clear difference observed between the hpol κ-proficient and the hpol κ-deficient HAP-1 cells in their response to co-treatment with IAG-10 and TMZ indicates that the secondary, non-hpol κ-mediated effects, if present, are minimal and may not be relevant in the context of TMZ toxicity. Thus, our results with the clonogenic assay demonstrate the possibility of using compounds like IAG-10 as an effective adjuvant treatment for existing anticancer chemotherapeutics like TMZ.

(ix) IAG-10 Increases TMZ-Induced DNA Damage in Hpol κ-Proficient Cells

Figure 7D:
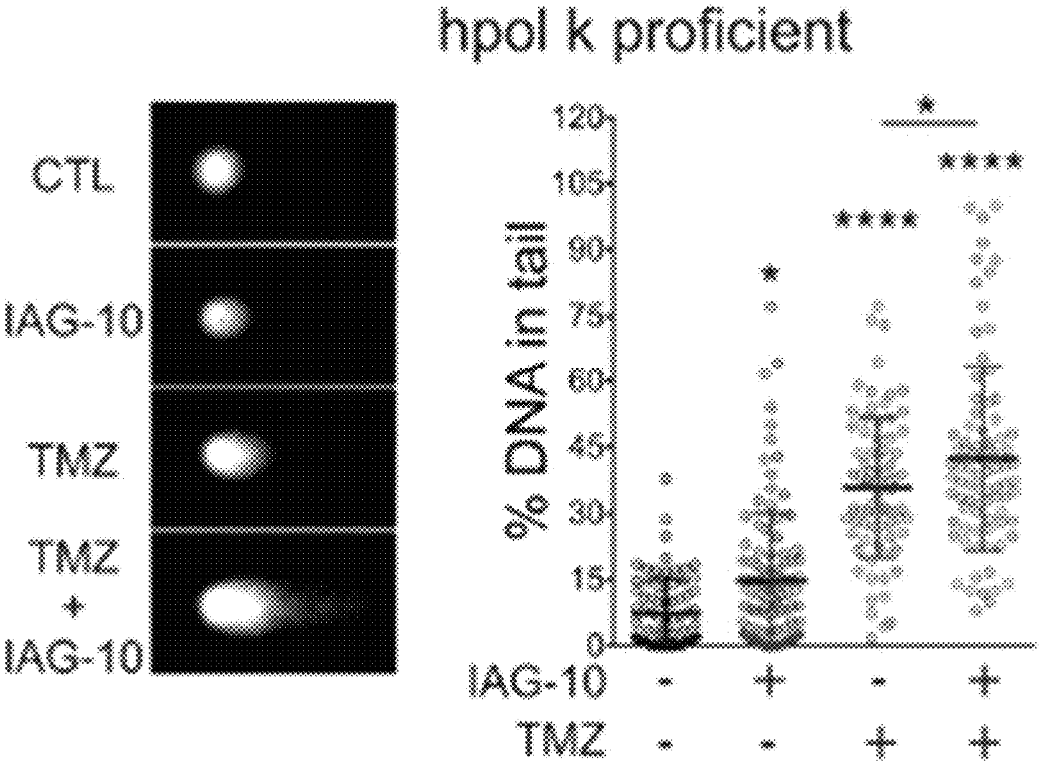
Figure 7E:
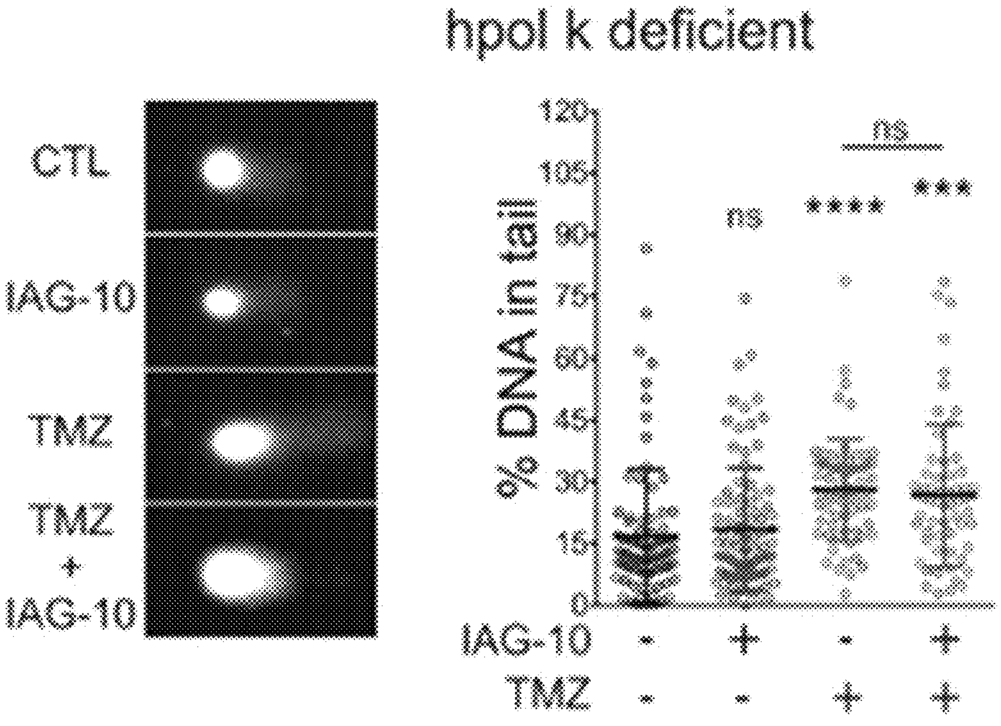

Alkaline comet assays were performed with the hpol κ-proficient and hpol κ-deficient cells to determine whether inhibition of hpol κ by IAG-10 potentiated the genotoxic effects of TMZ in a target-dependent manner. Both the hpol κ-proficient and hpol κ-deficient HAP-1 cells were treated with 100 μM TMZ alone or in combination with 0.5 μM IAG-10, and the resulting DNA damage compared to control (DMSO-treated) was estimated by measuring the percent DNA in the tail in a comet assay (FIGS. 7D and 7E). For every experiment, an estimation of DNA damage was performed in at least 20 cells per biological replicate. Thus, there was a minimum of 60 cells used for calculating DNA damage per experimental condition. Treatment with IAG-10 alone increased the amount of DNA damage in the hpol κ-proficient HAP-1 cells approximately twofold compared to control (FIG. 7D). Treatment with TMZ alone increased DNA damage approximately sevenfold over that of untreated cells (FIG. 7D). The extent of damage increased even further when cells were treated with both TMZ and IAG-10 simultaneously (FIG. 7D). In contrast, treatment of hpol κ-deficient cells with IAG-10 alone did not increase DNA damage over control (FIG. 7E), again indicating that IAG-10-induced effects involve hpol κ. TMZ treatment did produce a significantly greater amount of DNA damage over control in the hpol κ-deficient cells, but unlike in the hpol κ-proficient cells, the extent of damage did not increase further upon co-treatment with TMZ and IAG-10 (FIG. 7E; compare the red and brown scatter plots). The comet assay results lend further support to the notion that IAG-10 targets hpol κ in cells, which impacts DNA damage formation.

(x) Inhibition of Hpol κ by IAG-10 Increases the Mutation Frequency on MMS-Damaged DNA Previous studies have implicated hpol k in the bypass of multiple DNA adducts, including MMS-induced DNA damage. It was hypothesized that inhibition of hpol κ activity by IAG-10 might potentiate the mutagenic potential of MMS-damaged DNA. To test this idea, the supF forward mutagenesis assay was employed.

Figure 9A:
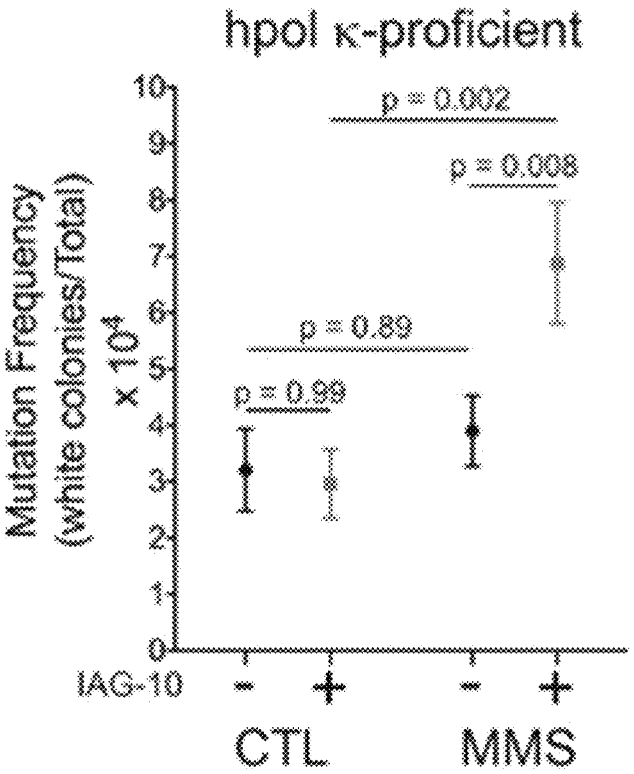
FIG. 9A-9B show IAG-10 alters the mutation frequency of MMS-damaged DNA in hpol κ-proficient cells. The hpol κ-proficient and hpol κ-deficient HAP1 cells were both transfected with supF carrying pSP189 plasmids that were either undamaged (CTL) or MMS-damaged. The HAP-1 cells were grown for 24 h either in the presence of vehicle (DMSO) or 1 μM 1AG-10. The plasmids were extracted and transformed into the *E. coli* MBM7070 competent cells for blue-white screening.
Figure 9B:
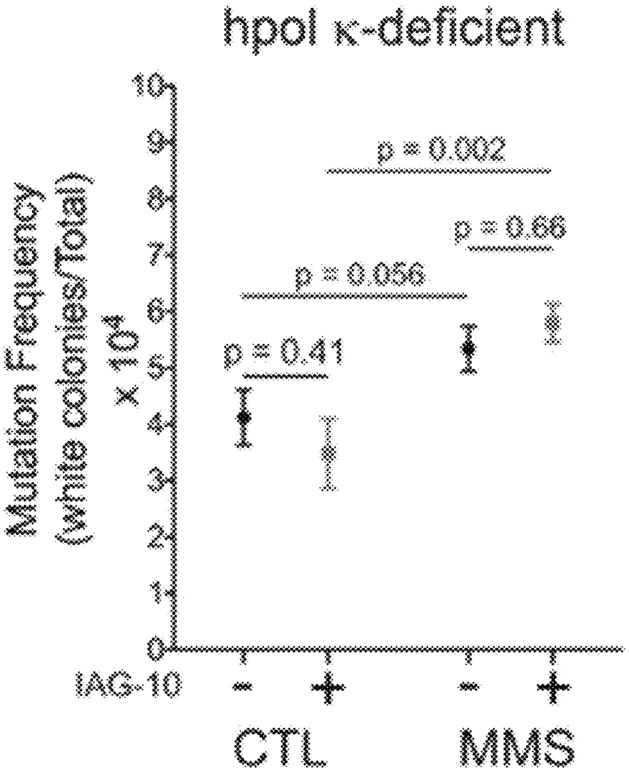

Both the hpol κ-proficient and hpol κ-deficient HAP-1 cells were transfected with either the undamaged pSP189 plasmid harboring the supF gene (control) or the MMS-treated pSP189 plasmid. The transient transfections were performed either alone or coupled with treatment of the cells with 1 μM IAG-10 for 24 h, followed by harvesting the cells and extraction of plasmid DNA. The recovered plasmids were then transformed into the MBM7070 strain of *E. coli* competent cells and screened for blue (wild-type) and white (mutant) colonies to estimate the mutation frequency. In hpol κ-proficient HAP-1 cells, a significant difference in mutation frequency between the control and MMS-treated plasmid DNA was not observed (FIG. 9A). Likewise, the addition of IAG-10 did not change the mutation frequency for the undamaged plasmid. Replication of the MMS-damaged plasmid was more mutagenic in cells treated with IAG-10 than it was in untreated cells (FIG. 9A). Also, treatment with IAG-10 increased the mutation frequency for MMS-damaged DNA approximately twofold over that of the undamaged control plasmid (with or without IAG-10). As expected, the hpol κ-deficient cells replicated the MMS-damaged in a more errorprone manner than the control plasmid (FIG. 9B). However, treatment with IAG-10 did not alter the mutation frequency for either control or MMS-damaged DNA in hpol κ-deficient HAP-1 cells. From these results, it was concluded that treating hpol κ-proficient cells with IAG-10 facilitated an increase in the mutation frequency for MMS-damaged DNA. This increase did not manifest in cells lacking hpol c, once again indicating that the effects of IAG-10 are hpol κ-dependent.

(xi) IAG-10 Strongly Impairs Replicative Capacity of GBM Cells Expressing Hpol κ.

Figure 8A:
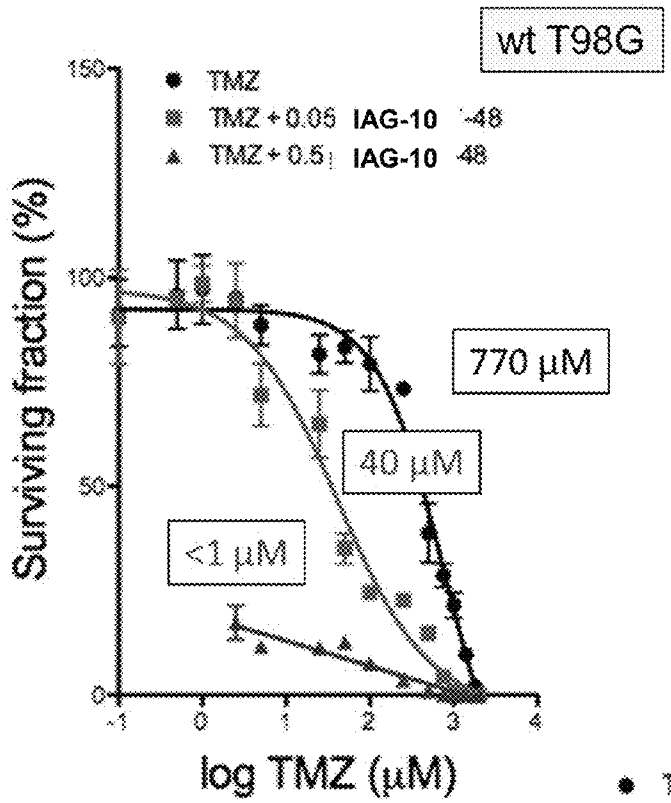
FIG. 8A-8C show IAG-10 sensitizes GBM-derived cells in a synergistic manner when treated in combination with TMZ.
Figure 8B:
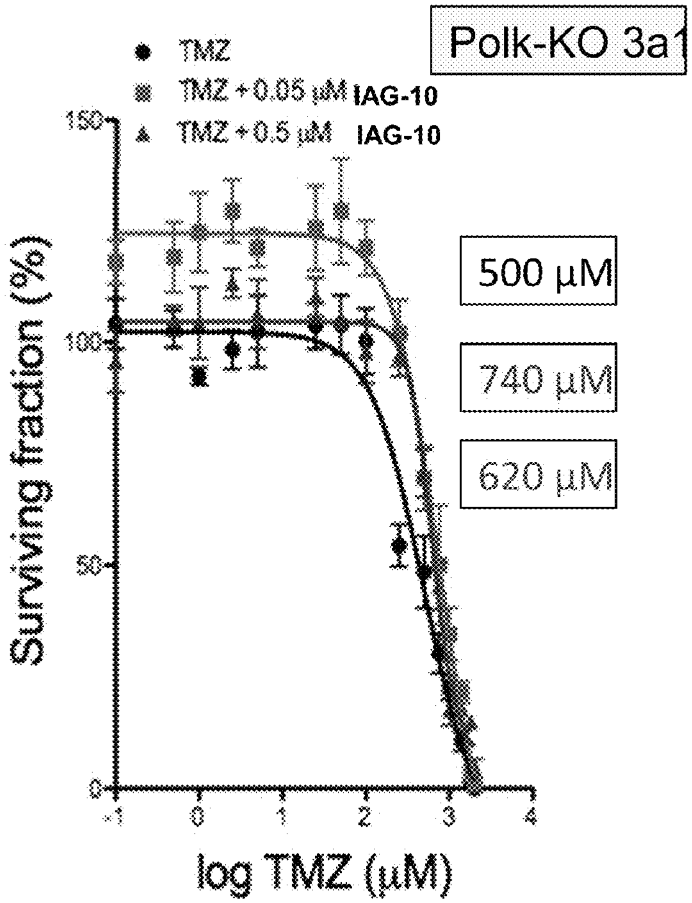
Figure 8C:
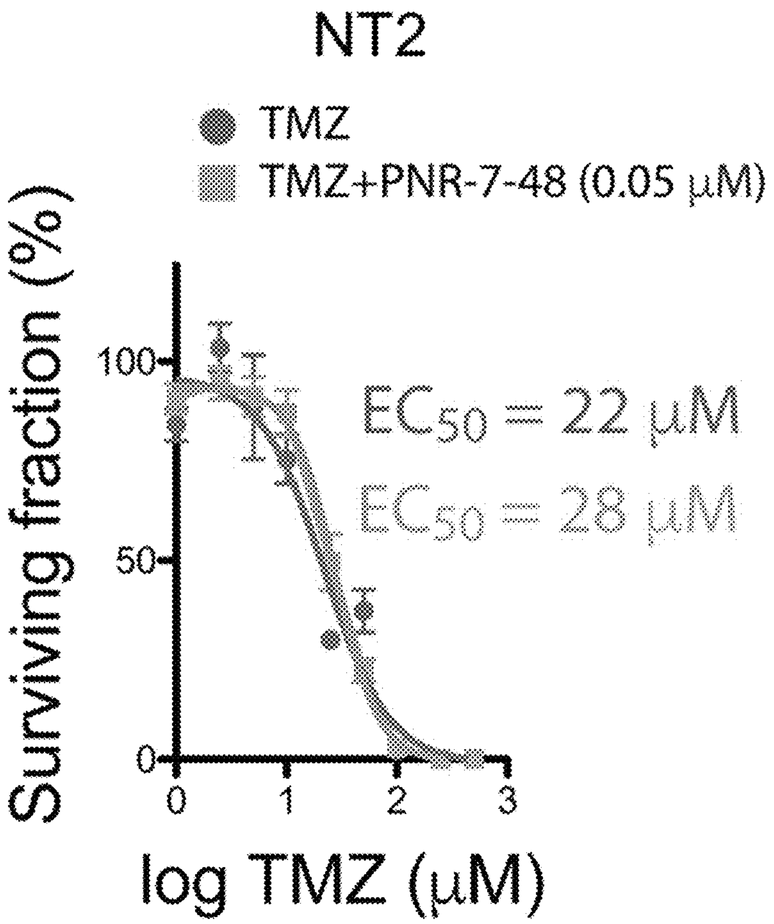

To measure the effects of compounds as disclosed herein on glioblastoma cells, the clonogenic survival assay was performed using exemplary compound IAG-10. The addition of IAG-10 (50 nM) along with TMZ drastically decreased (~10-fold) the cell proliferation of GBM-derived cells compared to the use of TMZ treatment alone (FIG. 8A). In comparison, non-malignant NT2 cells did not exhibit changes in colony formation ability when exposed to IAG-10 and TMZ in combination (FIG. 8B). The combination index values calculated from these experiments indicate strong synergy between TMZ and IAG-10 (0.09). Surprisingly, treatment of IAG-10 alone caused a ~2-fold decrease in GBM-derived cell proliferation compared to NT2 cells (FIG. 8C). Of note, the effects observed for cells treated with IAG-10 alone occurred at concentrations above that used for the combination treatment experiments and provide an indication of tumor specific effects of the IAG compound.

The exemplary molecule (IAG-10) is the most potent and selective hpol κ inhibitor developed to date. The selectivity is attributable to the fact that the compound appears to bind near a motif called the N-clasp that is unique to hpol κ and vital for the activity of the TLS pol. Importantly, the most potent hpol κ inhibitor, IAG-10, potentiates the anti-proliferative effects of TMZ in a target-dependent manner in CML-derived HAP-1 cells. The lead hpol κ inhibitor exhibits even more potent effects in a TMZ-resistant GBM cell line. The anti-proliferative effect of IAG-10 is strongly synergistic with TMZ (Cl value=0.09) and there appears to be little (if any) effect upon non-malignant NT2 cells.

(xii) Loss of Hpol κ Function Inhibits Differentiation, Impedes Spheroid Growth Rate, and Sensitizes GSCs to TMZ.

Cell, spheroid and organoid culture. Grade IV glioma cells (T98G) were obtained from the American Type Culture Collection (ATCC). MCF7 cells were a kind gift from Dr. Timothy Chambers (UAMS). The POLKKO T98G cell lines were generated using CRISPR-Cas9 and validated by immunoblotting (data not shown). For normal culture, these cells were grown in minimum essential media (MEM) containing 10% fetal bovine serum (FBS), 1% (v/v) antibiotic/antimitotic and incubated at 37° C. in 5% $CO_2$.

For spheroid culture, 24 h prior to plating cells, dishes were coated in 1× poly-HEMA (0.6 g poly-2-hydroxyethyl methacrylate into 50 mL 95% EtOH) under sterile conditions and allowed to dry overnight. Coated dishes were hydrated in 1×PBS for 20 min prior to plating. Spheroids were cultured in NeuroCult NS-A basal medium containing NeuroCult NS-A proliferation supplement, 20 ng/mL human recombinant epidermal growth factor (EGF), 10 ng/mL human recombinant basic fibroblast growth factor (bFGF), and 0.0002% heparin (referred to as NS-A complete medium). Spheroids were cultured for at least 12 days prior to treating, passaging or harvesting and supplemented with fresh media every 2-4 days.

Figure 10:
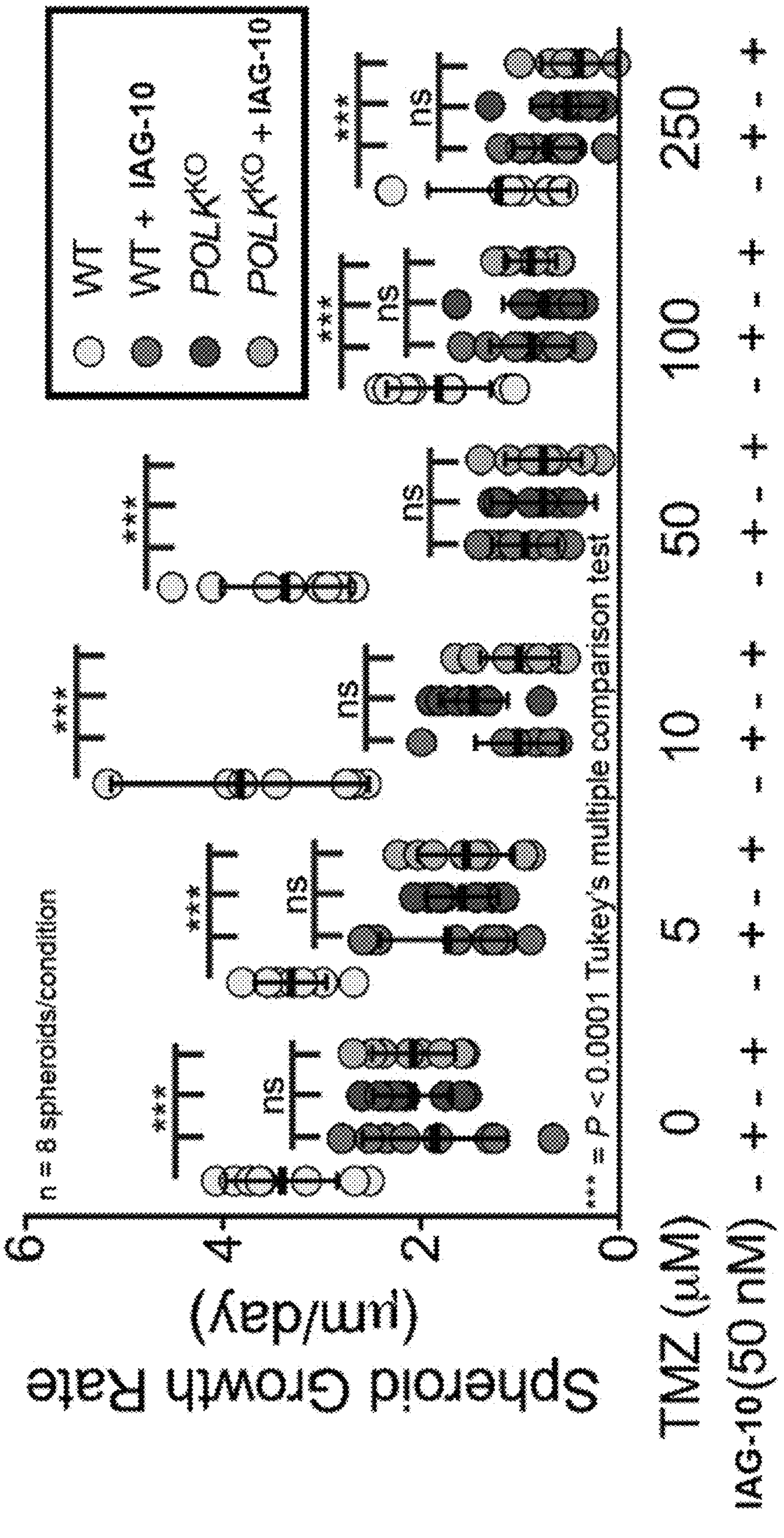
FIG. 10 shows IAG-10 inhibits glioma spheroid growth rate on its own and also enhances the effects of TMZ. IAG-10 mediated hpol κ-loss of function impedes glioblastoma stem cell spheroid growth rate and sensitizes GSCs to TMZ.

Spheroid growth rate assay. Around 500 cells (T98G hpol κ+ or hpol κ-) per well were plated in a 1× poly-HEMA coated 96 well plate in complete NS-A media. Cells were treated with 50 nM or 500 nM 7-48, or 10 or 20 μM 680C91 with or without a range of TMZ concentrations (0, 5, 10, 50, 100, 250 μM). Cells were supplemented with media containing the correct concentration of 680C91, 7-48 and TMZ every 2-4 days. Cells were grown for 12 days and whole well images were taken at various time points throughout the growth period. Spheroids with a diameter of 50 □m or larger were counted as true spheroids and an average size was determined for each well. Changes in average size for each well over the growth time was recorded and used to generate the growth rate. Genetic ablation or pharmacological inhibition of hpol κ impaired spheroid growth rate and augmented the effects of TMZ (FIG. 10).

Figure 11:
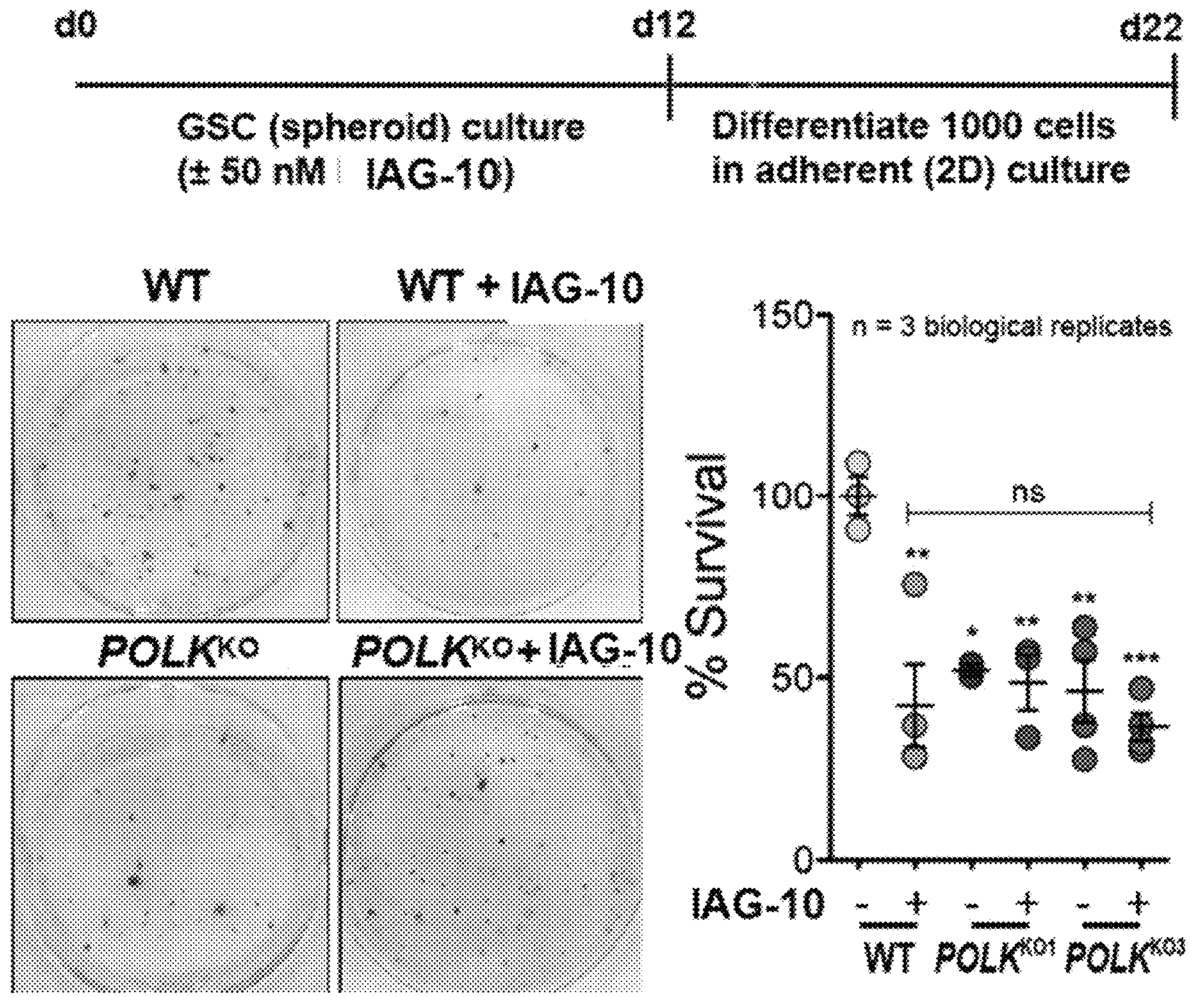
FIG. 11 shows genetic ablation and pharmacological inhibition of pol kappa with IAG-10 both inhibit GSC differentiation.
Figure 12A:
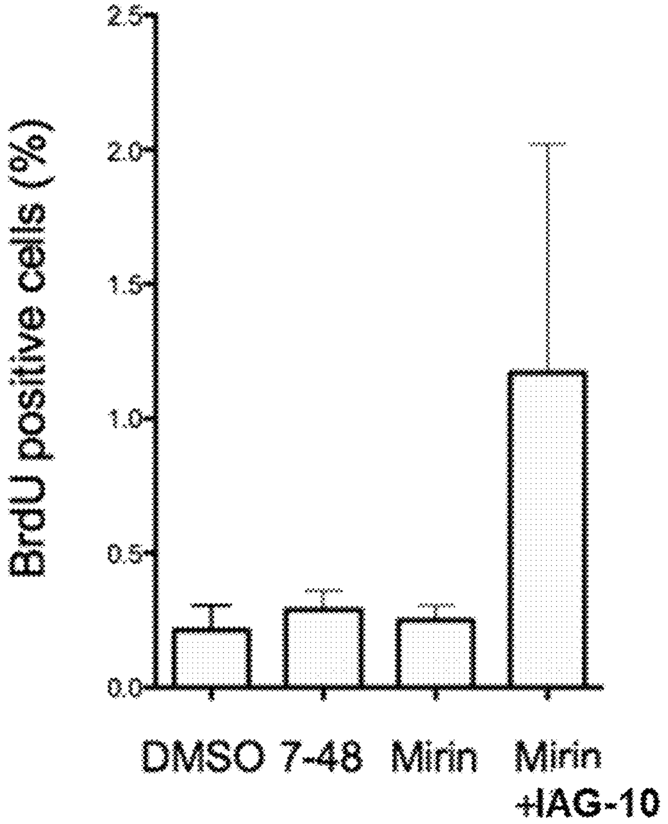
FIG. 12A-12B show combined inhibition of pol kappa and homologous recombination (with Mre11 inhibitor mirin) increases ssDNA gap formation.
Figure 12B:
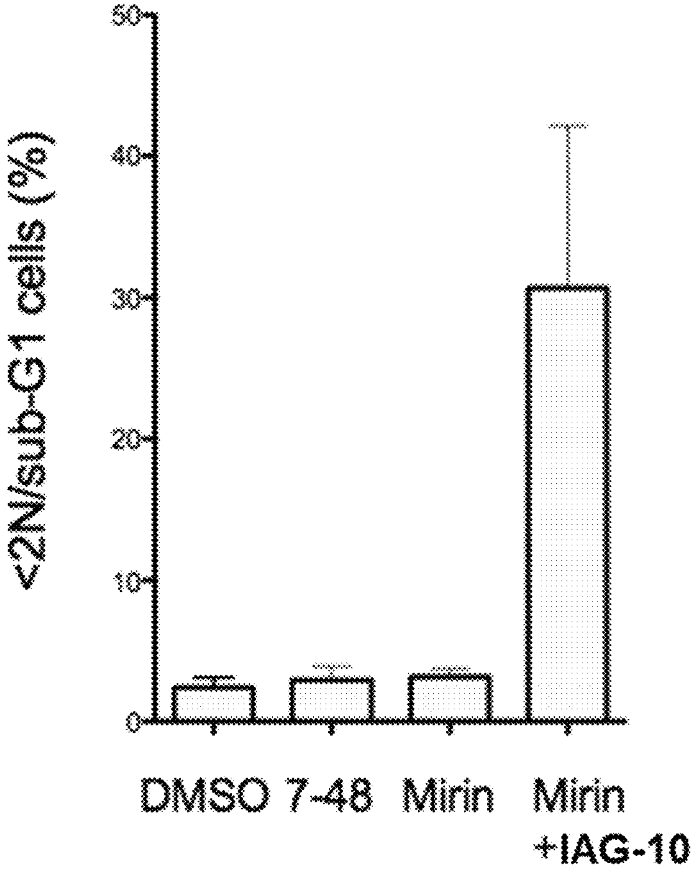

GSC clonogenic survival assay. Spheroids proficient and deficient in hpol κ were cultured for 12 days as described above before treating with PNR 7-48 (50 nM) for 3 hours. Spheroids were harvested, titrated into single cell populations and counted via trypan blue exclusion assay. Around 500 viable cells were plated per well in a 6 well dish and allowed to recover for 8-10 days in MEM with 10% FBS. Cells were fixed with 4% formaldehyde (v/v) for 30 min followed by staining with crystal violet (Sigma Aldrich, St. Louis, MO) for 30 min. Total number of colonies were counted using the EVOS microscope, with viable colonies consisting of 25 cells or more. This experiment was done in technical triplicate. As with spheroid growth, clonogenic survival was impeded for T98G cells lacking hpol κ activity (FIG. 11).

IAG-10 inhibits glioma spheroid growth rate on its own and also enhances the effects of TMZ.

Genetic ablation and pharmacological inhibition of pol kappa with IAG-10 both inhibit GSC differentiation.

(xiii) IAG-10 and Mre 11 Increase Death of Breast Cancer Cells

MCF7 cells were plated in 60 mm dishes at a confluency of 300,000 cells per dish and incubated overnight. Cells were treated the next day with BrdU (10 μM). The compounds were diluted in DMSO and added to the media at a final concentration of PNR-7-48 (0.5 μM) and Mirin (100 μM). The final concentration of DMSO was 0.1% (v/v). After 48 hours of treatment, media was removed and cells were washed in 1×PBS and trypsinized. Cells were then resuspended in media and centrifuged at 1500 rpm (calculate relative centrifugal force, RCF) for 5 minutes. The supernatant was removed, and again cells were washed and centrifuged. The supernatant was discarded and cells were resuspended in ice-cold 70% (v/v) ethanol prepared in 1×PBS while being vortexed. After overnight fixing at 4° C., cells were vortexed and centrifuged at 3000 rpm (RCF) for 10 minutes. Ethanol was removed leaving residual amounts for cell resuspension by vortexing. Fixed cells were stained with fluorescent anti-BrdU antibodies (FITC mouse anti-BrdU kit; 556028; BD) without prior acid treatment to detect only ssDNA. To confirm that the experimental cells had incorporated BrdU, aliquots of all nuclei were also denatured using HCL and then neutralized with sodium borate before staining with the anti-BrdU antibody. Afthis this, cells were washed with 1×PBS and propidium Iodide staining solution was then added to the cells while vortexing. The samples were stained 2 hours at room temperature in the dark, then transferred to 5 ml collection tubes. Samples were analyzed using the BD FACSCalibur Flow Cytometer in the UAMS Flow Cytometry Core. Combined inhibition of pol kappa and homologous recombination (with Mre11 inhibitor mirin) increases ssDNA gap formation (BrdU+cells) and cell death (sub-G1 cells) in the MCF7 cell line.

Conclusions

The development of strategies to improve therapies for aggressive cancers remains an important area of research. Cellular responses to genotoxins are a potential target for these advancements in clinical care. DNA repair and damage response mechanisms have received considerable attention in this regard, and more recent work has identified damage tolerance mechanisms as playing important roles in resistance to anticancer drugs. Many groups have pursued studies targeting DNA repair and TLS as a means of potentiating the effects of genotoxic agents, specifically targeting the DNA pols that promote direct bypass of DNA damage. The present study provides several indole-derived compounds as potential TLS pol inhibitors. Until now, focus had been on the identification of hpol η inhibitors, as the in vivo and clinical evidence supporting a role for this enzyme in chemoresistance is fairly robust. While the rationale for targeting hpol κ is also sound, the identification of potent inhibitors has proven challenging. The initial findings were built upon and have now elucidated key differences between the mechanism of inhibition by indole-derived compounds for hpols η and κ.

An initial screen identified candesartan cilexetil and MK-886 as inhibitors of hpol κ. Both compounds possess bicyclic ring systems. Candesartan cilexetil contains a benzimidazole ring system and is an angiotensin II receptor antagonist, while MK886, an inhibitor of 5-lipooxygenase activating protein inhibitor, contains a central indole moiety. Both candesartan and MK-886 were found to inhibit recombinant hpol κ with $IC_{50}$ values in the tens of micromolar, but neither was specific to the target, as the compounds inhibited other TLS pols with comparable or greater potency. In the case of MK-886, there was some effect on the affinity of hpol κ but mostly at concentrations of inhibitor well above the $IC_{50}$ value. By way of comparison, the IAG and IBA compounds reported here (IAG-10 and IBA-32) increased the $K_{D,DNA}$ Approximately threefold when incubated at concentrations near the $IC_{50}$ for inhibition of pol activity (FIG. 3). The realization that IAG-10 likely destabilizes binary complex formation led us to perform experiments in which the concentration of enzyme and DNA in the reaction mixture was varied. In this way, the apparent potency of IAG-10 against hpol κ was improved and the apparent selectivity of the compound for hpol κ was increased, as the $IC_{50}$ for inhibition of hpol η increased slightly at lower concentrations of enzyme and DNA (FIG. 4). Thus, altering the reaction conditions changed the specificity of IAG-10 for hpol κ over η from ~2-fold to ~30-fold.

Figure 13A:
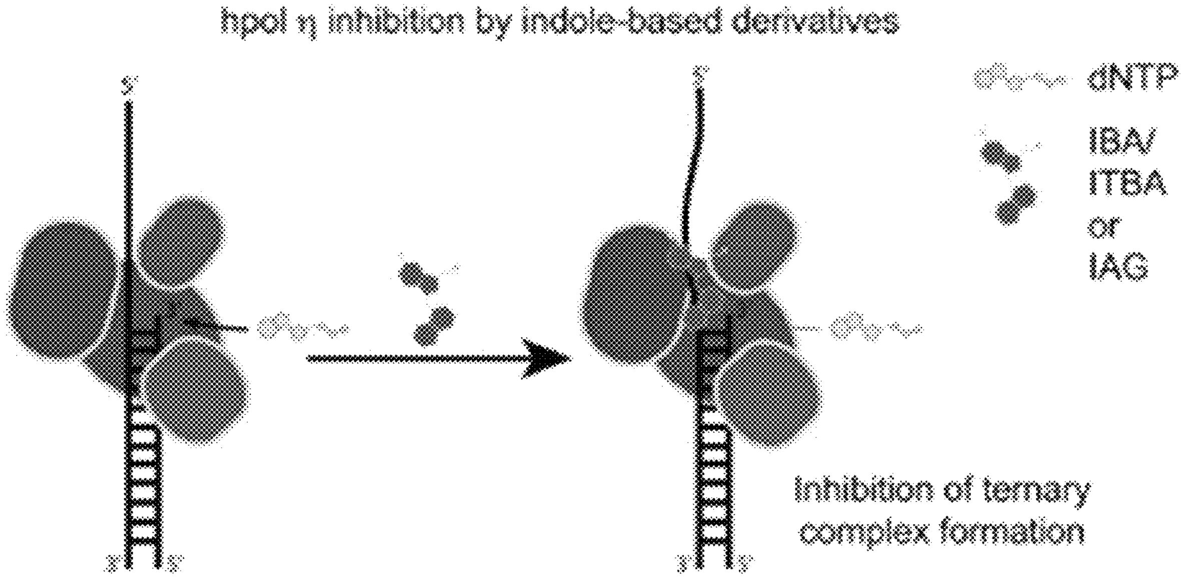
FIG. 13A-13B are models for inhibition of hpol η, and κ by indole-derived compounds.
Figure 13B:
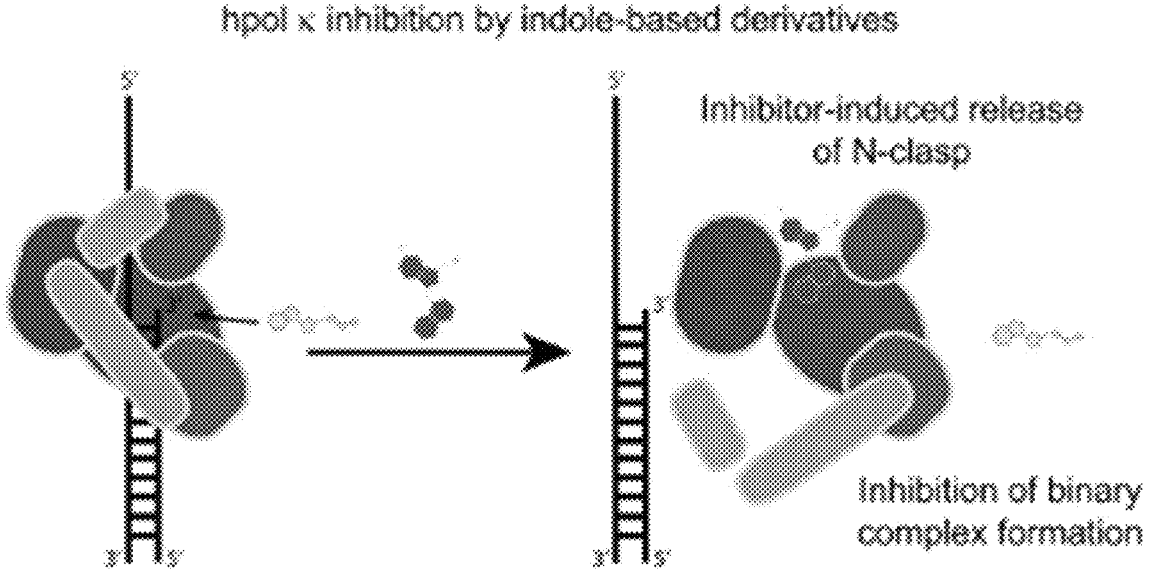
Figure 14:
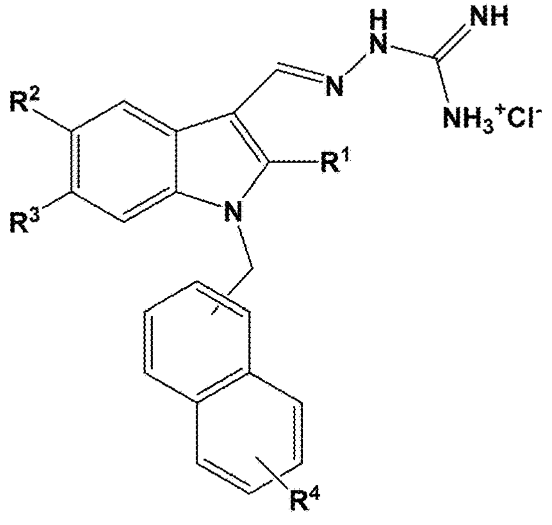
FIG. 14 shows IAG general structure I.
Figure 14:
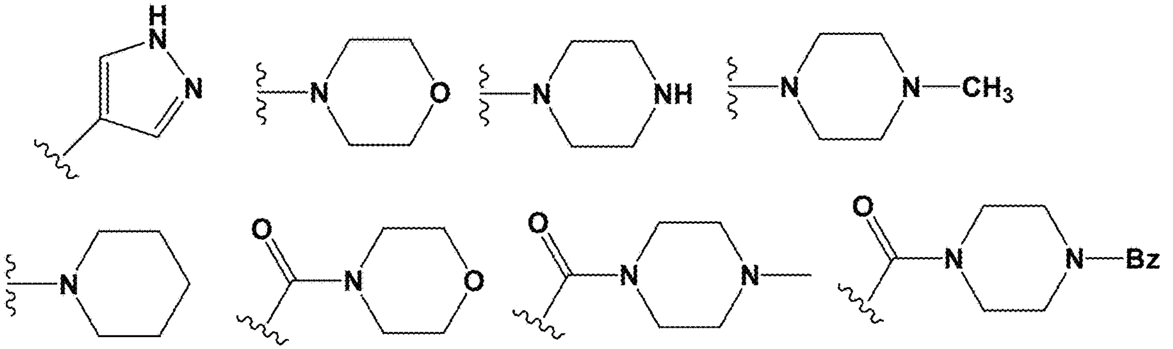
Figure 14:
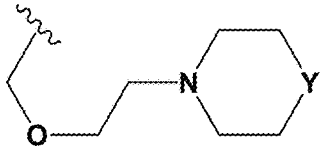
Figure 15:
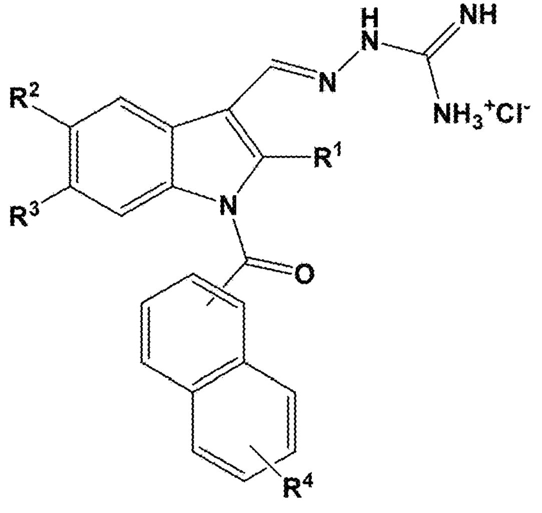
FIG. 15 shows IAG general structure II.
Figure 15:
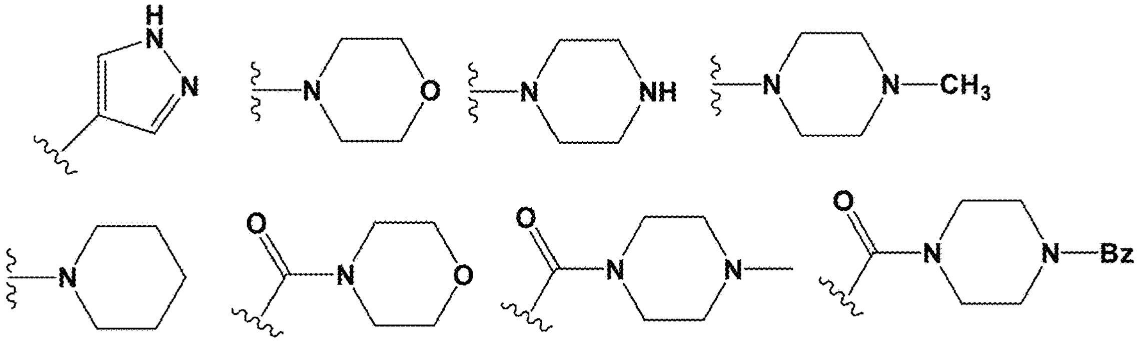
Figure 15:
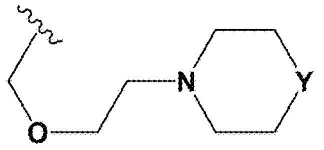
Figure 16:
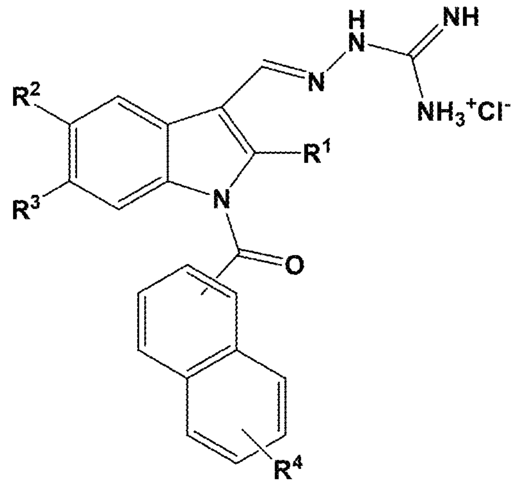
FIG. 16 shows IAG general structure III.
Figure 16:
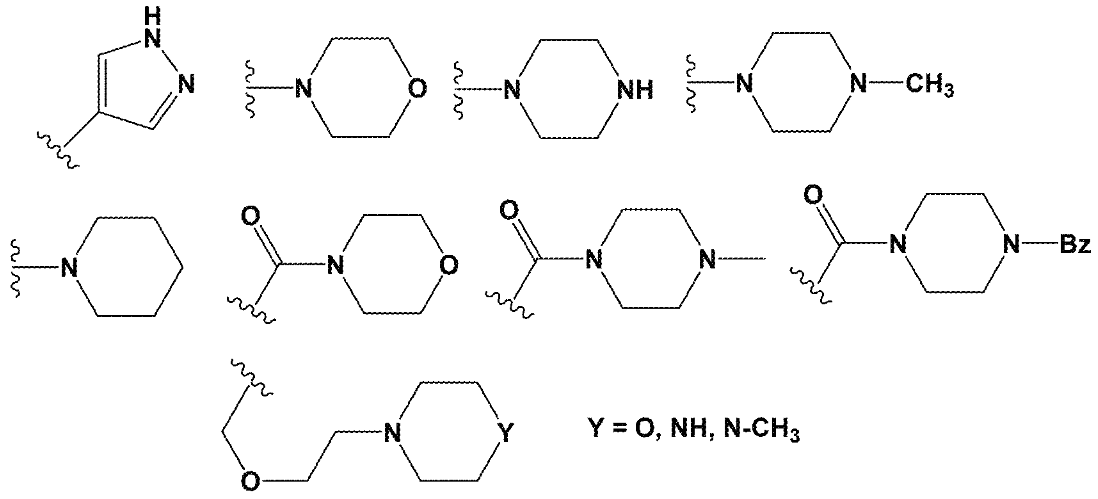

The results with IAG-10 led us to propose two distinct models for inhibition of hpol η and κ (FIG. 13). First, it was observed that either a partial competitive or purely competitive mechanism of hpol η inhibition for a variety of indole-derived compounds. Based on HPG-footprinting and molecular docking studies, it was proposed that these inhibitors bind somewhere between the finger and little finger domains of hpol q and that this disrupts the template strand near the nascent base pair (FIG. 13A). Binding to a similar site on hpol κ produces a stronger effect on binary complex formation because the normal position of the N-clasp is disrupted (FIG. 13B). Without the N-clasp to stabilize the position of the little finger, hpol κ cannot effectively bind DNA, which is consistent with the structure and activity of hpol κ constructs lacking the N-clasp.

Structural studies have noted differences in the architecture of the pol κ and η active sites that undoubtedly emerged as selective pressure to bypass distinct DNA lesions shaped the evolution of these enzymes. For example, pol η is an important means of tolerating fused pyrimidine lesions that occur following exposure to UV irradiation. As such, the crystal structures of pol η reveal an active site that can readily accommodate two template bases. This structural feature also appears to be important for the ability of pol η to act as a "double-agent" when it bypasses damage induced by platinumbased chemotherapeutics.

In contrast to pol η, pol κ relies upon residues in the N-clasp, finger, and little finger domains to guide and hold template residues in the pol active site. Residues such as Phe-49 in the N-clasp, Ser134 and Phe155 in the finger domain, and Lys461 and Arg507 in the little finger domain help to guide the template into an active site that is smaller than that observed for pol η or the archaeal homologue Dpo4 from *Sulfolobus solfataricus*. Amino acid side chains, including Met135 and Ala151, present a loop in the finger domain that limits the orientation of the nascent base pair in the hpol κ active site. Moreover, the unique orientation of the little finger domain of hpol κ exposes the minor groove side of the DNA substrate to solvent, which facilitates the accommodation of bulky, minor groove adducts like those formed from bioactivated benzo[a]-pyrene. Compared to Dpo4, the little finger domain of hpol κ is rotated ~19° away from the pol core. This precarious positioning of the little finger places an increased reliance upon the N-clasp to stabilize hpol κ binary and ultimately ternary complex formation. In the case of IAG-10, these structural features likely represent the Achilles' heel of hpol κ that allows effective inhibition of the enzyme.

The mechanism by which IAG-10 inhibits hpol κ presents some interesting possibilities for what might occur in cells or in vivo. Misregulated expression or recruitment of hpol κ to replication forks in the absence of DNA damaging agents increases markers of replication stress and genomic instability. In tumors that overexpress hpol κ, such as glioblastomas, inhibiting the aberrant recruitment of hpol κ could alleviate some of the stress imparted by misregulated TLS. Of course, there is a strong possibility that hpol κ inhibition could alleviate problems associated with chemoresistance, and proof-of-principle experiments in a mouse model have illustrated that resistance to TMZ is facilitated in part by expression of hpol κ. The key role for hpol κ activity in promoting recruitment of the 9-1-1 complex, activation of the ATR-Chk I checkpoint, and subsequent resolution of fork stress through TLS or repair pathways such as homology directed repair make it an attractive target for drug design. The mechanism of inhibition exhibited by IAG-10, which depends on a domain that is unique to hpol κ, makes it an interesting molecule for further study. Efforts to combine TLS pol inhibitors with traditional DNA damaging therapeutics are ongoing and represent an important strategy for targeting mechanisms of resistance and perhaps even attenuating these processes in cancer. These findings pave the way for development of combination treatments that target hpol κ in cancer where it likely facilitates multiple aspects of tumor etiology through its ability to bypass DNA damage and its role in the resolution of replication stress.

REFERENCES

1. Bhatt A. N., Mathur R., Farooque A., Verma A., and Dwarakanath B. S. 2010. "Cancer biomarkers—current perspectives." *Indian J Med Res,* 132:129-49.
2. Cho W. C. 2007. "Contribution of oncoproteomics to cancer biomarker discovery." *Mol Cancer,* 6:25.
3. Chou T. C. 2010. "Drug combination studies and their synergy quantification using the Chou-Talalay method." *Cancer Res,* 70 (2):440-6.
4. Louis D. N., Ohgaki H., Wiestler O. D., Cavenee W. K., Burger P. C., Jouvet A., Scheithauer B. W., and Kleihues P. 2007. "The 2007 WHO classification of tumours of the central nervous system." *Acta Neuropathol,* 114 (2):97-109.
5. Peng C., Chen Z., Wang S., Wang H. W., Qiu W., Zhao L., Xu R., Luo H., Chen Y., Chen D., You Y., Liu N., and Wang H. 2016. "The Error-Prone DNA Polymerase kappa Promotes Temozolomide Resistance in Glioblastoma through Rad17-Dependent Activation of ATR-Chk1 Signaling." *Cancer Res,* 76 (8):2340-53.
6. Prasad R. N., and McKay A. F. 1967. "Acylation of guanidines and guanylhydrazones." *Canadian Journal of Chemistry,* 45 (19):2247-2252.
7. Wang H., Wu W., Wang H. W., Wang S., Chen Y., Zhang X., Yang J., Zhao S., Ding H. F., and Lu D. 2010. "Analysis of specialized DNA polymerases expression in human gliomas: association with prognostic significance." *Neuro Oncol,* 12 (7):679-86.
8. Wen P. Y., and Kesari S. 2008. "Malignant gliomas in adults." *N Engl J Med,* 359 (5):492-507.
9. Zafar M. K., Maddukuri L., Ketkar A., Penthala N. R., Reed M. R., Eddy S., Crooks P. A., and Eoff R. L. 2018. "A Small-Molecule Inhibitor of Human DNA Polymerase rn Potentiates the Effects of Cisplatin in Tumor Cells." *Biochemistry,* 57 (7):1262-1273.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The term "about" or "approximately" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A compound of Formula (I) or a salt thereof:

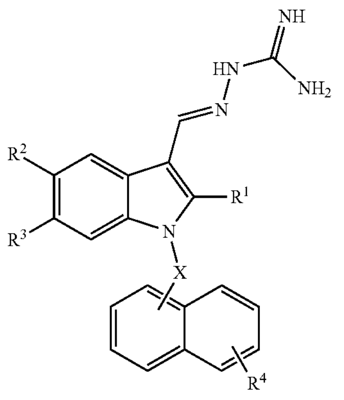

wherein $R^1$ is hydrogen;

wherein $R^2$ is independently selected from the group consisting of hydrogen, deuterium, halogen, $CH_3$, $OCH_3$, OH, CN, $NH_2$, $CH_2OH$, $CH_2NH_2$, $OCH_2CH_2N(CH_2H_5)_2$, $OCH_2CH_2N(CH_3)_2$, $NHSO_2CH_3$, $CF_3$, $OCHF_2$, $OCH_2CH_2NH_2$, $COOC_2H_5$, COOH, $COOCH_3$,

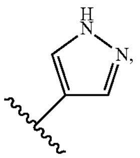, 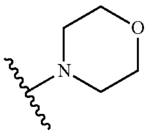, 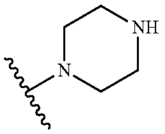, 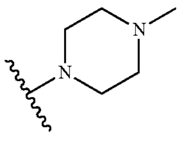, 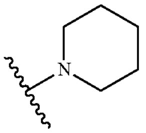, 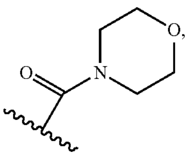,

-continued

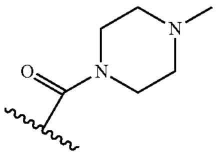, 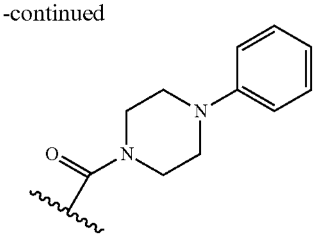,

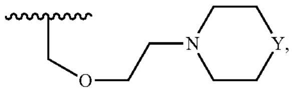,

OR', SR', NR'R', NR'COR', NR'CONR'R', NR'$CO_2$R', COR', $CO_2$R', NOR', $NO_2$, CONR'R', OC(O) NR'R', $SO_2$R', $SO_2$NR'R', NR'$SO_2$R', NR'$SO_2$NR'R', C(O)C(O)R', C(O)$CH_2$C(O)R', a substituted or unsubstituted $C_1$-$C_6$ alkyl, a substituted or unsubstituted $C_2$-$C_6$ alkenyl, a substituted or unsubstituted $C_2$-$C_6$ alkynyl, a substituted or unsubstituted aryl, and a substituted or unsubstituted heteroaryl; R' is independently selected from the group consisting of hydrogen, or alternately, two R' moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur; Y is independently selected from O, NH, or N—$CH_3$;

wherein $R^3$ and $R^4$ are hydrogen; and wherein X is independently selected from $CH_2$, CO and $SO_2$.

2. The compound of claim 1, wherein X is CO.

3. The compound of claim 1, wherein X is $CH_2$.

4. The compound of claim 1, wherein $R^2$ is a halogen.

5. The compound of claim 4, wherein the halogen is Cl.

6. The compound of claim 1, wherein the compound is selected from

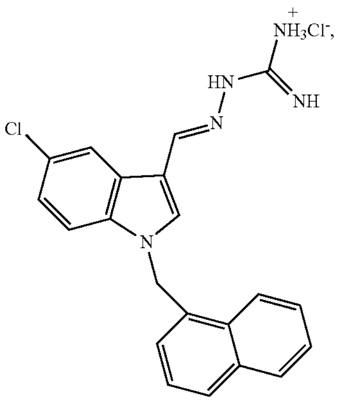

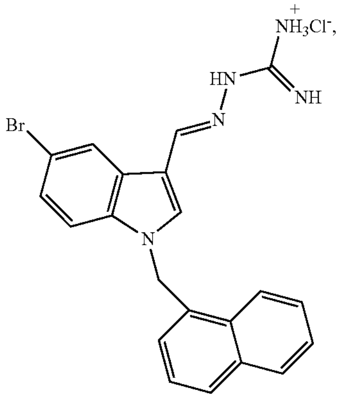

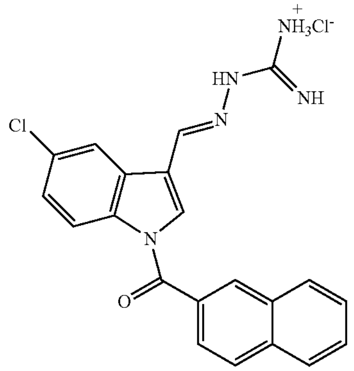

, and

-continued

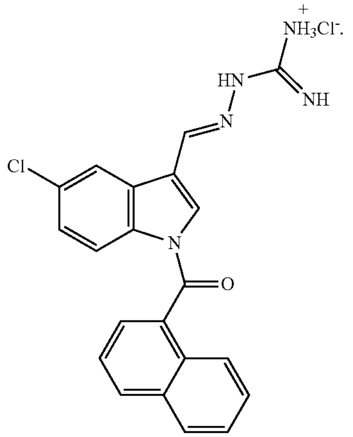

7. A pharmaceutical composition comprising a compound of claim 1.

8. The pharmaceutical composition of claim 7, wherein the composition is formulated as a nanoparticle carrier for the compound.

9. A method of treating glioblastoma, breast cancer, leukemia, or a combination thereof in a subject in need thereof, the method comprising administering to the subject a therapeutically effective amount of a pharmaceutical composition comprising a compound of claim 1.

10. The method of claim 9, wherein the method further comprises administering a genotoxic agent; and wherein the genotoxic agent is an alkylating agent selected from the group consisting chlorambucil, cyclophosphamide, ifosfamide, melphalan, streptozocin, carmustine, lomustine, busulfan, dacarbazine, temozolomide, thiotepa, and altretamine.

11. The method of claim 10, wherein the alkylating agent is temozolomide.

12. The method of claim 9, wherein the glioblastoma, breast cancer, or leukemia is resistant to a genotoxic therapy.

13. The method of claim 9, wherein the glioblastoma, breast cancer, or leukemia has increased expression of DNA-polymerase kappa.

14. The method of claim 13, wherein DNA-polymerase kappa binding to DNA is inhibited in the glioblastoma, breast cancer, or leukemia.

* * * * *

SEQUENCE LISTING

```
<160> NUMBER OF SEQ ID NOS: 60

<210> SEQ ID NO 1
<211> LENGTH: 13
<212> TYPE: PRT
<213> ORGANISM: Homo sapiens

<400> SEQUENCE: 1

Lys Gly Ser Arg Phe Tyr Gly Asn Glu Leu Lys Lys Glu
1               5                   10


<210> SEQ ID NO 2
<211> LENGTH: 16
<212> TYPE: PRT
<213> ORGANISM: Homo sapiens

<400> SEQUENCE: 2

Lys Thr Glu Ile Asp Ala Asp Phe Pro His Pro Leu Arg Leu Arg Leu
1               5                   10                  15


<210> SEQ ID NO 3
<211> LENGTH: 12
```

```
<212> TYPE: PRT
<213> ORGANISM: Homo sapiens

<400> SEQUENCE: 3

Lys Ala Gly Met Glu Gly Leu Asp Lys Glu Lys Ile
1               5                   10


<210> SEQ ID NO 4
<211> LENGTH: 15
<212> TYPE: PRT
<213> ORGANISM: Homo sapiens

<400> SEQUENCE: 4

Lys Ala Gly Met Glu Gly Leu Asp Lys Glu Lys Ile Asn Lys Ile
1               5                   10                  15


<210> SEQ ID NO 5
<211> LENGTH: 15
<212> TYPE: PRT
<213> ORGANISM: Homo sapiens

<400> SEQUENCE: 5

Lys Ile Asn Lys Ile Ile Met Glu Ala Thr Lys Gly Ser Arg Phe
1               5                   10                  15


<210> SEQ ID NO 6
<211> LENGTH: 13
<212> TYPE: PRT
<213> ORGANISM: Homo sapiens

<400> SEQUENCE: 6

Lys Gly Ser Arg Phe Tyr Gly Asn Glu Leu Lys Lys Glu
1               5                   10


<210> SEQ ID NO 7
<211> LENGTH: 12
<212> TYPE: PRT
<213> ORGANISM: Homo sapiens

<400> SEQUENCE: 7

Arg Phe Tyr Gly Asn Glu Leu Lys Lys Glu Lys Gln
1               5                   10


<210> SEQ ID NO 8
<211> LENGTH: 17
<212> TYPE: PRT
<213> ORGANISM: Homo sapiens

<400> SEQUENCE: 8

Lys Glu Lys Gln Val Asn Gln Arg Ile Glu Asn Met Met Gln Gln Lys
1               5                   10                  15

Ala


<210> SEQ ID NO 9
<211> LENGTH: 15
<212> TYPE: PRT
<213> ORGANISM: Homo sapiens

<400> SEQUENCE: 9

Lys Gln Val Asn Gln Arg Ile Glu Asn Met Met Gln Gln Lys Ala
1               5                   10                  15


<210> SEQ ID NO 10
<211> LENGTH: 19
```

<212> TYPE: PRT
<213> ORGANISM: Homo sapiens

<400> SEQUENCE: 10

Arg Ile Glu Asn Met Met Gln Gln Lys Ala Gln Ile Thr Ser Gln Gln
1 5 10 15

Leu Arg Lys

<210> SEQ ID NO 11
<211> LENGTH: 12
<212> TYPE: PRT
<213> ORGANISM: Homo sapiens

<400> SEQUENCE: 11

Lys Ala Gln Ile Thr Ser Gln Gln Leu Arg Lys Ala
1 5 10

<210> SEQ ID NO 12
<211> LENGTH: 19
<212> TYPE: PRT
<213> ORGANISM: Homo sapiens

<400> SEQUENCE: 12

Arg Lys Ala Gln Leu Gln Val Asp Arg Phe Ala Met Glu Leu Glu Gln
1 5 10 15

Ser Arg Asn

<210> SEQ ID NO 13
<211> LENGTH: 23
<212> TYPE: PRT
<213> ORGANISM: Homo sapiens

<400> SEQUENCE: 13

Arg Asn Leu Ser Asn Thr Ile Val His Ile Asp Met Asp Ala Phe Tyr
1 5 10 15

Ala Ala Val Glu Met Arg Asp
20

<210> SEQ ID NO 14
<211> LENGTH: 29
<212> TYPE: PRT
<213> ORGANISM: Homo sapiens

<400> SEQUENCE: 14

Arg Asn Leu Ser Asn Thr Ile Val His Ile Asp Met Asp Ala Phe Tyr
1 5 10 15

Ala Ala Val Glu Met Arg Asp Asn Pro Glu Leu Lys Asp
20 25

<210> SEQ ID NO 15
<211> LENGTH: 28
<212> TYPE: PRT
<213> ORGANISM: Homo sapiens

<400> SEQUENCE: 15

Arg Asp Asn Pro Glu Leu Lys Asp Lys Pro Ile Ala Val Gly Ser Met
1 5 10 15

Ser Met Leu Ser Thr Ser Asn Tyr His Ala Arg Arg
20 25

<210> SEQ ID NO 16
<211> LENGTH: 23

<212> TYPE: PRT
<213> ORGANISM: Homo sapiens

<400> SEQUENCE: 16

```
Lys Asp Lys Pro Ile Ala Val Gly Ser Met Ser Met Leu Ser Thr Ser
1               5                   10                  15

Asn Tyr His Ala Arg Arg Phe
            20
```

<210> SEQ ID NO 17
<211> LENGTH: 16
<212> TYPE: PRT
<213> ORGANISM: Homo sapiens

<400> SEQUENCE: 17

```
Arg Arg Phe Gly Val Arg Ala Ala Met Pro Gly Phe Ile Ala Lys Arg
1               5                   10                  15
```

<210> SEQ ID NO 18
<211> LENGTH: 16
<212> TYPE: PRT
<213> ORGANISM: Homo sapiens

<400> SEQUENCE: 18

```
Lys Arg Leu Pro Gln Leu Ile Ile Val Pro Pro Asn Phe Asp Lys Tyr
1               5                   10                  15
```

<210> SEQ ID NO 19
<211> LENGTH: 18
<212> TYPE: PRT
<213> ORGANISM: Homo sapiens

<400> SEQUENCE: 19

```
Lys Arg Leu Pro Gln Leu Ile Ile Val Pro Pro Asn Phe Asp Lys Tyr
1               5                   10                  15

Arg Ala
```

<210> SEQ ID NO 20
<211> LENGTH: 29
<212> TYPE: PRT
<213> ORGANISM: Homo sapiens

<400> SEQUENCE: 20

```
Lys Glu Val Lys Glu Ile Leu Ala Asp Tyr Asp Pro Asn Phe Met Ala
1               5                   10                  15

Met Ser Leu Asp Glu Ala Tyr Leu Asn Ile Thr Lys His
            20                  25
```

<210> SEQ ID NO 21
<211> LENGTH: 26
<212> TYPE: PRT
<213> ORGANISM: Homo sapiens

<400> SEQUENCE: 21

```
Lys Glu Ile Leu Ala Asp Tyr Asp Pro Asn Phe Met Ala Met Ser Leu
1               5                   10                  15

Asp Glu Ala Tyr Leu Asn Ile Thr Lys His
            20                  25
```

<210> SEQ ID NO 22
<211> LENGTH: 11
<212> TYPE: PRT
<213> ORGANISM: Homo sapiens

<400> SEQUENCE: 22

```
Arg Gln Asn Trp Pro Glu Asp Lys Arg Arg Tyr
1               5                   10
```

<210> SEQ ID NO 23
<211> LENGTH: 18
<212> TYPE: PRT
<213> ORGANISM: Homo sapiens

<400> SEQUENCE: 23

```
Arg Tyr Phe Ile Lys Met Gly Ser Ser Val Glu Asn Asp Asn Pro Gly
1               5                   10                  15

Lys Glu
```

<210> SEQ ID NO 24
<211> LENGTH: 18
<212> TYPE: PRT
<213> ORGANISM: Homo sapiens

<400> SEQUENCE: 24

```
Lys Met Gly Ser Ser Val Glu Asn Asp Asn Pro Gly Lys Glu Val Asn
1               5                   10                  15

Lys Leu
```

<210> SEQ ID NO 25
<211> LENGTH: 12
<212> TYPE: PRT
<213> ORGANISM: Homo sapiens

<400> SEQUENCE: 25

```
Lys Glu Val Asn Lys Leu Ser Glu His Glu Arg Ser
1               5                   10
```

<210> SEQ ID NO 26
<211> LENGTH: 51
<212> TYPE: PRT
<213> ORGANISM: Homo sapiens

<400> SEQUENCE: 26

```
Arg Ser Ile Ser Pro Leu Leu Phe Glu Glu Ser Pro Ser Asp Val Gln
1               5                   10                  15

Pro Pro Gly Asp Pro Phe Gln Val Asn Phe Glu Glu Gln Asn Asn Pro
            20                  25                  30

Gln Ile Leu Gln Asn Ser Val Val Phe Gly Thr Ser Ala Gln Glu Val
        35                  40                  45

Val Lys Glu
    50
```

<210> SEQ ID NO 27
<211> LENGTH: 25
<212> TYPE: PRT
<213> ORGANISM: Homo sapiens

<400> SEQUENCE: 27

```
Arg Phe Arg Ile Glu Gln Lys Thr Thr Leu Thr Ala Ser Ala Gly Ile
1               5                   10                  15

Ala Pro Asn Thr Met Leu Ala Lys Val
            20                  25
```

<210> SEQ ID NO 28

<211> LENGTH: 19
<212> TYPE: PRT
<213> ORGANISM: Homo sapiens

<400> SEQUENCE: 28

Lys Thr Thr Leu Thr Ala Ser Ala Gly Ile Ala Pro Asn Thr Met Leu
1 5 10 15

Ala Lys Val

<210> SEQ ID NO 29
<211> LENGTH: 23
<212> TYPE: PRT
<213> ORGANISM: Homo sapiens

<400> SEQUENCE: 29

Lys Thr Thr Leu Thr Ala Ser Ala Gly Ile Ala Pro Asn Thr Met Leu
1 5 10 15

Ala Lys Val Ser Asp Lys Asn
20

<210> SEQ ID NO 30
<211> LENGTH: 19
<212> TYPE: PRT
<213> ORGANISM: Homo sapiens

<400> SEQUENCE: 30

Lys Val Ser Asp Lys Asn Lys Pro Asn Gly Gln Tyr Gln Ile Leu Pro
1 5 10 15

Asn Arg Gln

<210> SEQ ID NO 31
<211> LENGTH: 15
<212> TYPE: PRT
<213> ORGANISM: Homo sapiens

<400> SEQUENCE: 31

Lys Asn Lys Pro Asn Gly Gln Tyr Gln Ile Leu Pro Asn Arg Gln
1 5 10 15

<210> SEQ ID NO 32
<211> LENGTH: 16
<212> TYPE: PRT
<213> ORGANISM: Homo sapiens

<400> SEQUENCE: 32

Arg Gln Ala Val Met Asp Phe Ile Lys Asp Leu Pro Ile Arg Lys Val
1 5 10 15

<210> SEQ ID NO 33
<211> LENGTH: 13
<212> TYPE: PRT
<213> ORGANISM: Homo sapiens

<400> SEQUENCE: 33

Arg Lys Val Ser Gly Ile Gly Lys Val Thr Glu Lys Met
1 5 10

<210> SEQ ID NO 34
<211> LENGTH: 12
<212> TYPE: PRT
<213> ORGANISM: Homo sapiens

<400> SEQUENCE: 34

-continued

```
Lys Val Ser Gly Ile Gly Lys Val Thr Glu Lys Met
1               5                   10


<210> SEQ ID NO 35
<211> LENGTH: 18
<212> TYPE: PRT
<213> ORGANISM: Homo sapiens

<400> SEQUENCE: 35

Lys Met Leu Lys Ala Leu Gly Ile Ile Thr Thr Glu Leu Tyr Gln Gln
1               5                   10                  15

Arg Ala


<210> SEQ ID NO 36
<211> LENGTH: 15
<212> TYPE: PRT
<213> ORGANISM: Homo sapiens

<400> SEQUENCE: 36

Lys Ala Leu Gly Ile Ile Thr Thr Glu Leu Tyr Gln Gln Arg Ala
1               5                   10                  15


<210> SEQ ID NO 37
<211> LENGTH: 31
<212> TYPE: PRT
<213> ORGANISM: Homo sapiens

<400> SEQUENCE: 37

Arg Ala Leu Leu Ser Leu Leu Phe Ser Glu Thr Ser Trp His Tyr Phe
1               5                   10                  15

Leu His Ile Ser Leu Gly Leu Gly Ser Thr His Leu Thr Arg Asp
            20                  25                  30


<210> SEQ ID NO 38
<211> LENGTH: 13
<212> TYPE: PRT
<213> ORGANISM: Homo sapiens

<400> SEQUENCE: 38

Arg Asp Gly Glu Arg Lys Ser Met Ser Val Glu Arg Thr
1               5                   10


<210> SEQ ID NO 39
<211> LENGTH: 9
<212> TYPE: PRT
<213> ORGANISM: Homo sapiens

<400> SEQUENCE: 39

Arg Lys Ser Met Ser Val Glu Arg Thr
1               5


<210> SEQ ID NO 40
<211> LENGTH: 28
<212> TYPE: PRT
<213> ORGANISM: Homo sapiens

<400> SEQUENCE: 40

Arg Thr Phe Ser Glu Ile Asn Lys Ala Glu Glu Gln Tyr Ser Leu Gln
1               5                   10                  15

Glu Leu Ser Glu Leu Ala Gln Asp Leu Gln Lys Glu
            20                  25


<210> SEQ ID NO 41
```

<211> LENGTH: 21
<212> TYPE: PRT
<213> ORGANISM: Homo sapiens

<400> SEQUENCE: 41

Lys Ala Glu Glu Gln Tyr Ser Leu Gln Glu Leu Ser Glu Leu Ala Gln
1 5 10 15

Asp Leu Gln Lys Glu
20

<210> SEQ ID NO 42
<211> LENGTH: 20
<212> TYPE: PRT
<213> ORGANISM: Homo sapiens

<400> SEQUENCE: 42

Arg Leu Lys Gly Arg Thr Val Thr Ile Lys Leu Lys Asn Val Asn Phe
1 5 10 15

Glu Val Lys Thr
20

<210> SEQ ID NO 43
<211> LENGTH: 9
<212> TYPE: PRT
<213> ORGANISM: Homo sapiens

<400> SEQUENCE: 43

Lys Gly Arg Thr Val Thr Ile Lys Leu
1 5

<210> SEQ ID NO 44
<211> LENGTH: 16
<212> TYPE: PRT
<213> ORGANISM: Homo sapiens

<400> SEQUENCE: 44

Arg Thr Val Thr Ile Lys Leu Lys Asn Val Asn Phe Glu Val Lys Thr
1 5 10 15

<210> SEQ ID NO 45
<211> LENGTH: 18
<212> TYPE: PRT
<213> ORGANISM: Homo sapiens

<400> SEQUENCE: 45

Arg Thr Val Thr Ile Lys Leu Lys Asn Val Asn Phe Glu Val Lys Thr
1 5 10 15

Arg Ala

<210> SEQ ID NO 46
<211> LENGTH: 11
<212> TYPE: PRT
<213> ORGANISM: Homo sapiens

<400> SEQUENCE: 46

Lys Leu Lys Asn Val Asn Phe Glu Val Lys Thr
1 5 10

<210> SEQ ID NO 47
<211> LENGTH: 23
<212> TYPE: PRT
<213> ORGANISM: Homo sapiens

<400> SEQUENCE: 47

```
Lys Thr Arg Ala Ser Thr Val Ser Ser Val Val Ser Thr Ala Glu Glu
1               5                   10                  15

Ile Phe Ala Ile Ala Lys Glu
            20


<210> SEQ ID NO 48
<211> LENGTH: 39
<212> TYPE: PRT
<213> ORGANISM: Homo sapiens

<400> SEQUENCE: 48

Lys Thr Arg Ala Ser Thr Val Ser Ser Val Val Ser Thr Ala Glu Glu
1               5                   10                  15

Ile Phe Ala Ile Ala Lys Glu Leu Leu Lys Thr Glu Ile Asp Ala Asp
            20                  25                  30

Phe Pro His Pro Leu Arg Leu
        35


<210> SEQ ID NO 49
<211> LENGTH: 21
<212> TYPE: PRT
<213> ORGANISM: Homo sapiens

<400> SEQUENCE: 49

Arg Ala Ser Thr Val Ser Ser Val Val Ser Thr Ala Glu Glu Ile Phe
1               5                   10                  15

Ala Ile Ala Lys Glu
            20


<210> SEQ ID NO 50
<211> LENGTH: 25
<212> TYPE: PRT
<213> ORGANISM: Homo sapiens

<400> SEQUENCE: 50

Arg Ala Ser Thr Val Ser Ser Val Val Ser Thr Ala Glu Glu Ile Phe
1               5                   10                  15

Ala Ile Ala Lys Glu Leu Leu Lys Thr
            20                  25


<210> SEQ ID NO 51
<211> LENGTH: 37
<212> TYPE: PRT
<213> ORGANISM: Homo sapiens

<400> SEQUENCE: 51

Arg Ala Ser Thr Val Ser Ser Val Val Ser Thr Ala Glu Glu Ile Phe
1               5                   10                  15

Ala Ile Ala Lys Glu Leu Leu Lys Thr Glu Ile Asp Ala Asp Phe Pro
            20                  25                  30

His Pro Leu Arg Leu
        35


<210> SEQ ID NO 52
<211> LENGTH: 39
<212> TYPE: PRT
<213> ORGANISM: Homo sapiens

<400> SEQUENCE: 52

Arg Ala Ser Thr Val Ser Ser Val Val Ser Thr Ala Glu Glu Ile Phe
1               5                   10                  15
```

Ala Ile Ala Lys Glu Leu Leu Lys Thr Glu Ile Asp Ala Asp Phe Pro
20 25 30

His Pro Leu Arg Leu Arg Leu
35

<210> SEQ ID NO 53
<211> LENGTH: 16
<212> TYPE: PRT
<213> ORGANISM: Homo sapiens

<400> SEQUENCE: 53

Lys Thr Glu Ile Asp Ala Asp Phe Pro His Pro Leu Arg Leu Arg Leu
1 5 10 15

<210> SEQ ID NO 54
<211> LENGTH: 9
<212> TYPE: PRT
<213> ORGANISM: Homo sapiens

<400> SEQUENCE: 54

Arg Leu Arg Leu Met Gly Val Arg Ile
1 5

<210> SEQ ID NO 55
<211> LENGTH: 17
<212> TYPE: PRT
<213> ORGANISM: Homo sapiens

<400> SEQUENCE: 55

Arg Leu Met Gly Val Arg Ile Ser Ser Phe Pro Asn Glu Glu Asp Arg
1 5 10 15

Lys

<210> SEQ ID NO 56
<211> LENGTH: 18
<212> TYPE: PRT
<213> ORGANISM: Homo sapiens

<400> SEQUENCE: 56

Arg Leu Met Gly Val Arg Ile Ser Ser Phe Pro Asn Glu Glu Asp Arg
1 5 10 15

Lys His

<210> SEQ ID NO 57
<211> LENGTH: 13
<212> TYPE: PRT
<213> ORGANISM: Homo sapiens

<400> SEQUENCE: 57

Arg Ile Ser Ser Phe Pro Asn Glu Glu Asp Arg Lys His
1 5 10

<210> SEQ ID NO 58
<211> LENGTH: 10
<212> TYPE: DNA
<213> ORGANISM: Artificial Sequence
<220> FEATURE:
<223> OTHER INFORMATION: SYNTHESIZED

<400> SEQUENCE: 58
ttttttttgc 10

-continued

```
<210> SEQ ID NO 59
<211> LENGTH: 19
<212> TYPE: DNA
<213> ORGANISM: Artificial Sequence
<220> FEATURE:
<223> OTHER INFORMATION: SYNTHESIZED

<400> SEQUENCE: 59

tcaccctcgt acgactctt                                                   19


<210> SEQ ID NO 60
<211> LENGTH: 29
<212> TYPE: DNA
<213> ORGANISM: Artificial Sequence
<220> FEATURE:
<223> OTHER INFORMATION: SYNTHESIZED

<400> SEQUENCE: 60

gcaaaaaaaa aagagtcgta cgagggtga                                        29
```